(12) United States Patent
Haap et al.

(10) Patent No.: US 8,163,778 B2
(45) Date of Patent: Apr. 24, 2012

(54) PYRIDINES AS FBPASE INHIBITORS FOR TREATMENT OF DIABETES

(75) Inventors: Wolfgang Haap, Loerrach (DE); Paul Hebeisen, Basel (CH); Eric Argirios Kitas, Aesch BL (CH); Bernd Kuhn, Reinach BL (CH); Peter Mohr, Basel (CH); Hans Peter Wessel, Schliengen (DE)

(73) Assignee: Hoffmann-LA Roche Inc., Nutley, NJ (US)

( * ) Notice: Subject to any disclaimer, the term of this patent is extended or adjusted under 35 U.S.C. 154(b) by 547 days.

(21) Appl. No.: 12/276,440

(22) Filed: Nov. 24, 2008

(65) Prior Publication Data

US 2009/0143439 A1    Jun. 4, 2009

(30) Foreign Application Priority Data

Nov. 30, 2007 (EP) .................................... 07122017

(51) Int. Cl.
*C07D 409/02* (2006.01)
*A61K 31/4439* (2006.01)

(52) U.S. Cl. ........ 514/339; 514/337; 514/340; 514/352; 546/269.1; 546/277.4; 546/280.4; 546/281.1; 546/304

(58) Field of Classification Search ........................ None
See application file for complete search history.

(56) References Cited

U.S. PATENT DOCUMENTS

| | | | | |
|---|---|---|---|---|
| 2,977,375 A * | 3/1961 | Haack et al. | ..................... | 564/40 |
| 4,293,330 A | 10/1981 | Levitt | | |
| 2002/0193596 A1 | 12/2002 | Sebti et al. | | |

FOREIGN PATENT DOCUMENTS

| | | |
|---|---|---|
| DE | 1011413 | 7/1957 |
| DE | 9688 | 4/2010 |
| DK | 2006 00313 | 3/2006 |
| EP | 0503162 | 9/1992 |
| GB | 797474 | 7/1958 |
| WO | 96/30341 | 10/1996 |
| WO | WO 01/47935 | 7/2001 |
| WO | WO 2004/009118 | 1/2004 |

OTHER PUBLICATIONS

Lai C et al, Bioorganic & Medicinal Chemistry Letters, "Benzoxazole benzenesulfonamides as allosteric inhibotrrs of fructose-1,6-bisphosphatase" (2006) 16:7 1807-1810 XP025106972.
Holland, G.F., J Org. Chem. 26:(1961) 1662-1665 XP002563968 "Preparation of Some Additional Sulfonylureas".
Van Poelje, P. D. et al, *Diabetes*, (2006) 55(6), 1747-1754.
Hof H., et al., Arzneimittel Forschung, Drug Research 37(I), No. 3 (1987), XP002128088.
Rusching H., et al., Arzneimittel Forschung, Drug Research, vol. 8, No. 7a, pp. 448-454 (1958), XP009088824.
Husain M. I., et al., Indian Drugs, vol. 24, No. 1, pp. 21-23 (1986).
Abou Ouf et al, *Jour. of Drug Reseasrch Egypt*, (1974) 6:2 123-129.
Wu T-A et al, Journal of the Taiwan Pharmaceutical Assoc., 28:1-2, 56-58 XP008111887, 1977.
Lai C et al, *Bioorganic & Medicinal Chem. Letters*, (2006) 16:7 1807-1810 XP025106972.

* cited by examiner

*Primary Examiner* — Zinna Northington Davis
(74) *Attorney, Agent, or Firm* — George W. Johnston; Dennis P. Tramaloni; Samuel H. Megerditchian

(57) ABSTRACT

Compounds of formula (I)

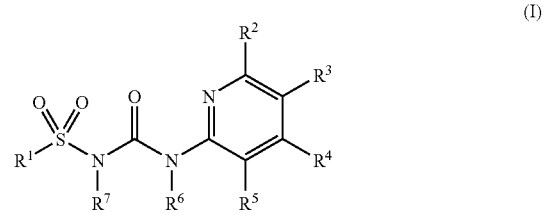

as well as pharmaceutically acceptable salts and esters thereof wherein the residues have the significance given in claim 1 and which can be used in the form of pharmaceutical compositions.

7 Claims, No Drawings

PYRIDINES AS FBPASE INHIBITORS FOR TREATMENT OF DIABETES

PRIORITY TO RELATED APPLICATION(S)

This application claims the benefit of European Patent Application No. 07122017.2, filed Nov. 30, 2007, which is hereby incorporated by reference in its entirety.

FIELD OF THE INVENTION

The present invention relates to novel compounds useful as FBPase inhibitors.

The invention is concerned particularly with compounds of formula (I)

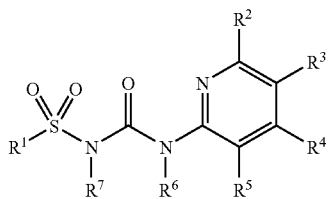

and pharmaceutically acceptable salts and esters thereof.

All documents relied upon or cited to below are expressly incorporated herein by reference.

BACKGROUND OF THE INVENTION

Fructose-1,6-bisphosphatase (FBPase) is a rate-limiting enzyme of gluconeogenesis that is allosterically regulated by AMP and responsible for the hydrolysis of Fructose-1,6-bisphosphate to Fructose-6-phosphate. FBPase AMP site inhibitors have valuable pharmacological properties suitable in both human and veterinary medicine.

As inhibitors of FBPase and of the production of Fructose-6-phosphate that is reversibly converted to Glucose-6-phosphate, a metabolite which represents a common precursor for diverse essential metabolic pathways generating glucose, glycogen, ATP, amino acids, nucleotides, NADPH and so forth, have a large variety of indications related to the management of body homeostasis and the prevention of metabolic dysfunctions.

SUMMARY OF THE INVENTION

In an embodiment of the present invention, provided is a compound of formula (I):

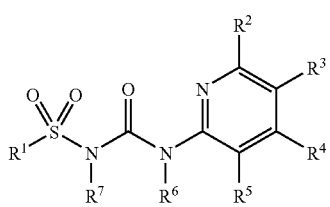

wherein:
$R^1$ is
(i) a benzo-condensed phenyl, thiophenyl, furyl or pyrrolyl ring,
wherein the benzo-condensed ring is optionally substituted with one to four substituents independently selected from $-R^8$, $-O-R^8$, $-R^9-O-R^8$, $-S-R^8$, $-R^9-S-R^8$, halogen, $-COR^8$, $-R^9-COR^8$, cyano, $-R^9$-cyano, nitro and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, $-O-R^8$, $-R^9-O-R^8$, $-S-R^8$, $-R^9-S-R^8$, $-COR^8$, $-R^9-COR^8$, cyano or nitro,
(ii) a phenyl ring which is substituted with one to four substituents independently selected from $-R^8$, $-O-R^8$, $-R^9-O-R^8$, $-S-R^8$, $-R^9-S-R^8$, halogen, $-COR^8$, $-R^9-COR^8$, cyano, $-R^9$-cyano, nitro, and a saturated and unsaturated mono- or polycyclic hydrocarbon ring with up to 10 ring atoms which may comprise up to 4 heteroatoms selected from N, S and O, which is optionally substituted with one to three substituents independently selected from halogen, $-R^8$, $-O-R^8$, $-R^9-O-R^8$, $-S-R^8$, $-R^9-S-R^8$, $-COR^8$, $-R^9-COR^8$, cyano or nitro
or condensed with a 5- or 6-membered saturated ring which may comprise up to 3 heteroatoms selected from N, S and O; wherein the condensed ring is optionally substituted with one to three substituents independently selected from $-R^8$, $-O-R^8$, $-R^9-O-R^8$, $-S-R^8$, $-R^9-S-R^8$, halogen, $-COR^8$, $-R^9-COR^8$, cyano, $-R^9$-cyano, nitro, and a saturated or mono- or polyunsaturated mono- or polycyclic hydrocarbon ring with up to 10 ring atoms which may comprise up to 4 heteroatoms selected from N, S and O, which is optionally substituted with one to three substituents independently selected from halogen, $R^8$, $-O-R^8$, $-R^9-O-R^8$, $-S-R^8$, $-R^9-S-R^8$, $-COR^8$, $-R^9-COR^8$, cyano or nitro, with the proviso that at position 3 and/or 4 of the phenyl ring, there is at least one substituent different from hydrogen, wherein the linking atom of the phenyl ring is defined as position 1,
with the further proviso that when the substituent at position 4 of the phenyl ring is methyl, $-O$-methyl, $-CO$-methyl, chloro or fluoro; and the substituent at position 3 of the phenyl ring is hydrogen, then substituent $R^3$ of the pyridine ring is bromo or chloro,
(iii) a thiophenyl ring which is substituted with one to four substituents independently selected from $-R^8$, $-O-R^8$, $-R^9-O-R^8$, $-S-R^8$, $-R^9-S-R^8$, halogen, $-COR^8$, $-R^9-COR^8$, cyano, $-R^9$-cyano, nitro, and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, $-O-R^8$, $-R^9-O-R^8$, $-S-R^8$, $-R^9-S-R^8$, $-COR^8$, $-R^9-COR^8$, cyano or nitro,
with the proviso that there is at least one substituent different from hydrogen, $C_2$-$C_3$-halo-alkyl, and $C_2$-$C_3$-halo-alkenyl;
(iv) a furyl ring which is substituted with one to four substituents independently selected from $-R^8$, $-O-R^8$, $-R^9-O-R^8$, $-S-R^8$, $-R^9-S-R^8$, halogen, $-COR^8$, $-R^9-COR^8$, cyano, $-R^9$-cyano, nitro, and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, —O—$R^8$, —$R^9$—O—$R^8$, —S—$R^8$, —$R^9$—S—$R^8$, —$COR^8$, —$R^9$—$COR^8$, cyano or nitro, $R^2$ and $R^4$ are independently selected from halogen, cyano, nitro, hydroxy, —$R^8$, —O—$R^8$, —S—$R^8$, —$N(R^8)_2$, —SO—$R^8$, —$SO_2$—$R^8$, —CO—$R^8$, —$CO_2$—$R^8$, —O—$COR^8$, —$CON(R^8)_2$, —$NR^8$—$COR^8$, $NR^8$—$COOR^8$, —$R^9$—O—$R^8$, —$R^9$—S—$R^8$, —$R^9$—$N(R^8)_2$, —$R^9$—SO—$R^8$, —$R^9$—$SO_2$—$R^8$, —$R^9$—$COR^8$, —$R^9$—$CO_2$—$R^8$, —$R^9$—O—CO—$R^8$, —$R^9$—$CO(NR^8)_2$, —$R^9$—$NR^8$—$COR^8$, —$NR^6$—CO—$N(R^8)_2$, —$NR^6$—CO—$N(R^6)$—$SO_2$—$R^8$, $NR^6$—CS—$N(R^8)_2$, —$NR^6$—CS—$SO_2$—$R^8$ or —$CN(R^8)_2$=NOH;

$R^3$ and $R^5$ are independently hydrogen;

$R^6$ and $R^7$ are independently selected from hydrogen, alkyl, haloalkyl, hydroxyalkyl and —$R^9$—O—CO—$R^8$;

$R^8$ is in each case independently selected from hydrogen or a saturated or mono- or polyunsaturated acyclic or cyclic organic residue with up to 20 ring atoms which may comprise up to 5 heteroatoms selected from N, S and/or O, which may be substituted by halogen, cyano, nitro, hydroxy, amino, alkoxy, haloalkoxy, carboxyamide and carboxyester; and $R^9$ is selected from alkylene, arylene, aralkylene or alkarylene;

and pharmaceutically acceptable salts and esters thereof.

In another embodiment of the invention, provided is a process for the preparation of a compound of formula I

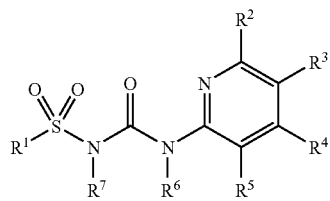

comprising one of the following reactions:
a) reacting a compound according to formula II

in the presence of a base in order to obtain a compound of formula III;
b) reacting a compound of formula III

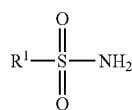

in the presence of a base with a compound of formula IV PhOC(O)Cl, in order to obtain a compound of formula V

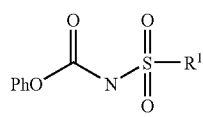

c) reacting a compound of formula V with a compound of formula VI

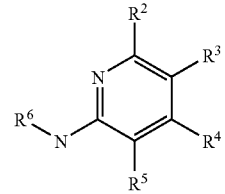

in order to obtain a compound of formula I

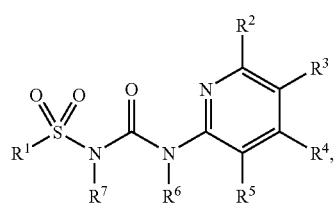

wherein $R^1$ to $R^9$ are defined above.

In a further embodiment of the present invention, provided is a pharmaceutical composition, comprising a therapeutically effective amount of a compound according to claim 1 and a therapeutically inert carrier.

DETAILED DESCRIPTION

As inhibitors of FBPase and of gluconeogenesis in the liver, or in other organs capable of producing glucose like kidney or intestine, compounds of the present invention are hypoglycaemic agents and are indicated for the treatment and/or the prophylaxis of disorders of glucose homeostasis, such as Diabetes Mellitus, in particular Type II and Type I Diabetes Mellitus (NIDDM and IDDM), Impaired Fasting Glucose (IFG), Impaired Glucose Tolerance (IGT), and for the prevention of the progression of disorders of the Metabolic Syndrome (MetS, also described as Syndrome X or Insulin Resistance Syndrome) which most important components are insulin resistance (with or without IGT), obesity, dyslipidemia, hypertension, prothrombic and proinflammatory states. As such, compounds of the present invention are also indicated for the prevention and/or the treatment of diabetic complications or diabetic-associated diseases such as cardiomyopathy, macrovascular atherosclerotic disorders, including coronary, cerebrovascular and peripheral artery diseases, microvascular diseases including retinopathy, cataracts, blindness and nephropathy, neuropathy (peripheral neuropathy and sympathetic nerve disorders), diabetic necrosis, infection or depression, and so forth.

In addition, as inhibitors of FBPase that cause the accumulation of Fructose-1,6-bisphosphate capable for increasing the glycolytic production of ATP, compounds of the present invention have cytoprotective effects as anti-ischaemic agents and are useful for preventing ischaemia-induced tissue damage. Therefore, compounds of the present invention can be used in a variety of ischaemic and inflammatory conditions where acute management of tissue injury could be beneficial such as surgical trauma, myocardial infarction, congestive heart failure, stroke, sickle cell disease, and so forth, and have further utility in cardioprotection, in improving cardiac function and tolerance to exercise, in improving red-blood cells and pulmonary endothelial functions, in organ preservation in transplants, and so forth. As such, compounds of the present invention can also be used to treat asthma attacks, hypertension, atheriosclerosis and so forth, and in the management of certain excess glycogen storage diseases such as McArdle disease (GSD-Type V) and others.

Also as inhibitors of FBPase, and thereby of the production from the gluconeogenic pathway of Fructose-6-phosphate and Glucose-6-phosphate that serve as precursors for other pathways of hexose metabolism (e.g. synthesis of aminosugars/hexosamines that are used for the biosynthesis of glycoproteins, glycosphingolipids or glycosaminoglycans, and uronic acid pathway that leads to glucuronate, a precursor of proteoglycans and conjugated glucuronides, and so forth), or for the pentose phosphate pathway (PPP, also called phosphogluconate pathway) which provides the carbon source for common aromatic biosynthetic pathways (nucleotides and amino-acids synthesis) and generates NADPH for reductive biosyntheses (lipogenesis, steroidogenesis), compounds of the present invention can have further utility in the prevention and/or the management of a large set of diseases including obesity, atherosclerosis, inflammation, Alzheimer disease, cancer or respiratory disorders such as excess mucus production and allergic asthma, excess surfactant synthesis, cystic fibrosis, and so forth.

Furthermore, compounds of the present invention can be used in any disease, syndrome, symptom or organ malfunction found associated with increased expression and/or activity of one or another FBPase isoform, at the obvious exception of certain deficiencies where FBPase upregulation might be beneficial for ensuring normal body function, e.g. certain glycogen storage diseases, such as GSD-Type 0 (glycogen synthase deficiency).

The compounds of formula I and their pharmaceutically acceptable salts and esters are novel and have valuable pharmacological properties. In particular they are FBPase inhibitors and can be used in the prophylaxis and/or treatment of Diabetes Mellitus such as Type I, Type II and Type III Diabetes, Impaired Fasting Glucose (IFG), Impaired Glucose Tolerance (IGT), Metabolic Syndrome, insulin resistance, dyslipidemia, obesity, hypertension, atherosclerosis, diabetic complications, inflammation, respiratory diseases or ischaemia. Preferred is the prophylaxis and/or prevention of progression and/or treatment of Diabetes Mellitus Type II, Diabetes Mellitus Type I, Diabetes Mellitus Type III, Impaired Fasting Glucose (IFG), Impaired Glucose Tolerance (IGT), Metabolic Syndrome, diabetic complications and ischaemia. Particularly preferred is the prophylaxis and/or treatment of Diabetes Mellitus Type II and Diabetes Mellitus Type I.

The present invention provides for compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, particularly Diabetes Mellitus Type II and Diabetes Mellitus Type I.

The compounds of the present invention can be combined with one or more additional active substances indicated for the management of human and veterinary homeostasis in any suitable ratio. Such substances may be insulin sensitizers such as peroxisome proliferator-activated receptor modulators (PPAR alpha, gamma, delta agonists, particularly with thiazolinediones such as rosiglitazone and pioglitazone), insulin secretagogues (sulfonylureas such as glyburide, glimepiride and glipizide, and non-sulfonylurea secretagogues such as the meglitinides repaglinide and nateglinide), insulin, metformin, alpha-glucosidase inhibitors (e.g. acarbose, miglitol), glucagon-like peptide (GLP-1) analogues (e.g. exenatide), dipeptidyl peptidase-IV (DPP-IV) inhibitors, glycogen phosphorylase inhibitors, glycogen synthase kinase-3 inhibitors, 11β-hydroxysteroid dehydrogenase-1 inhibitors, carnitine palmitoyltranferase-1 inhibitors, glucocorticoid receptor antagonists, glucagon receptor antagonists, Adenosine ($A_{2B}$) receptor agonists, amylin agonists (e.g. pramlintide), lipase inhibitor (e.g. orlistat), or any other synthetic or natural substance presenting valuable pharmacological properties useful for the treatment and/or the prevention of metabolic dysfunctions.

In the present invention, the term "alkyl", alone or in combination, signifies a straight-chain or branched-chain alkyl group with 1 to 20 carbon atoms, preferably a straight-chain or branched-chain alkyl group with 1 to 12 carbon atoms and particularly preferred a straight or branched-chain alkyl group with 1 to 8 carbon atoms and more preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl and propyl and most preferred methyl.

The term "saturated monocyclic hydrocarbon ring", alone or in combination, signifies a cycloalkyl ring with 3 to 8 carbon atoms, preferably a cycloalkyl ring with 3 to 6 carbon atoms and more preferably a cycloalkyl ring with 5 or 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopentyl and cyclohexyl.

The term "unsaturated monocyclic hydrocarbon ring", alone or in combination, signifies a hydrocarbon ring with 3 to 8 carbon atoms, preferably 3 to 6 carbon atoms, and more preferably 5 or 6 carbon atoms, which comprises at least one unsaturated bond. The term also includes aromatic ring systems. Examples of $C_3$ to $C_8$ cycloalkyl rings are phenyl rings.

The term "saturated or unsaturated polycyclic hydrocarbon ring", alone or in combination signifies a ring system having at least two condensed rings.

The term "bicyclic hydrocarbon ring" alone or in combination, signifies a bicycloalkyl ring having two condensed saturated or two unsaturated rings or two rings wherein at least one ring is saturated, with 6 to 10 carbon atoms, preferably 6 to 9 carbon atoms. Examples of preferred bicyclic rings are benzo-condensed phenyl rings.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy and most preferred methoxy.

The term "haloalkyl", alone or in combination, signifies an alkyl group as previously defined, wherein one to five hydrogen atoms are substituted by halogen, preferably fluoro. Preferred examples are monofluoroethyl, difluoroethyl, difluoromethyl and trifluoromethyl.

The term "haloalkoxy", alone or in combination, signifies a group of the formula haloalkyl-O— in which the term "haloalkyl" is defined as before. Particularly preferred is fluoromethoxy, and more preferred difluoromethoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl, hydroxyethyl, hydroxypropyl and 3-hydroxybutyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, haloalkoxy, alkoxyalkoxy, alkylene-cyano. Preferred examples are phenyl or phenyl substituted with one to three, preferably one or two substituents independently selected from methyl, difluoromethoxy, trifluoromethyl, methoxyethoxy, chloro and —$CH_2$-cyano.

The term "aryloxy", alone or in combination, signifies an aryl-O— group in which the term "aryl" has the previously given significance.

The term "alkoxyalkyl", alone or in combination, signifies an alkyl group as defined before, wherein one or more hydrogen atoms, preferably one hydrogen atom is replaced by an alkoxy group as defined before. Examples of alkoxyalkyl are methoxymethyl and methoxyethyl.

The term "alkoxycarbonyl", alone or in combination, signifies an alkoxy-CO— group in which the term "alkoxy" has the previously given significance.

The term "alkoxyalkoxy", alone or in combination, signifies an alkoxy group as defined before, wherein one or more hydrogen atoms, preferably one hydrogen atom is replaced by an alkoxy group as defined before. Examples of alkoxyalkoxy are methoxymethoxy and methoxyethoxy.

The term "hydroxyalkoxy", alone or in combination, signifies an alkoxy group as defined before, wherein one or more hydrogen atoms, preferably one hydrogen atom is replaced by an hydroxy group. An example of hydroxyalkoxy is hydroxyethoxy.

The term "mono- or polycyclic hydrocarbon ring which comprises up to 4 heteroatoms", alone or in combination, signifies a heterocyclyl, i.e. a saturated, partially unsaturated or aromatic mono- or bicyclic 5- to 10-membered heterocycle which contains one or more hetero atoms selected from nitrogen, oxygen and sulphur, preferably nitrogen and oxygen. The monocyclic ring has preferably 3 to 8 carbon atoms, more preferably 3 to 6 carbon atoms, and still more preferably 5 or 6 carbon atoms. The bicyclic ring has two saturated or two unsaturated rings or two rings wherein at least one ring is saturated, with 6 to 16 carbon atoms, preferably 6 to 12 carbon atoms, more preferably 6 to 10 or 6 to 9 carbon atoms. If desired, the heterocyclyl can be substituted with one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e., N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrridinyl, pyrazinyl, pyrimidinyl, hexahydro-pyrimidinyl, furyl, thienyl, thiazolyl, oxadiazolyl, oxazolyl, isoxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), dihydroquinolyl, 3,4-dihydroisoquinolyl and quinoxalinyl. Preferred are morpholinyl, oxadiazolyl, dihydroisoquinolinyl, pyrridinyl, oxazolyl, thienyl, pyrazolyl, thiazolyl, 1,2,3-thiadiazolyl and pyrrolidinyl, wherein oxazolyl, thienyl, pyrazolyl, thiazolyl, 1,2,3-thiadiazolyl and pyrrolidinyl are optionally substituted with one to three substituents, preferably one or two substituents independently selected from alkyl, halogen and cyclalkyl, particularly cyclohexyl. Most preferred monocyclic rings are pyrridinyl, furyl, thiophenyl and oxadiazolyl rings. Most preferred bicyclic rings are benzo-condensed thiophenyl, furyl and pyrrolyl rings.

The term "heterocycloalkyl", alone or in combination, signifies the heterocyclyl-alkyl group, wherein the terms "heterocyclyl" and "alkyl" are as previously defined.

The term "amino", alone or in combination, signifies a primary, secondary or tertiary amino group bonded via the nitrogen atom, with the secondary amino group carrying at least one hydrogen and an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "alkaryl", alone or in combination, signifies the alkyl-aryl group, wherein the terms "alkyl" and "aryl" are as previously defined. Preferred is methylphenyl.

The term "aralkyl", alone or in combination, signifies the aryl-alkyl group, wherein the terms "aryl" and "alkyl" are as previously defined. Preferred is benzyl.

The term "oxy", alone or in combination, signifies the —O— group.

The term "hydroxy", alone or in combination signifies the group —OH.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, triethylamine, diethylamine, N,N-diethylethanamine, triethylamine, tripropylamine, ethanolamine, lysine, arginine, N-ethylpiperidine, piperidine, polymine resins and the like. The compound of formula I can also be present in the form of zwitterions. A preferred pharmaceutically acceptable salt of compounds of formula I is the sodium salt, the triethylammonium and/or the N,N-diethylethanamine salt.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters.

Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Further preferred are the compounds of formula

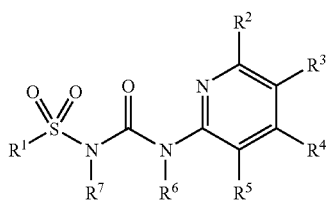

(I)

wherein
$R^1$ is
(i) a benzo-condensed phenyl, thiophenyl, furyl or pyrrolyl ring,
wherein the benzo-condensed ring is optionally substituted with one to four substituents independently selected from —$R^8$, —O—$R^8$, and halogen;
(ii) a phenyl ring which is substituted with one to four substituents independently selected from —$R^8$, —O—$R^8$, halogen and —$R^9$-cyano;
or condensed with a 5- or 6-membered saturated ring which may comprise up to 3 heteroatoms selected from N, S and O;
with the proviso that at position 3 and/or 4 of the phenyl ring, there is at least one substituent different from hydrogen, wherein the linking atom of the phenyl ring is defined as position 1,
with the further proviso that when the substituent at position 4 of the phenyl ring is methyl, —O-methyl, —CO-methyl, chloro or fluoro; and the substituent at position 3 of the phenyl ring is hydrogen, then substituent $R^3$ of the pyridine ring is bromo or chloro,
(iii) a thiophenyl ring which is substituted with one or two substituents independently selected from —$R^8$, —O—$R^8$, —$R^9$—O—$R^8$ and halogen;
with the proviso that there is at least one substituent different from hydrogen, halo-$C_2$-$C_3$-alkyl and halo-$C_2$-$C_3$-alkenyl;
(iv) a furyl ring which is substituted with one or two substituents independently selected from —$R^8$ and —$R^9$—O—$R^8$;
$R^2$ is selected from halogen, cyano, hydroxy, —$R^8$, —N($R^8$)$_2$, —$CO_2$—$R^8$, —CON($R^8$)$_2$, —$NR^8$—$COOR^8$, —$NR^6$—CO—N($R^8$)$_2$, —$NR^6$—CO—N($R^6$)$SO_2$—$R^8$, —$NR^6$—CS—N($R^8$)$_2$ and —CN($R^8$)$_2$=NOH;
$R^4$ is selected from halogen, cyano, —$R^8$, —O—$R^8$, —S—$R^8$, —SO—$R^8$, —$SO_2$—$R^8$, —$CO_2$—$R^8$, —CON($R^8$)$_2$ and —CN($R^8$)$_2$=NOH;
$R^3$ and $R^5$ are independently hydrogen;
$R^6$ is hydrogen;
$R^7$ is selected from hydrogen, alkyl and —$R^9$—O—CO—$R^8$;
$R^8$ is in each case independently selected from hydrogen or a saturated or mono- or polyunsaturated acyclic or cyclic organic residue with up to 12 ring atoms which may comprise up to 3 heteroatoms selected from N or O, which may be substituted by halogen, hydroxy, amino, alkoxy, carboxyamide and carboxyester; and
$R^9$ is alkylene or aralkylene;
and pharmaceutically acceptable salts and esters thereof.

Further preferred are compounds of formula I, wherein $R^1$ is a benzo-condensed phenyl, thiophenyl, furyl or pyrrolyl ring, wherein the benzo-condensed ring is optionally substituted with one to four substituents independently selected from —$R^8$, —O—$R^8$, and halogen.

Particularly preferred are those compounds according to formula I, wherein $R^1$ is as defined in (i). Still more particularly preferred are those compounds according to formula I, wherein $R^1$ is a benzo-condensed phenyl, thiophenyl, furyl or pyrrolyl ring, wherein the benzo-condensed ring is optionally substituted with one or two substituents independently selected from alkyl, alkoxy, —O—$R^9$-carboxyamide, alkoxyalkoxy, chloro and bromo. Most preferred are compounds according to formula I, wherein $R^1$ is a benzo-condensed phenyl, thiophenyl, furyl or pyrrolyl ring, wherein the benzo-condensed ring is optionally substituted with one or two substituents independently selected from methyl, methoxy, —O—$CH_2$-dimethylcarboxyamide, methoxyethoxy, chloro and bromo.

When $R^1$ is a benzo-condensed phenyl, the benzo-condensed ring is optionally substituted with 1 to 4 substituents independently selected from —$R^8$, —O—$R^8$, —$R^9$—O—$R^8$, —S—$R^8$, —$R^9$—S—$R^8$, halogen, —$COR^8$, —$R^9$—$COR^8$, cyano, —$R^9$-cyano, nitro and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, —O—$R^8$, —$R^9$—O—$R^8$, —S—$R^8$, —$R^9$—S—$R^8$ and —$COR^8$, —$R^9$—$COR^8$, cyano or nitro, preferably with one to four substituents independently selected from —R8, —O—R8, and halogen, still more preferably with one or two substituents independently selected from alkyl, alkoxy, —O—R9-carboxyamide, alkoxyalkoxy, chloro and bromo, and most preferably with one or two substituents independently selected from methyl, methoxy, —O—$CH_2$-dimethylcarboxyamide, methoxyethoxy, chloro and bromo.

When $R^1$ is a benzo-condensed thiophenyl ring, the benzo-condensed ring is optionally substituted with 1 to 4 substituents independently selected from —$R^8$, —O—$R^8$, —$R^9$—O—$R^8$, —S—$R^8$, —$R^9$—S—$R^8$, halogen, —$COR^8$, —$R^9$—$COR^8$, cyano, —$R^9$-cyano, nitro and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, —O—$R^8$, —$R^9$—O—$R^8$, —S—$R^8$, —$R^9$—S—$R^8$ and —$COR^8$, —$R^9$—$COR^8$, cyano or nitro, preferably with 1 to 4 substituents independently selected from —$R^8$, —O—$R^8$ and halogen, still more preferably with one or two substituents independently selected from alkyl, alkoxy, —O—$R^9$-carboxyamide, alkoxyalkoxy, chloro and bromo, and most preferably with one or two substituents independently selected from methyl, methoxy, —O—$CH_2$-dimethylcarboxyamide, methoxyethoxy, chloro and bromo.

Particularly preferred is the benzo-condensed thiophenyl ring substituted with one substituent independently selected from chloro, methoxy and methyl, and most preferably chloro.

When $R^1$ is a benzo-condensed furyl ring, the benzo-condensed ring is preferably optionally substituted with 1 to 4 substituents independently selected from —$R^8$, —O—$R^8$, —$R^9$—O—$R^8$, —S—$R^8$, —$R^9$—S—$R^8$, halogen, —$COR^8$, —$R^9$—$COR^8$, cyano, —$R^9$-cyano, nitro and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, —O—$R^8$, —$R^9$—O—$R^8$, —S—$R^8$, —$R^9$—S—$R^8$ and —$COR^8$, —$R^9$—$COR^8$, cyano or nitro, preferably with one to four substituents independently selected from —$R^8$, —O—$R^8$, and halogen, still more preferably with one or two substituents independently selected from alkyl, alkoxy, —O—$R^9$-carboxyamide, alkoxyalkoxy, chloro and bromo, and most preferably with one or two substituents independently selected from methyl, methoxy, —O—$CH_2$-dimethyl-carboxyamide, methoxyethoxy, chloro and bromo. Particularly preferably, the benzo-condensed furyl ring is unsubstituted or substituted with one substituent independently selected from bromo or chloro.

When $R^1$ is a benzo-condensed pyrrolyl ring, the benzo-condensed ring is optionally substituted with 1 to 4 substituents independently selected from —$R^8$, —O—$R^8$, —$R^9$—O—$R^8$, —S—$R^8$, —$R^9$—S—$R^8$, halogen, —$COR^8$, —$R^9$—$COR^8$, cyano, —$R^9$-cyano, nitro and saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, —O—$R^8$, —$R^9$—O—$R^8$, —S—$R^8$, —$R^9$—S—$R^8$ and —$COR^8$, —$R^9$—$COR^8$, cyano or nitro, preferably with one to four substituents independently selected from —$R^8$, —O—$R^8$, and halogen, still more preferably with one or two substituents independently selected from alkyl, alkoxy, —O—$R^9$-carboxyamide, alkoxyalkoxy, chloro and bromo, and most preferably with one or two substituents independently selected from methyl, methoxy, —O—$CH_2$-dimethyl-carboxyamide, methoxyethoxy, chloro and bromo.

Particularly preferably, the benzo-condensed pyrrolyl ring is substituted with one substituent independently selected from N-methyl, methoxy, methoxyethoxy and —O—CH2-dimethylcarboxyamide.

In a further preferred embodiment, the furyl ring is substituted with one to four substituents independently selected from —$R^8$, —O—$R^8$, —$R^9$—O—$R^8$, —S—$R^8$, —$R^9$—S—$R^8$, halogen, —$COR^8$, —$R^9$—$COR^8$, cyano, —$R^9$-cyano, nitro, and a saturated and/or unsaturated mono- or polycyclic hydrocarbon ring with up to 10 ring atoms which may comprise up to 4 heteroatoms selected from N, S and O, which is optionally substituted with one to three substituents independently selected from halogen, $R^8$, —O—$R^8$, —$R^9$—O—$R^8$, —S—$R^8$, —$R^9$—S—$R^8$ and —$COR^8$, —$R^9$—$COR^8$, cyano or nitro, preferably with alkyl and alkoxyalkyl and more preferably with methyl and methoxymethyl.

Moreover, preferred are the compounds of formula I, wherein $R^2$ is selected from halogen, cyano, hydroxy, —$R^8$, —$N(R^8)_2$, —$CO_2$—$R^8$, —$CON(R^8)_2$, —$NR^8$—$COOR^8$, —$NR^6$—CO—$N(R^8)_2$, —$NR^6$—CO—$N(R^6)SO_2$—$R^8$, —$NR^6$—CS—$N(R^8)_2$ and —$CN(R^8)_2$=NOH. Particularly preferred are those compounds, wherein $R^2$ is selected from bromo; chloro; cyano; hydroxy; hydrogen; a saturated or unsaturated monocyclic hydrocarbon ring comprising 6 ring atoms or bicyclic hydrocarbon ring comprising 10 ring atoms which may comprise 1 or 2 heteroatoms selected from O and N; an unsaturated monocyclic hydrocarbon ring comprising 5 ring atoms which comprises 3 heteroatoms selected from O and N; —$N(R^8)_2$, wherein $R^8$ is hydrogen or straight- or branched chain $C_1$-$C_4$-alkyl which may be substituted with amino, halogen, alkoxy, hydroxy or carboxyester, wherein at least one $R^8$ is hydrogen; —$CO_2$-alkyl; —$CON(R^8)_2$, —$NR^8$—$COOR^8$, —NH—CO—$N(R^8)_2$, —NH—CS—$N(R^8)_2$, —$CN(R^8)_2$=NOH; wherein $R^8$ is in each case independently hydrogen or alkyl; and —NH—CO—N(H)$SO_2$—$R^8$, wherein $R^8$ is phenyl which is substituted with haloalkoxy.

Further preferred are those compounds of formula I, wherein $R^2$ is selected from bromo; chloro; cyano; hydroxy; hydrogen; morpholinyl; phenyl substituted with trifluoromethyl; tetrahydronaphthalene; dihydroisoquinoline; methyl-1,2,4-oxadiazol; —$N(R^8)_2$, wherein $R^8$ is independently in each case hydrogen, methyl, 2-methylprop-2-en, 3-hydroxy-2-methylpropylamino, methyl substituted with dimethoxyphenyl, ethyl substituted with mono-, difluoro or hydroxy, propyl substituted with carboxymethylester, trifluoro, hydroxy or 3-hydroxybutyl substituted with hydroxy; —$CO_2$-methyl; —$CON(R^8)_2$, —$NR^8$—$COOR^8$, —NH—CO—$N(R^8)_2$, —NH—CS—$N(R^8)_2$, —$CN(R^8)_2$=NOH, wherein $R^8$ is in each case independently hydrogen or methyl; and —NH—CO—N(H)$SO_2$—$R^8$, wherein $R^8$ is phenyl substituted with difluoromethoxy.

Additionally preferred are the compounds of formula I, wherein $R^4$ is selected from halogen, cyano, —$R^8$, —O—$R^8$, —S—$R^8$, —SO—$R^8$, —$SO_2$—$R^8$, —$CO_2$—$R^8$, —CON$(R^8)_2$ and —$CN(R^8)_2$=NOH, more preferably from halogen; cyano; hydrogen; alkyl; haloalkyl; an unsaturated cyclic organic residue with 5 or 6 ring atoms comprising up to 3 heteroatoms selected from O and N, alkoxy; alkylthio; —SO-alkyl; —$SO_2$-alkyl; —$CO_2$-alkyl; —CON$(R^8)_2$ wherein $R^8$ is in each case independently hydrogen or alkyl; and —CN(H)$_2$=NOH, still more preferably from bromo; cyano; hydrogen; methyl; trifluoromethyl; 5-methyl-1,2,4-oxadiazol; methoxy; ethoxy; methylthio; ethylthio, —SO-methyl; —$SO_2$-methyl; —$CO_2$-ethyl; —CON$(R^8)_2$ wherein $R^8$ is in each case independently hydrogen or methyl; and —CN(H)$_2$=NOH.

Another preferred aspect of the present invention are compounds according to formula I, wherein $R^4$ is selected from bromo; cyano; hydrogen; methyl; trifluoromethyl; 5-methyl-1,2,4-oxadiazol; methoxy; ethoxy; methylthio; ethylthio;

—SO-methyl; —SO$_2$-methyl; —CO$_2$-ethyl; —CON(R$^8$)$_2$ wherein R$^8$ is in each case independently hydrogen or methyl; and —CN(H)$_2$=NOH.

Further preferred are those compounds according to formula I, wherein R$^3$ and R$^5$ are independently hydrogen.

Particularly preferred are the compounds of formula I, wherein R$^6$ is hydrogen.

Further preferred are compounds of formula I, wherein R$^7$ is selected from hydrogen, alkyl and —R$^9$—O—CO—R$^8$, more preferably from hydrogen, methyl and —CH$_2$—O—CO-tert-butyl.

Another preferred aspect of the present invention are the compounds of formula I, wherein R$^8$ is in each case independently selected from hydrogen or a saturated or mono- or polyunsaturated acyclic or cyclic organic residue with up to 12 ring atoms which may comprise up to 3 heteroatoms selected from N or O, which may be substituted by halogen, hydroxy, amino, alkoxy, carboxyamide and carboxyester.

Particularly preferred are those compounds of formula I, wherein R$^8$ is in each case independently selected from hydrogen, acyclic straight- or branched chain C$_1$-C$_4$-alkyl, saturated or unsaturated monocyclic organic residue with 5 or 6 ring atoms or bicyclic organic residue with 9 or 10 ring atoms which may comprise up to 3 heteroatoms selected from N or O, which may be substituted by halogen, hydroxy, amino, alkoxy, carboxyamide or carboxyester.

Examples of compounds of formula (I) are:
1. 5-Chloro-N-({4-methoxy-6-[(methylcarbamoyl)amino]pyridin-2-yl}carbamoyl)-1-benzothiophene-2-sulfonamide;
2. N-{[4-Bromo-6-(carbamoylamino)pyridin-2-yl]carbamoyl}-5-methylthiophene-3-sulfonamide;
3. N-({4-bromo-6-[(methylcarbamoyl)amino]pyridin-2-yl}carbamoyl)-5-methylthiophene-3-sulfonamide;
4. N-{[4-Bromo-6-(carbamoylamino)pyridin-2-yl]carbamoyl}-5-(2-methoxyethyl)-4-methylthiophene-2-sulfonamide;
5. 5-Methoxy-N-({4-methoxy-6-[(methylcarbamoyl)amino]pyridin-2-yl}carbamoyl)-1-benzothiophene-3-sulfonamide;
6. 5-Isobutyl-N-({4-methoxy-6-[(methylcarbamoyl)amino]pyridin-2-yl}carbamoyl)-4-methylthiophene-2-sulfonamide;
7. N-({4-Methoxy-6-[(methylcarbamoyl)amino]pyridin-2-yl}carbamoyl)-5-methyl-1-benzothiophene-2-sulfonamide;
8. N-({4-Bromo-6-[(methylcarbamoyl)amino]pyridin-2-yl}carbamoyl)-5-(2-methoxyethyl)-4-methylthiophene-2-sulfonamide;
9. N-[[[4-methoxy-6-[[(methylamino)carbonyl]amino]-2-pyridinyl]amino]carbonyl]-5-methyl-3-thiophenesulfonamide;
10. N-[(6-Amino-4-bromopyridin-2-yl)carbamoyl]-5-(2-methoxyethyl)-4-methylthiophene-2-sulfonamide;
11. N-[(6-Amino-4-bromopyridin-2-yl)carbamoyl]-4-chloro-5-(2-methoxyethyl)thiophene-2-sulfonamide;
12. 6-Methoxy-N-({4-methoxy-6-[(methylcarbamoyl)amino]pyridin-2-yl}carbamoyl)-1-benzothiophene-2-sulfonamide;
13. 5-Methoxy-N-({4-methoxy-6-[(methylcarbamoyl)amino]pyridin-2-yl}carbamoyl)-1-benzothiophene-2-sulfonamide;
14. 5-(2-Methoxyethyl)-4-methyl-N-({6-[(methylcarbamoyl)amino]-4-(methylthio)pyridin-2-yl}carbamoyl)thiophene-2-sulfonamide;
15. N-({4-Bromo-6-[(2,2-difluoroethyl)amino]pyridin-2-yl}carbamoyl)-4-chloro-5-(2-methoxyethyl)thiophene-2-sulfonamide;
16. 5-Methyl-N-({6-[(methylcarbamoyl)amino]-4-(methylthio)pyridin-2-yl}carbamoyl)thiophene-3-sulfonamide;
17. N-{[6-(Carbamoylamino)-4-(methylthio)pyridin-2-yl]carbamoyl}-5-(2-methoxyethyl)-4-methylthiophene-2-sulfonamide;
18. 5-(2-Methoxyethyl)-N-[(4-methoxy-6-{[(methylamino)carbonothioyl]amino}pyridin-2-yl)carbamoyl]-4-methylthiophene-2-sulfonamide;
19. N-({4-Bromo-6-[(2,2-difluoroethyl)amino]pyridin-2-yl}carbamoyl)-5-(2-methoxyethyl)-4-methylthiophene-2-sulfonamide;
20. 5-(2-Methoxyethyl)-N-({4-methoxy-6-[(methylcarbamoyl)amino]pyridin-2-yl}carbamoyl)-4-methylthiophene-2-sulfonamide;
21. N-[(6-Amino-4-bromopyridin-2-yl)carbamoyl]-5-(methoxymethyl)-4-methylthiophene-2-sulfonamide;
22. N-{[6-(Carbamoylamino)-4-methoxypyridin-2-yl]carbamoyl}-5-methylthiophene-3-sulfonamide;
23. N-({4-Cyano-6-[(methylcarbamoyl)amino]pyridin-2-yl}carbamoyl)-5-(2-methoxyethyl)-4-methylthiophene-2-sulfonamide;
24. N-{[6-(Carbamoylamino)-4-methoxypyridin-2-yl]carbamoyl}-5-(2-methoxyethyl)-4-methylthiophene-2-sulfonamide;
25. N-{[6-Bromo-4-(methylthio)pyridin-2-yl]carbamoyl}-5-(2-methoxyethyl)-4-methylthiophene-2-sulfonamide;
26. 7-Methoxy-N-({4-methoxy-6-[(methylcarbamoyl)amino]pyridin-2-yl}carbamoyl)-1-methyl-1H-indole-3-sulfonamide;
27. N-({4-Methoxy-6-[(methylcarbamoyl)amino]pyridin-2-yl}carbamoyl)-3-methylbenzenesulfonamide;
28. N-[(6-Amino-4-bromopyridin-2-yl)carbamoyl]-3-chlorobenzenesulfonamide;
29. 5-(Methoxymethyl)-N-({4-methoxy-6-[(methylcarbamoyl)amino]pyridin-2-yl}carbamoyl)thiophene-3-sulfonamide;
30. N-[(6-Amino-4-methoxypyridin-2-yl)carbamoyl]-5-(2-methoxyethyl)-4-methylthiophene-2-sulfonamide;
31. N-[(4-Bromo-6-morpholin-4-ylpyridin-2-yl)carbamoyl]-5-(2-methoxyethyl)-4-methylthiophene-2-sulfonamide;
32. N-{[6-Amino-4-(methylthio)pyridin-2-yl]carbamoyl}-5-(2-methoxyethyl)-4-methylthiophene-2-sulfonamide;
33. 5-(2-Methoxyethyl)-4-methyl-N-{[4-(trifluoromethyl)pyridin-2-yl]carbamoyl}thiophene-2-sulfonamide;
34. N-[(6-Amino-4-bromopyridin-2-yl)carbamoyl]-2,3-dihydro-1-benzofuran-5-sulfonamide;
35. N-({4-Ethoxy-6-[(methylcarbamoyl)amino]pyridin-2-yl}carbamoyl)-5-(2-methoxyethyl)-4-methylthiophene-2-sulfonamide;
36. N-[(6-Amino-4-bromopyridin-2-yl)carbamoyl]-3-methylbenzenesulfonamide;
37. N-[(6-Amino-4-bromopyridin-2-yl)carbamoyl]-2,3-dihydro-1,4-benzodioxine-6-sulfonamide;
38. 5-(2-Methoxyethoxy)-N-({4-methoxy-6-[(methylcarbamoyl)amino]pyridin-2-yl}carbamoyl)-4-methylthiophene-2-sulfonamide;
39. N-({4-Bromo-6-[(2,2-difluoroethyl)amino]pyridin-2-yl}carbamoyl)-3-methylbenzenesulfonamide;
40. N-{[6-(Carbamoylamino)-4-ethoxypyridin-2-yl]carbamoyl}-5-(2-methoxyethyl)-4-methylthiophene-2-sulfonamide;
41. N-({4-Bromo-6-[(2,2-difluoroethyl)amino]pyridin-2-yl}carbamoyl)-3-chlorobenzenesulfonamide;

42. 5-(2-Methoxyethyl)-4-methyl-N-({4-(trifluoromethyl)-6-[4-(trifluoromethyl)phenyl]pyridin-2-yl}carbamoyl)thiophene-2-sulfonamide;
43. N-{[6-Amino-4-(methylthio)pyridin-2-yl]carbamoyl}-5-methylthiophene-3-sulfonamide;
44. N-[(6-Amino-4-bromopyridin-2-yl)carbamoyl]-5-(methoxymethyl)-4-methylfuran-2-sulfonamide;
45. N-({6-[(2-Fluoroethyl)amino]-4-(methylthio)pyridin-2-yl}carbamoyl)-5-(2-methoxyethyl)-4-methylthiophene-2-sulfonamide;
46. 5-(2-Methoxyethyl)-4-methyl-N-{[4-methyl-6-(1,2,3,4-tetrahydronaphthalen-2-yl)pyridin-2-yl]carbamoyl}thiophene-2-sulfonamide;
47. N-({4-Bromo-6-[(2,2-difluoroethyl)amino]pyridin-2-yl}carbamoyl)-2,3-dihydro-1-benzofuran-5-sulfonamide;
48. N-({6-[(2-Hydroxyethyl)amino]-4-(methylthio)pyridin-2-yl}carbamoyl)-5-(2-methoxyethyl)-4-methylthiophene-2-sulfonamide;
49. 7-(2-Methoxyethoxy)-N-({4-methoxy-6-[(methylcarbamoyl)amino]pyridin-2-yl}carbamoyl)-1-methyl-1H-indole-2-sulfonamide;
50. 5-(2-Methoxyethyl)-4-methyl-N-({6-[(methylcarbamoyl)amino]-4-(methylsulfonyl)pyridin-2-yl}carbamoyl)thiophene-2-sulfonamide;
51. N-({4-Bromo-6-[(2,2-difluoroethyl)amino]pyridin-2-yl}carbamoyl)-4-(2-methoxyethoxy)-3-methylbenzenesulfonamide;
52. N,N'-[(4-Bromopyridine-2,6-diyl)bis(iminocarbonyl)]bis[3-(difluoromethoxy)benzenesulfonamide];
53. N-{[6-Amino-4-(methylthio)pyridin-2-yl]carbamoyl}-7-methoxy-1-methyl-1H-indole-3-sulfonamide;
54. N-({4-Bromo-6-[(dimethylcarbamoyl)amino]pyridin-2-yl}carbamoyl)-5-(2-methoxyethyl)-4-methylthiophene-2-sulfonamide;
55. N-[(4-Bromopyridin-2-yl)carbamoyl]-3-chlorobenzenesulfonamide;
56. N-{[6-(3,4-Dihydroisoquinolin-2(1H)-yl)-4-methylpyridin-2-yl]carbamoyl}-5-(2-methoxyethyl)-4-methylthiophene-2-sulfonamide;
57. N-[(6-Amino-4-bromopyridin-2-yl)carbamoyl]-4-(2-methoxyethoxy)-3-methylbenzenesulfonamide;
58. N-[(6-Cyano-4-methoxypyridin-2-yl)carbamoyl]-5-(2-methoxyethyl)-4-methylthiophene-2-sulfonamide;
59. N-({6-[(Dimethylcarbamoyl)amino]-4-methoxypyridin-2-yl}carbamoyl)-5-(2-methoxyethyl)-4-methylthiophene-2-sulfonamide;
60. N-[(4-Bromopyridin-2-yl)carbamoyl]-3-methylbenzenesulfonamide;
61. Methyl-{4-methoxy-6-[({[5-(2-methoxyethyl)-4-methyl-2-thienyl]sulfonyl}carbamoyl)amino]pyridin-2-yl}carbamate;
62. N-[(6-Amino-4-cyanopyridin-2-yl)carbamoyl]-5-(2-methoxyethyl)-4-methylthiophene-2-sulfonamide;
63. N-[(6-Amino-4-bromopyridin-2-yl)carbamoyl]-3-(difluoromethoxy)benzenesulfonamide;
64. N-[(6-Amino-4-ethoxypyridin-2-yl)carbamoyl]-5-(2-methoxyethyl)-4-methylthiophene-2-sulfonamide;
65. N-[(4-Bromopyridin-2-yl)carbamoyl]-5-[4-(cyanomethyl)phenyl]thiophene-2-sulfonamide;
66. N-({4-Bromo-6-[(2,4-dimethoxybenzyl)amino]pyridin-2-yl}carbamoyl)-5-(2-methoxyethyl)-4-methylthiophene-2-sulfonamide;
67. N,N'-[(4-Bromopyridine-2,6-diyl)bis(iminocarbonyl)]bis(3-chlorobenzenesulfonamide);
68. N-({6-[(Dimethylcarbamoyl)amino]-4-ethoxypyridin-2-yl}carbamoyl)-5-(2-methoxyethyl)-4-methylthiophene-2-sulfonamide;
69. N-[(4-Bromopyridin-2-yl)carbamoyl]-4-chlorobenzenesulfonamide;
70. 2-[(3-{[({4-Methoxy-6-[(methylcarbamoyl)amino]pyridin-2-yl}carbamoyl)amino]sulfonyl}-1-methyl-1H-indol-7-yl)oxy]-N,N-dimethylacetamide;
71. N-{[6-Hydroxy-4-(methylthio)pyridin-2-yl]carbamoyl}-5-(2-methoxyethyl)-4-methylthiophene-2-sulfonamide;
72. N-[(6-Chloropyridin-2-yl)carbamoyl]-3-methylbenzenesulfonamide;
73. Methyl-4-({6-[({[5-(2-methoxyethyl)-4-methyl-2-thienyl]sulfonyl}carbamoyl)amino]-4-(methylthio)pyridin-2-yl}amino)butanoate;
74. N-({6-[(3-Hydroxypropyl)amino]-4-(methylthio)pyridin-2-yl}carbamoyl)-5-(2-methoxyethyl)-4-methylthiophene-2-sulfonamide;
75. 5-(2-Methoxyethyl)-4-methyl-N-({4-(methylthio)-6-[(3,3,3-trifluoropropyl)amino]pyridin-2-yl}carbamoyl)thiophene-2-sulfonamide;
76. N-({4-(Ethylthio)-6-[(2-hydroxyethyl)amino]pyridin-2-yl}carbamoyl)-5-(2-methoxyethyl)-4-methylthiophene-2-sulfonamide;
77. 2-{3-Methyl-5-[({[4-(trifluoromethyl)pyridin-2-yl]carbamoyl}amino)sulfonyl]-2-thienyl}ethyl acetate;
78. 5-(2-Hydroxyethyl)-4-methyl-N-{[4-(trifluoromethyl)pyridin-2-yl]carbamoyl}thiophene-2-sulfonamide;
79. N-{[6-Amino-5-fluoro-4-(trifluoromethyl)pyridin-2-yl]carbamoyl}-5-(2-methoxyethyl)-4-methylthiophene-2-sulfonamide;
80. 5-(2-Methoxyethyl)-4-methyl-N-({6-[(2-methylprop-2-en-1-yl)amino]-4-(methylthio)pyridin-2-yl}carbamoyl)thiophene-2-sulfonamide;
81. 2-{5-[({[6-Amino-5-fluoro-4-(trifluoromethyl)pyridin-2-yl]carbamoyl}amino)sulfonyl]-3-methyl-2-thienyl}ethyl acetate;
82. N-[(6-Amino-4-bromopyridin-2-yl)carbamoyl]-1-benzofuran-3-sulfonamide;
83. N-[(6-Amino-4-bromopyridin-2-yl)carbamoyl]-5-bromo-1-benzofuran-3-sulfonamide;
84. N-{[6-Amino-5-fluoro-4-(trifluoromethyl)pyridin-2-yl]carbamoyl}-5-(2-hydroxyethyl)-4-methylthiophene-2-sulfonamide;
85. N-{[6-Amino-4-(trifluoromethyl)pyridin-2-yl]carbamoyl}-5-(2-methoxyethyl)-4-methylthiophene-2-sulfonamide;
86. 5-(2-Methoxyethyl)-4-methyl-N-{[6-methyl-4-(methylthio)pyridin-2-yl]carbamoyl}thiophene-2-sulfonamide;
87. N-{[6-Amino-4-(methylthio)pyridin-2-yl]carbamoyl}-5-bromo-1-benzofuran-3-sulfonamide;
88. Sodium-6-[({[5-(2-methoxyethyl)-4-methyl-2-thienyl]sulfonyl}carbamoyl)amino]-4-(methylthio)pyridine-2-carboxylate;
89. N-({6-[(Methylcarbamoyl)amino]-4-(methylthio)pyridin-2-yl}carbamoyl)-1-benzofuran-3-sulfonamide;
90. N-{[6-chloro-4-(trifluoromethyl)pyridin-2-yl]carbamoyl}-5-(2-methoxyethyl)-4-methylthiophene-2-sulfonamide;
91. Methyl-6-[({[5-(2-methoxyethyl)-4-methyl-2-thienyl]sulfonyl}carbamoyl)amino]-4-(trifluoromethyl)pyridine-2-carboxylate;
92. Methyl-6-[({[5-(2-acetoxyethyl)-4-methyl-2-thienyl]sulfonyl}carbamoyl)amino]-4-(trifluoromethyl)pyridine-2-carboxylate;
93. 2-{5-[({[6-chloro-4-(trifluoromethyl)pyridin-2-yl]carbamoyl}amino)sulfonyl]-3-methyl-2-thienyl}ethyl acetate;

94. 5-(2-Methoxyethyl)-4-methyl-N-({6-[(methylcarbamoyl)amino]-4-(methylsulfinyl)pyridin-2-yl}carbamoyl)thiophene-2-sulfonamide;
95. N-{[6-(Carbamoylamino)-4-(methylsulfinyl)pyridin-2-yl]carbamoyl}-5-(2-methoxyethyl)-4-methylthiophene-2-sulfonamide;
96. 5-(2-methoxyethyl)-4-methyl-N-{[6-methyl-4-(trifluoromethyl)pyridin-2-yl]carbamoyl}thiophene-2-sulfonamide;
97. Methyl-6-[({[5-(2-hydroxyethyl)-4-methyl-2-thienyl]sulfonyl}carbamoyl)amino]-4-(trifluoromethyl)pyridine-2-carboxamide;
98. Methyl-6-({[[(5-methyl-3-thienyl)sulfonyl]carbamoyl}amino)-4-(trifluoromethyl)pyridine-2-carboxylate;
99. Ethyl-2-[({[5-(2-methoxyethyl)-4-methyl-2-thienyl]sulfonyl}carbamoyl)amino]-6-[(methylcarbamoyl)amino]isonicotinate;
100. Ethyl-2-amino-6-[({[5-(2-methoxyethyl)-4-methyl-2-thienyl]sulfonyl}carbamoyl)amino]isonicotinate;
101. 2-[({[5-(2-Methoxyethyl)-4-methyl-2-thienyl]sulfonyl}carbamoyl)amino]-6-[(methylcarbamoyl)amino]isonicotinamide;
102. 2-Amino-6-[({[5-(2-methoxyethyl)-4-methyl-2-thienyl]sulfonyl}carbamoyl)amino]isonicotinamide;
103. 2-[({[5-(2-Methoxyethyl)-4-methyl-2-thienyl]sulfonyl}carbamoyl)amino]-N-methyl-6-[(methylcarbamoyl)amino]isonicotinamide;
104. 2-Amino-6-[({[5-(2-methoxyethyl)-4-methyl-2-thienyl]sulfonyl}carbamoyl)amino]-N-methylisonicotinamide;
105. Methyl-6-[({[5-(2-hydroxyethyl)-4-methyl-2-thienyl]sulfonyl}carbamoyl)amino]-4-(trifluoromethyl)pyridine-2-carboxylate;
106. 5-(2-Hydroxyethyl)-N-{[6-(hydroxymethyl)-4-(trifluoromethyl)pyridin-2-yl]carbamoyl}-4-methylthiophene-2-sulfonamide;
107. N'-Hydroxy-2-[({[5-(2-methoxyethyl)-4-methyl-2-thienyl]sulfonyl}carbamoyl)amino]-6-[(methylcarbamoyl)amino]pyridine-4-carboximidamide;
108. 2-Amino-N'-hydroxy-6-[({[5-(2-methoxyethyl)-4-methyl-2-thienyl]sulfonyl}carbamoyl)amino]pyridine-4-carboximidamide;
109. 5-(2-Methoxyethyl)-4-methyl-N-({6-[(methylcarbamoyl)amino]-4-(5-methyl-1,2,4-oxadiazol-3-yl)pyridin-2-yl}carbamoyl)thiophene-2-sulfonamide;
110. N-{[6-Amino-4-(5-methyl-1,2,4-oxadiazol-3-yl)pyridin-2-yl]carbamoyl}-5-(2-methoxyethyl)-4-methylthiophene-2-sulfonamide;
111. 2-{3-methyl-5-[({[6-methyl-4-(trifluoromethyl)pyridin-2-yl]carbamoyl}amino)sulfonyl]-2-thienyl}ethyl acetate;
112. 6-[({[5-(2-Methoxyethyl)-4-methyl-2-thienyl]sulfonyl}carbamoyl)amino]-4-(methylthio)pyridine-2-carboxamide;
113. 6-[({[5-(2-Methoxyethyl)-4-methyl-2-thienyl]sulfonyl}carbamoyl)amino]-N-methyl-4-(methylthio)pyridine-2-carboxamide;
114. 5-(2-Hydroxyethyl)-4-methyl-N-{[6-methyl-4-(trifluoromethyl)pyridin-2-yl]carbamoyl}thiophene-2-sulfonamide;
115. N'-Hydroxy-6-[({[5-(2-methoxyethyl)-4-methyl-2-thienyl]sulfonyl}carbamoyl)amino]-4-(methylthio)pyridine-2-carboximidamide;
116. 5-(2-Methoxyethyl)-4-methyl-N-{[6-(5-methyl-1,2,4-oxadiazol-3-yl)-4-(methylthio)pyridin-2-yl]carbamoyl}thiophene-2-sulfonamide;
117. 5-(2-methoxyethyl)-4-methyl-N-{[6-(5-methyl-1,2,4-oxadiazol-3-yl)-4-(methylthio)pyridin-2-yl]carbamoyl}thiophene-2-sulfonamide;
118. Methyl-6-[({[5-(2-methoxyethyl)-4-methyl-2-thienyl]sulfonyl}carbamoyl)amino]-4-(methoxy)pyridine-2-carboxylate;
119. 6-[({[5-(2-Methoxyethyl)-4-methyl-2-thienyl]sulfonyl}carbamoyl)amino]-4-(methoxy)pyridine-2-carboxamide;
120. 5-Methyl-N-{[6-methyl-4-(trifluoromethyl)pyridin-2-yl]carbamoyl}thiophene-3-sulfonamide;
121. 5-Methyl-N-{[6-methyl-4-(trifluoromethyl)pyridin-2-yl]carbamoyl}thiophene-2-sulfonamide; and
122. 4-Methyl-N-{[6-methyl-4-(trifluoromethyl)pyridin-2-yl]carbamoyl}thiophene-2-sulfonamide.

Preferred examples of compounds of formula (I) are:

5-Isobutyl-N-({4-methoxy-6-[(methylcarbamoyl)amino]pyridin-2-yl}carbamoyl)-4-methylthiophene-2-sulfonamide;

N-[[[4-methoxy-6-[[(methylamino)carbonyl]amino]-2-pyridinyl]amino]carbonyl]-5-methyl-3-thiophenesulfonamide;

5-Methyl-N-({6-[(methylcarbamoyl)amino]-4-(methylthio)pyridin-2-yl}carbamoyl)thiophene-3-sulfonamide;

N-{[6-(Carbamoylamino)-4-(methylthio)pyridin-2-yl]carbamoyl}-5-(2-methoxyethyl)-4-methylthiophene-2-sulfonamide;

5-(2-Methoxyethyl)-N-[(4-methoxy-6-{[(methylamino)carbonothioyl]amino}pyridin-2-yl)carbamoyl]-4-methylthiophene-2-sulfonamide;

N-{[6-(Carbamoylamino)-4-methoxypyridin-2-yl]carbamoyl}-5-(2-methoxyethyl)-4-methylthiophene-2-sulfonamide;

7-Methoxy-N-({4-methoxy-6-[(methylcarbamoyl)amino]pyridin-2-yl}carbamoyl)-1-methyl-1H-indole-3-sulfonamide;

N-({6-[(2-Fluoroethyl)amino]-4-(methylthio)pyridin-2-yl}carbamoyl)-5-(2-methoxyethyl)-4-methylthiophene-2-sulfonamide;

N-{[6-Amino-5-fluoro-4-(trifluoromethyl)pyridin-2-yl]carbamoyl}-5-(2-methoxyethyl)-4-methylthiophene-2-sulfonamide;

2-{5-[({[6-Amino-5-fluoro-4-(trifluoromethyl)pyridin-2-yl]carbamoyl}amino)sulfonyl]-3-methyl-2-thienyl}ethyl acetate;

N-{[6-Amino-5-fluoro-4-(trifluoromethyl)pyridin-2-yl]carbamoyl}-5-(2-hydroxyethyl)-4-methylthiophene-2-sulfonamide;

5-(2-Methoxyethyl)-4-methyl-N-{[6-methyl-4-(methylthio)pyridin-2-yl]carbamoyl}thiophene-2-sulfonamide;

5-(2-methoxyethyl)-4-methyl-N-{[6-methyl-4-(trifluoromethyl)pyridin-2-yl]carbamoyl}thiophene-2-sulfonamide;

2-{3-methyl-5-[({[6-methyl-4-(trifluoromethyl)pyridin-2-yl]carbamoyl}amino)sulfonyl]-2-thienyl}ethyl acetate;

5-(2-Hydroxyethyl)-4-methyl-N-{[6-methyl-4-(trifluoromethyl)pyridin-2-yl]carbamoyl}thiophene-2-sulfonamide and 5-Methyl-N-{[6-methyl-4-(trifluoromethyl)pyridin-2-yl]carbamoyl}thiophene-3-sulfonamide.

Processes for the manufacture of compounds of formula I are an object of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

Compounds of formula I can be prepared as shown in in Schemes 1-2 and in the preparative examples 1-122. The starting material of formula II are known compounds or may be prepared by methods well known in the art.

Sulfonic acid amide derivatives III were mainly prepared by approaches described in Scheme 1. An aryl or heteroaryl sulfonyl chloride derivative II was converted to a sulfonic acid amide derivative following reaction with ammonia. The sulfonic acid amide derivative III was reacted with phenyl chloroformate IV in the presence of triethylamine to prepare the carbamate derivative V, which in turn was then reacted with the pyridine derivative VI to yield compounds of type I.

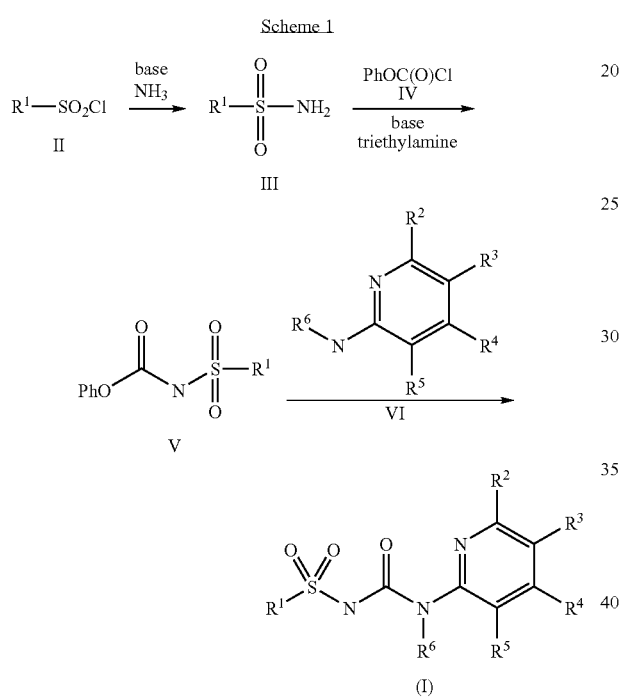

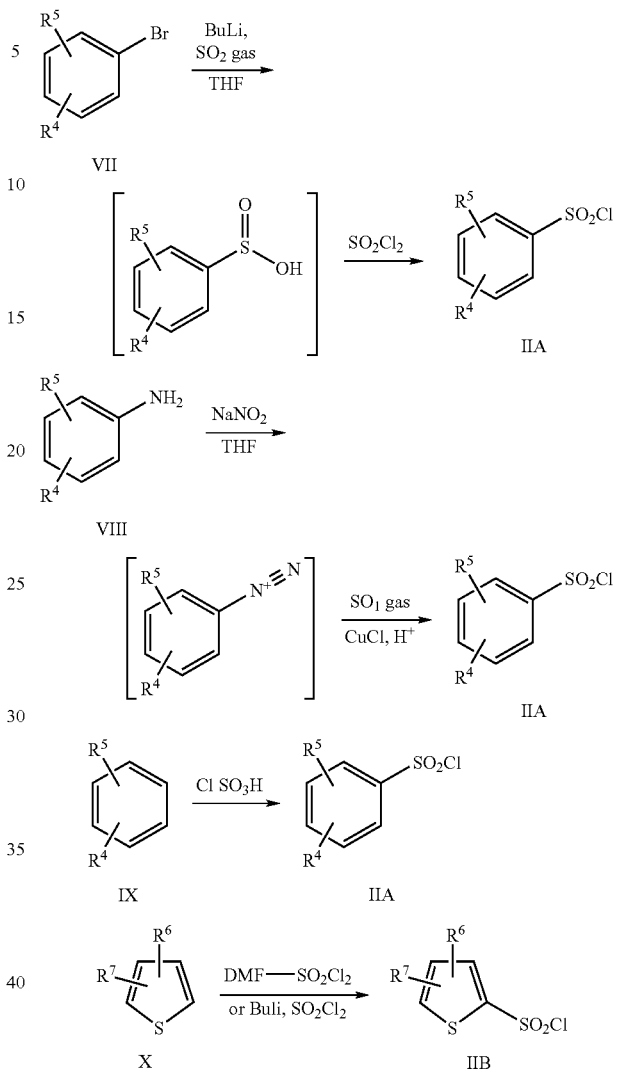

Sulfonyl chlorides IIA, for example phenyl sulfonyl chlorides, were prepared from the corresponding bromide VII by first, lithium halogen exchange at low temperature in an inert solvent such as THF, and trapping the lithiated species with $SO_2$ gas. The resultant intermediate was reacted with a chlorinating reagent such as sulfuryl chloride or N-chlorosuccinimide to prepare IIA. Alternatively, an aryl amine VIII underwent diazotisation with sodium nitrite. The diazonium salt intermediate, in the presence of $SO_2$ gas, copper (I) chloride and in an acidic solution, underwent the *Meerwein* reaction to yield IIA. A third method employed was the direct reaction of activated phenyl IX with chlorosulfonic acid. Thiophene sulfonyl chlorides IIB were prepared from thiophene precursors X by reacting with a preformed $DMF-SO_2Cl_2$ complex. In another variant, such thiophene derivatives X are treated with $SO_3$-DMF complex and the resultant sulfonic acids transformed into the corresponding sulfochlorides, e.g., by reacting them at elevated temperature with $SOCl_2$ or oxalyl chloride. Alternatively, lithiation with butyl lithium at low temperature and subsequent reaction with sulfuryl chloride also furnished compounds of type IIB (Scheme 2).

A preferred process for the preparation of a compound of formula

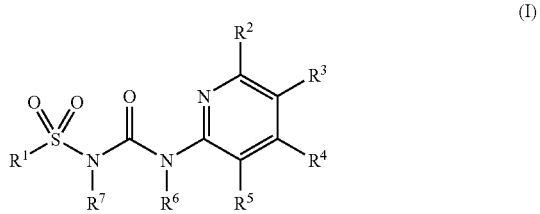

as described before comprises one of the following reactions, wherein $R^1$ to $R^7$ are defined as before a) reaction of a compound according to formula II

in the presence of a base, preferably ammonia, in order to obtain a compound of formula III;

b) reacting a compound of formula III

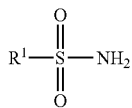

in the presence of a base, preferably triethylamine, with a compound of formula IV PhOC(O)Cl, in order to obtain a compound of formula V

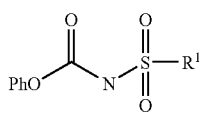

c) reacting a compound of formula V with a compound of formula VI,

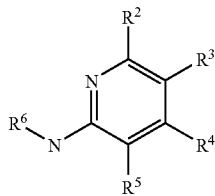

in order to obtain a compound of formula I

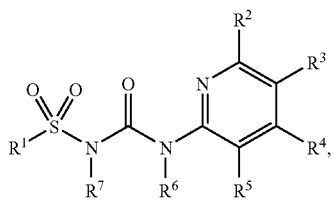

The compounds of formula I as described above for use as therapeutically active substance are a further object of the invention.

A further object of the invention are the compounds according to formula I for the preparation of medicaments for the prophylaxis and/or therapy of illnesses which are caused by disorders associated with the enzyme Fructose-1,6-bisphosphatase, preferably Diabetes Mellitus Type II, Diabetes Mellitus Type I, Diabetes Mellitus Type III, Impaired Fasting Glucose (IFG), Impaired Glucose Tolerance (IGT), diabetic complications or ischaemia.

Likewise preferred is a pharmaceutical composition comprising a compound of formula I as described and a therapeutically inert carrier.

A further preferred embodiment of the invention is the use of a compound according to formula I as described for the preparation of medicaments for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia and particularly preferred for the treatment and/or prophylaxis of Diabetes Mellitus Type II or Diabetes Mellitus Type I.

A further object of the present invention is a compound according to formula I, when manufactured according to any one of the described processes.

Likewise preferred is a method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, which method comprises administering an effective amount of a compound of formula I as described. Preferred is this method for the treatment and/or prophylaxis of Diabetes Mellitus Type II or Diabetes Mellitus Type I.

Assay Procedures

FBPase Assay Description:

The following tests were carried out for evaluating the inhibitory activity of the compounds of the present invention against human liver FBPase (Swissprot Data base reference PO9467, entry F16P_HUMAN).

Enzyme Preparation:

Human liver FBPase cDNA (NM_000507) was purchased from Origene Technologies, Inc, subcloned in a vector for expression in $E.$ $Coli.$, and sequenced. Recombinant human liver FBPase (hlFBPase) was purified according to the following protocol that uses heat denaturation similarly to that described by El-Maghrabi et al. [El-Maghrabi, M. R. et al. "Isolation of a human liver fructose-1,6-bisphosphatase cDNA and expression of the protein in $Escherichia$ $coli$." J Biol Chem 268:9466-9472, 1993.]. Briefly, $E.$ $coli$ cells, transiently expressing very high levels of soluble and active human liver FBPase, were suspended in 20 mM Tris-HCl pH 7.5, 1 mM EDTA, 1 mM DTT and were lysed by French press. The soluble extract was heat denatured at 65° C. for 5 min, and insoluble, denatured proteins were removed by centrifugation. The extract was then applied to a BioRad Macro-Prep High Q column equilibrated with 20 mM Tris-HCl pH 7.5, 1 mM EDTA, 1 mM DTT and the flow-through (containing FBPase activity) was collected and applied to a BioRad Macro-Prep HS column equilibrated with 20 mM HEPES pH 7.2, 1 mM DTT. A gradient of increasing NaCl concentration was then applied to the HS column and fractions were collected. Fractions containing active FBPase were pooled and further purified by size exclusion chromatography on a Sephacryl S200 column equilibrated in 20 mM Tris-HCl pH 7.5, 150 mM NaCl, 1 mM EDTA, 1 mM DTT. Purity of the enzyme preparation was >90% as assessed by Mass spectrometry.

In vitro Activity:

Recombinant human liver FBPase (hlFBPase) activity was assayed through measuring the inorganic phosphate release that results from the hydrolysis of Fructose-1,6-bisphosphate by the enzyme. As described by Baykov A. A. et al. in [Baykov A. A et al., "Malachite Green procedure for orthophosphate determination and its use in alkaline phosphatase-based enzyme immunoassays". Anal. Biochem., 171:266-270, 1988], inorganic phosphate can be readily quantified by spectrophotometry at 620 nm after complexation with ammonium molybdate/malachite green reagent. Enzymatic reaction was carried out with modifications of the procedure described by Wright S. W. et al. [Wright S. W. et al., "Anilinoquinazoline inhibitors of Fructose-1,6-bisphosphatase bind to a novel allosteric site: synthesis, in vitro characterization, and X-ray crystallography". J. Med. Chem. 45:3865-

3877, 2002]. Specifically, the reaction was carried out in 96 well plates in a final volume of 100 µl in the presence or in the absence of allosteric inhibitors. Reaction was started adding 25 ng of hlFBPase to the reaction mixture containing 50 mM HEPES-KOH buffer pH 7.2, 2 mM $MgCl_2$, 2 mM EDTA, 1 mM DTT, 50 µM fructose-1,6-bisphosphate and 1% DMSO. After 50 minutes incubation at room temperature, the phosphate released was allowed to form a colored complex for 10 min by adding 150 µl of ammonium molybdate/malachite green reagent containing 0.03% malachite green, 0.2% ammonium molybdate, 0.05% Triton X-100 and 0.7 M $H_2SO_4$ in water that was stirred for 30 min at room temperature and filtered through 0.2 µm filter. Under these conditions, the assay was linear with time and able to detect FBPase inhibition after spectrophotometric read-out at 620 nm.

Results obtained in the assay above using representative compounds of the invention as the test compounds are shown in the following table:

| Compound | FBPase assay $IC_{50}$(uM) |
|---|---|
| 1 | 0.058 |
| 2 | 0.072 |
| 3 | 0.059 |
| 4 | 0.063 |
| 5 | 0.066 |
| 6 | 0.079 |
| 7 | 0.1 |
| 8 | 0.105 |
| 9 | 0.115 |
| 10 | 0.125 |
| 11 | 0.132 |
| 12 | 0.132 |
| 13 | 0.148 |
| 14 | 0.167 |
| 15 | 0.175 |
| 16 | 0.096 |
| 17 | 0.185 |
| 18 | 0.185 |
| 19 | 0.201 |
| 20 | 0.223 |
| 21 | 0.225 |
| 22 | 0.23 |
| 23 | 0.242 |
| 24 | 0.259 |
| 25 | 0.26 |
| 26 | 0.312 |
| 27 | 0.351 |
| 28 | 0.396 |
| 29 | 0.42 |
| 30 | 0.428 |
| 31 | 0.429 |
| 32 | 0.433 |
| 33 | 1.657 |
| 34 | 0.481 |
| 35 | 0.494 |
| 36 | 0.566 |
| 37 | 0.574 |
| 38 | 0.582 |
| 39 | 0.61 |
| 40 | 0.631 |
| 41 | 0.696 |
| 42 | 0.76 |
| 43 | 0.834 |
| 44 | 0.864 |
| 45 | 0.866 |
| 46 | 0.937 |
| 47 | 1.022 |
| 48 | 1.023 |
| 49 | 1.06 |
| 50 | 1.089 |
| 51 | 1.11 |
| 52 | 1.47 |
| 53 | 1.478 |
| 54 | 1.523 |
| 55 | 1.554 |
| 56 | 1.725 |
| 57 | 1.772 |
| 58 | 1.965 |
| 59 | 2.032 |
| 60 | 2.066 |
| 61 | 2.068 |
| 62 | 2.122 |
| 63 | 2.171 |
| 64 | 2.185 |
| 65 | 2.21 |
| 66 | 2.351 |
| 67 | 2.507 |
| 68 | 3.046 |
| 69 | 3.07 |
| 70 | 3.434 |
| 71 | 4.03 |
| 72 | 4.604 |
| 73 | 1.74 |
| 74 | 2.26 |
| 75 | 1.694 |
| 76 | n.d. |
| 77 | 0.809 |
| 78 | 0.906 |
| 79 | 0.558 |
| 80 | 1.61 |
| 81 | 0.665 |
| 82 | 1.87 |
| 83 | 5.23 |
| 84 | 0.429 |
| 85 | 0.756 |
| 86 | 1.779 |
| 87 | 4.76 |
| 88 | 55.439 |
| 89 | 0.5 |
| 90 | 1.061 |
| 91 | 2.162 |
| 92 | 1.611 |
| 93 | 0.844 |
| 94 | 1.6 |
| 95 | 5.08 |
| 96 | 0.527 |
| 97 | 0.278 |
| 98 | 2.288 |
| 99 | 0.92 |
| 100 | 3.41 |
| 101 | >100 |
| 102 | 42 |
| 103 | 5.7 |
| 104 | >100 |
| 105 | 2.615 |
| 106 | 1.496 |
| 107 | 2.55 |
| 108 | 16 |
| 109 | 1.87 |
| 110 | 16.4 |
| 111 | 0.345 |
| 112 | 0.8 |
| 113 | 0.84 |
| 114 | 0.515 |
| 115 | 2.78 |
| 116 | 1.48 |
| 117 | 1.63 |
| 118 | 2.3 |
| 119 | 4.8 |
| 120 | 0.831 |
| 121 | 1.173 |
| 122 | 0.73 |

Compounds as described above have $IC_{50}$ values of 100 µM to 50 nM; preferred compounds have $IC_{50}$ values of 1000 to 50 nM. More preferred compounds have $IC_{50}$ values of 200 to 50 nM. These results have been obtained by using the foregoing test.

In vivo Activity:

Glucose lowering activity of representative compounds of the present invention was demonstrated after acute treatment in male adult and diabetic db/db mice. db/db mice (12-20 weeks of age) were purchased from Jackson laboratories and time-course effect of compounds on blood glucose levels was measured from tail vein samplings using fluorometric method (Glucotrend systems (Roche A G)).

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays), as aerosol formulations or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragees and hard gelatin capsules. Lactose, corn starch or derivatives thereof, talc, stearic acid or its salts etc. can be used, for example, as such adjuvants for tablets, dragees and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used e.g. for the prophylaxis and/or treatment of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia. The dosage can vary in wide limits and will, of course, be fitted to the individual requirements in each particular case. In general, in the case of oral administration a daily dosage of about 0.1 mg to 100 mg per kg body weight, preferably about 0.5 mg to 10 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

5-Chloro-N-({4-methoxy-6-[(methylcarbamoyl)amino]pyridin-2-yl}carbamoyl)-1-benzothiophene-2-sulfonamide To a suspension of 5-chloro-benzo[b]thiophene-2-sulfonic acid amide (cf. Example 1a, 0.08 g, 0.32 mmol) in acetonitrile (3 mL) was added triethyamine (0.11 mL, 0.8 mmol) and, at 0-5° C., phenylchloroformate (0.061 g, 0.40 mmol). The mixture was stirred at rt for 2 h, and 1-(6-amino-4-methoxy-pyridin-2-yl)-3-methyl-urea (cf. Example 1b, 0.095 g, 0.52 mmol) was added. The reaction mixture was stirred at 55-60° C. for 3 h. After cooling to rt the solution was chromatographed directly over silica gel using dichloromethane/methanol as eluent. The compound containing fractions were evaporated. The crude compound was dissolved in a mixture of THF/methanol 1:1 (100 mL) and treated briefly with Amberlite IR-120 (H$^+$). After filtration the filtrate was concentrated to obtain the title compound (0.066 g) as a colorless solid. MS (ISN): m/e 468.3, 470.1 (M−H)$^+$ 1 a) 5-Chloro-benzo[b]thiophene-2-sulfonic acid amide To a solution of 5-chloro-benzo[b]thiophene-2-sulfonyl chloride (Komoriya, Satoshi; Haginoya, Noriyasu, Bioorganic & Medicinal Chemistry (2005), 13(12), 3927-3954; 0.57 g, 2.1 mmol) in THF (8.0 mL) was added ammonia gas until saturation at ca. 10° C., then the flask was stoppered, and the reaction mixture was stirred at rt for 4 h. The reaction mixture was then quenched with water; the organic solvent was slowly evaporated under vacuum. The precipitate formed was filtered off, washed with water and dried over $P_2O_5$ under high vacuum to obtain the desired compound (0.52 g) as a white solid.

MS (ISN): m/e 246.1 (M−H)$^-$ 1 b) 1-(6-Amino-4-methoxy-pyridin-2-yl)-3-methyl-urea To a solution of 4-methoxy-2,6-diaminopyridine (AKos, CAS: 18960-98-0, 0.20 g, 1.44 mmol) in acetonitrile (4.0 mL) was added 1,1-carbonyidi-(1,2,4-triazole) (Fluka, 21861; 0.248 g, 01.51 mmol). The reaction mixture was stirred at rt for 1 h. A methylamine solution (33% in EtOH, 1.78 mL, 14.3 mmol) was added, and the mixture was stirred overnight at rt, quenched with ice/water, and extracted with ethyl acetate. The organics were washed with brine, dried and concentrated. The residue was triturated with ether, the crystals were filtered off, washed with ether and dried to obtain the desired compound (0.183 g) as a colorless solid.

MS (ISP): m/e 197.1 (M+H)$^+$

Example 2

N-{[4-Bromo-6-(carbamoylamino)pyridin-2-yl]carbamoyl}-5-methylthiophene-3-sulfonamide To a solution of 0.089 g 5-methyl-thiophene-3-sulfonic acid amide in 4 ml acetonitrile was added at 0° C. 0.094 g phenylchloroformate and 0.127 g triethylamine. The mixture was stirred at 0° C. for 1 h. To the resulting suspension was added 0.127 g (6-amino-4-bromo-pyridin-2-yl)-urea and the mixture was heated to 60° C. for 18 h. The mixture was cooled to room temperature. The product was collected by filtration, washed with acetonitrile and dried to constant weight to yield 0.190 g of the title compound as white crystals.

MS (ISN) M−H$^+$=431.9 and 433.9

2a) 5-Methyl-thiophene-3-sulfonic acid amide

To a solution of 12.0 g 4-bromo-2-methyl-thiophene in ml of diethyl ether was added drop wise 35.88 ml tert-butyl-lithium in pentane at −78° C. The mixture was stirred at −78°

C. for 15 min. To the resulting suspension was added drop wise ca 20 ml liquid sulfur dioxide at −78° C. The mixture was stirred at −78° C. for 15 min and then allowed to taw to room temperature. The solid was collected by filtration and dissolved in ca 20 ml water. To the resulting clear solution was added 8.895 g sodium acetate and 11.497 g hydroxylamine-O-sulfonic acid and the mixture was stirred at room temperature for 1 h whereby precipitation occurred. The solid was collected by filtration, washed with water and dried to constant weight to yield 8.47 g of the title compound as white solid melting at 102-104.3° C.

2b) (6-Amino-4-bromo-pyridin-2-yl)-urea

To a solution of 0.188 g 2.6-diamino-4-bromopyridine in 2 ml acetonitrile was added 0.164 g 1,1-carbonyldi(1,2,4-triazole) and the mixture was stirred at room temperature. After a short period of a clear solution a suspension formed. The mixture was stirred at room temperature for 1 h. To the resulting suspension was added 0.5 ml of a 25% aqueous ammonia solution and the resulting solution was stirred at room temperature for 0.5 h. The mixture was partitioned between water and ethyl acetate. The organic phase was separated and evaporated to dryness. The residue was taken up in methanol whereby crystallisation occurred. The crystals were collected by filtration and dried to constant weight to yield 0.068 g of the title compound as white crystals.
MS (ISP) M+H$^+$=231.0; 232.9

Example 3

N-({4-bromo-6-[(methylcarbamoyl)amino]pyridin-2-yl}carbamoyl)-5-methylthiophene-3-sulfonamide To a solution of 0.089 g 5-methyl-thiophene-3-sulfonic acid amide (example 2a) in 4 ml acetonitrile was added at 0° C. 0.094 g phenylchloroformate and 0.127 g triethylamine. The mixture was stirred at 0° C. for 1 h. To the resulting suspension was added 0.127 g 1-(6-amino-4-bromo-pyridin-2-yl)-3-methyl-urea and the mixture was heated to 60° C. for 18 h. The reaction mixture was partitioned between water and ethyl acetate. The phases were separated and the pH of the aqueous phase was adjusted to 2 by addition of 1N hydrochloric acid. The product was extracted with ethyl acetate. The organic phase was washed with water and brine, dried over sodium sulfate and evaporated to yield 0.080 g of the title compound as an orange yellow powder. MS (ISN) M−H$^+$= 445.8 and 447.7

3a) 1-(6-Amino-4-bromo-pyridin-2-yl)-3-methyl-urea

To a solution of 0.188 g 2.6-diamino-4-bromopyridine in 2 ml acetonitrile was added 0.164 g 1,1-carbonyldi(1,2,4-triazole) and the mixture was stirred at room temperature. After a short period of a clear solution a suspension formed. The mixture was stirred at room temperature for 1 h. To the resulting suspension was added 0.5 ml of a methylamine solution in THF (ca 3 M) and the resulting solution was stirred at room temperature for 0.5 h. The mixture was partitioned between water and ethyl acetate. The phases were separated and the organic phase evaporated to dryness. The residue was taken up in methanol whereby crystallisation occurred. The crystals were collected by filtration and dried to constant weight to yield 0.196 g of the title compound as white crystals. MS (ISP) M+H$^+$243.3; 245.2

Example 4

N-{[4-Bromo-4-(carbamoylamino)pyridin-2-yl]carbamoyl}-5-(2-methoxyethyl)-4-methylthiophene-2-sulfonamide To a solution of 0.050 g 5-(2-methoxy-ethyl)-4-methyl-thiophene-2-sulfonic acid amide in 1 ml acetonitrile was added at 0° C. 0.040 g phenylchloroformate and 0.054 g triethylamine. The mixture was stirred at 0° C. for 1 h. To the resulting suspension was added 0.054 g (6-amino-4-bromo-pyridin-2-yl)-urea (example 2a) and the mixture was heated to 60° C. for 18 h. The reaction mixture was partitioned between 0.1 M sodium hydroxide and ethyl acetate. The phases were separated and the pH of the aqueous phase was adjusted to 2 by addition of 1.0 N hydrochloric acid and the product was extracted with ethyl acetate. The phases were separated and the organic phase was evaporated. The residue was triturated with methanol and the solid was collected by filtration to yield 0.022 g of the title compound as white solid. MS (ISN) M−H$^+$=492.2 and 490.2

4a) 2-(2-Methoxy-ethyl)-3-methyl-thiophene

A part of a solution containing 2-bromo-3-methylthiophene CAS 14282-76-9 (1.5 g, 8.5 mmol) in dry diethyl ether was added drop-wise to a suspension of magnesium (308 mg, 12.7 mmol, 1.5 equiv.) in dry diethyl ether, until the mixture started to reflux. The remaining solution was added dropwise. A solution of toluene-4-sulfonic acid 2-methoxy-ethyl ester (2.9 g, 12.7 mmol, 1.5 equiv.) in dry diethyl ether was added dropwise at room temp., then the mixture was refluxed for two hours. After cooling down to room temp., the mixture was quenched with ammonium chloride solution saturated and extracted with tert. butylmethyl ether. The combined organic extracts were washed with water and brine, dried over magnesiumsulfate-dihydrate and purified on silica gel with eluent n-heptane and tert.butylmethyl ether. The title compound was obtained as light yellow oil: 490 mg, GC-MS (EI) M=156.

4b) 5-(2-Methoxy-ethyl)-4-methyl-thiophene-2-sulfonyl chloride

Sulfuryl chloride (0.26 g, 1.9 mmol) was added drop wise to a stirred solution of dry DMF (0.14 ml, 1.9 mmol) at 0° C. under an argon atmosphere resulting in the formation of a white solid. After 15 min, 2-(2-methoxy-ethyl)-3-methyl-thiophene (250 mg, 1.6 mmol) was added and the mixture was warmed to 100° C. and the melt was further stirred for 45 min. Crushed ice was added and the reaction mixture was extracted with ethyl acetate (2×) and the combined organic extracts were washed with water, brine, dried (magnesium sulfate. dihydrate), filtered and concentrated under reduced pressure. The crude solid was purified over silica gel (ethyl acetate/n-heptane): light yellow oil, 220 mg, GC-MS (EI): M=254.

4c) 5-(2-Methoxy-ethyl)-4-methyl-thiophene-2-sulfonic acid amide

To a solution of 1.40 g (55 mM) 5-(2-methoxy-ethyl)-4-methyl-thiophene-2-sulfonyl chloride in 20 ml acetone was added 5 ml of an aqueous solution of ammonia (25%) and the mixture was stirred at room temperature for 1 h. The mixture was partitioned between water and ethyl acetate. The phases were separated and the organic phase was dried over sodium sulfate and evaporated. The residue purified by chromatography on silica gel crystallized form cyclohexane/diethyl ether to yield 0.89 g of the title compound as light red solid. MS (ISN) M−H$^+$=233.8

Example 5

5-Methoxy-N-({4-methoxy-6-[(methylcarbamoyl)amino]pyridin-2-yl}carbamoyl)-1-benzothiophene-3-sulfonamide The title compound was prepared in analogy to the procedure described in Example 1 starting from 5-methoxy-benzo[b]thiophene-3-sulfonic acid amide to obtain the desired compound as a creamy solid. MS (ISN): m/e 464.1 (M−H)$^-$

5 a) 5-Methoxy-benzo[b]thiophene-3-sulfonyl chloride

To a suspension of sulfur trioxide dimethylformamide complex (1.84 g, 8.12 mmol) in 1,2-dichloroethane (10 mL) was added 5-methoxy-benzo[b]thiophene (Marez-Silanes, S., J. Heterocycl. Chem. (2001), 38(6), 1469; 1.64 g, 10.0 mmol). The reaction mixture was stirred at rt for 1 h. Thionyl chloride (1.55 g, 13.08 mmol) was added, and the mixture was stirred at 70° C. for 1 h and chromatographed directly on silica gel using heptane/ethyl acetate or dichloromethane/ethyl acetate as eluents to obtain the desired compound(2.10 g) as yellowish solid. MS (EI): m/e 262.1 (H)

5 b) 5-Methoxy-benzo[b]thiophene-3-sulfonic acid amide

To a solution of 5-methoxy-benzo[b]thiophene-3-sulfonyl chloride(0.80 g, 3.08 mmol) in THF (20 mL) was added ammonia gas until saturation at ca. 10° C., then the flask was stoppered, and the reaction mixture was stirred at rt for 4 h. The reaction mixture was then quenched with water; the organic solvent was slowly evaporated under vacuum. The precipitate formed was filtered off, washed with water and dried over P$_2$O$_5$ under high vacuum to obtain the desired compound (0.64 g) as a yellowish solid. MS (ISN): m/e 239.4 (M−H)$^-$

Example 6

5-Isobutyl-N-({4-methoxy-6-[(methylcarbamoyl)amino]pyridin-2-yl}carbamoyl)-4-methylthiophene-2-sulfonamide In analogy to example 3, by replacing 1-(6-amino-4-bromo-pyridin-2-yl)-3-methyl-urea with 1-(6-amino-4-methoxy-pyridin-2-yl)-3-methyl-urea and 5-methyl-thiophene-3-sulfonic acid amide with 5-isobutyl-4-methyl-thiophene-2-sulfonic acid amide, the title compound was obtained as white solid. MS (ISN) M−H$^+$=454.3

6a) 5-Isobutyl-4-methyl-thiophene-2-sulfonic acid amide

To a mixture of 0.368 g of the complex of sulfur trioxide with dimethylformamide in 1.5 ml dichloromethane was added 0.309 g 2-isobutyl-3-methyl-thiophene and the mixture was heated to 55° C. for 30 min. and to 80° C. for an other 30 min. The mixture was cooled to room temperature and 0.286 g thionylchloride was added. The mixture was heated to 55° C. for ca 30 min cooled to room temperature and poored onto ice and extracted with ethyl acetate, the phases were separated and the organic phase was washed with water and brine and evaporated. The residue was taken up in 10 ml acetone and mixed with 1 ml 25% aqueous ammonia for ca 30 min. The reaction mixture was partitioned between water and ethyl acetate. The phases were separated and the organic phase was purified by chromatography on silica gel with ethyl acetate:heptane=1:3 to yield 0.16 g of the title compound as oil. MS (ISN) M−H$^+$=232.0

Example 7

N-({4-Methoxy-6-[(methylcarbamoyl)amino]pyridin-2-yl}carbamoyl)-5-methyl-1-benzothiophene-2-sulfonamide The title compound was prepared in analogy to the procedure described in Example 1 starting from 5-methyl-benzo[b]thiophene-2-sulfonamide (Mader, Mary Margaret; Martin-Cabrejas, Luisa Maria; Richett, Michael Enrico, WO2004048329) to obtain the desired compound as a white solid. MS (ISN): m/e 447.9 (M−H)$^-$

Example 8

N-({4-Bromo-6-[(methylcarbamoyl)amino]pyridin-2-yl}carbamoyl)-5-(2-methoxyethyl)-4-methylthiophene-2-sulfonamide In analogy to example 3, by replacing 5-methyl-thiophene-3-sulfonic acid amide with 5-(2-methoxy-ethyl)-4-methyl-thiophene-2-sulfonic acid amide, the title compound was obtained as white crystals. MS (ISN) M−H$^+$=506.2 and 504.1

Example 9

N-[[[4-methoxy-6-[[(methylamino)carbonyl]amino]-2-pyridinyl]amino]carbonyl]-5-methyl-3-thiophene-sulfonamide In analogy to example 3, by replacing 1-(6-amino-4-bromo-pyridin-2-yl)-3-methyl-urea with 1-(6-amino-4-methoxy-pyridin-2-yl)-3-methyl-urea, the title compound was obtained as white crystals. MS (ISN) M−H$^+$=5062 and 504.1

9a) 1-(6-Amino-4-methoxy-pyridin-2-yl)-3-methyl-urea

In analogy to example 3a, by replacing 2.6-diamino-4-bromopyridine with 2.6-diamino-4-methoxypyridine, the title compound was obtained as white crystals. MS (ISP) M+H$^+$=197.1

Example 10

N-[(6-Amino-4-bromopyridin-2-yl)carbamoyl]-5-(2-methoxyethyl)-4-methylthiophene-2-sulfonamide In analogy to example 4, by replacing (6-amino-4-bromo-pyridin-2-yl)-urea with 2.6-diamino-4-bromopyridine the title compound was obtained as white solid. MS (ISN) M−H$^+$= 447.0

Example 11

N-[(6-Amino-4-bromopyridin-2-yl)carbamoyl]-4-chloro-5-(2-methoxyethyl)thiophene-2-sulfonamide 4-Chloro-5-(2-methoxy-ethyl)-thiophene-2-sulfonyl chloride (73 mg) was dissolved in acetonitrile (1.5 mL), NaOCN (38 mg) and pyridine (130 mL) was added to the solution. The mixture was stirred for 4 h at 25° C. After that 4-bromo-pyridine-2,6-diamine (50 mg) was added to the mixture as solid. The resulting yellow suspension was stirred for 2 h at 25° C. The suspension was evaporated to dryness, dissolved in DMSO (1.5 mL) and purified with preparative HPLC. N-[(6-amino-4-bromopyridin-2-yl)carbamoyl]-4-chloro-5-(2-methoxyethyl)-thiophene-2-sulfonamide (21 mg, 16.8% yield) was obtained as amorphous white solid.
[M−H]⁻=468.9 (Cl- and Br-Isotopes)

Example 12

6-Methoxy-N-({4-methoxy-6-[(methylcarbamoyl) amino]pyridin-2-yl}carbamoyl)-1-benzothiophene-2-sulfonamide The title compound was prepared in analogy to the procedure described in Example 1 starting from 6-methoxy-benzo[b]thiophene-2-sulfonamide (Graham, Samuel L.; Shepard, Kenneth L.; Anderson, Paul S.; Baldwin, John J.; Best, Darryl B.; Christy, Marcia E.; Freedman, Mark B.; Gautheron, Pierre; Habecker, Charles N.; et al., J. Med. Chem. (1989) 32(12), 2548-54) to obtain the desired compound as a colourless solid. MS (ISN): m/e 464.3 (M−H)⁻

Example 13

5-Methoxy-N-({4-methoxy-6-[(methylcarbamoyl) amino]pyridin-2-yl}carbamoyl)-1-benzothiophene-2-sulfonamide The title compound was prepared in analogy to the procedure described in Example 1 starting from 5-methoxy-benzo[b]thiophene-2-sulfonamide (Graham, Samuel L.; Shepard, Kenneth L.; Anderson, Paul S.; Baldwin, John J.; Best, Darryl B.; Christy, Marcia E.; Freedman, Mark B.; Gautheron, Pierre; Habecker, Charles N.; et al., J. Med. Chem. (1989) 32(12), 2548-54) to obtain the desired compound as a colourless solid. MS (ISN): m/e 464.1 (M−H)⁻

Example 14

5-(2-Methoxyethyl)-4-methyl-N-({6-[(methylcarbamoyl)amino]-4-(methylthio)pyridin-2-yl}carbamoyl)thiophene-2-sulfonamide In analogy to example 8, by replacing 1-(6-amino-4-bromo-pyridin-2-yl)-3-methyl-urea with 1-(6-amino-4-methylsulfanyl-pyridin-2-yl)-3-methyl-urea, the title compound was obtained as white solid. MS (ISN) M−H⁺=472.0

14a) 1-(6-Amino-4-methylsulfanyl-pyridin-2-yl)-3-methyl-urea

In analogy to example 3a, by replacing 2.6-diamino-4-bromopyridine with 4-methylsulfanyl-pyridine-2,6-diamine, the title compound was obtained as white crystals. MS (ISP) M+H⁺=213.3

14b) and 14c) 4-Methylsulfanyl-pyridine-2,6-diamine and 6-Amino-4-methylsulfanyl-pyridin-2-ol A mixture of 4.00 g 2,6-dibromo-4-methylsulfanyl-pyridine and 100 ml 25% aqueous ammonia was heated in an autoclave to 140° C. for 36 h. The solvent was evaporated and the residue was purified by chromatography on silica gel with ethyl acetate to ethyl acetate:methanol=9:1 and crystallized from ethyl acetate to yield 0.993 g 4-methylsulfanyl-pyridine-2,6-diamine as off white crystals melting at 165-167° C. The more polar fractions were collected and crystallized from ethyl acetate to yield 0.276 g 6-amino-4-methylsulfanyl-pyridin-2-ol as brownish solid. MS (ISP) M+H⁺=157.1.

Example 15

N-({4-Bromo-6-[(2,2-difluoroethyl)amino]pyridin-2-yl}carbamoyl)-4-chloro-5-(2-methoxyethyl) thiophene-2-sulfonamide Example 15 was prepared in analogy to example 11 using 4-chloro-5-(2-methoxy-ethyl)-thiophene-2-sulfonyl chloride (62 mg) and 4-bromo-N-(2,2-difluoroethyl)-pyridine-2,6-diamine (41 mg). The crude product was purified with flash chromatography over silica gel (20 g SiO₂, gradient ethyl acetate/n-heptane 1:4→1:0) to yield N-({4-bromo-6-[(2,2-difluoroethyl)amino]pyridin-2-yl}carbamoyl)-4-chloro-5-(2-methoxyethyl)thiophene-2-sulfonamide (50 mg, 41%) as light brown solid.
[M−H]⁻=533.0 (Br-isotopes)

15a) 4-Bromo-N-(2,2-difluoro-ethyl)-pyridine-2,6-diamine

4-Bromo-pyridine-2,6-diamine (2.2 g) was dissolved under an argon atmosphere in THF (15 mL) and cooled to 0° C. At this temperature LiHMDS (12.9 mL 1 M solution in THF) was added slowly to the solution. The reaction mixture was stirred at 0° C. for 1 h. After that difluorethyltriflate (2.76 g) was added and the reaction mixture was stirred at 25° C. for 18 h. Complete conversion was observed by LC-MS analysis. The reaction mixture was evaporated to dryness, dissolved in ethyl acetate and extracted with water and brine. The organic layer was dried over Na₂SO₄, filtrated and evaporated to dryness. The crude product was purified by flash chromatography over silica gel (70 g SiO₂, gradient ethyl acetate/n-heptane 1:4->1:0) to yield 4-bromo-N-(2,2-difluoroethyl)-pyridine-2,6-diamine (0.943 g; 32%) as a dark red oil.

Example 16

5-Methyl-N-({6-[(methylcarbamoyl)amino]-4-(methylthio)pyridin-2-yl}carbamoyl)thiophene-3-sulfonamide In analogy to example 3, by replacing 1-(6-amino-4-bromo-pyridin-2-yl)-3-methyl-urea with 1-(6-Amino-4-methylsulfanyl-pyridin-2-yl)-3-methyl-urea, the title compound was obtained as white solid. MS (ISN) M−H⁺=414.3

Example 17

N-{[6-(Carbamoylamino)-4-(methylthio)pyridin-2-yl]carbamoyl}-5-(2-methoxyethyl)-4-methylthiophene-2-sulfonamide In analogy to example 4, by replacing (6-Amino-4-bromo-pyridin-2-yl)-urea with (6-amino-4-methylsulfanyl-pyridin-2-yl)-urea, the title compound was obtained as white solid. MS (ISN) M−H⁺=458.0

Example 18

5-(2-Methoxyethyl)-N-[(4-methoxy-6-{[(methylamino)carbonothioyl]amino}pyridin-2-yl)carbamoyl]-4-methylthiophene-2-sulfonamide In analogy to example 8, by replacing 1-(6-amino-4-bromo-pyridin-2-yl)-3-methyl-urea with 1-(6-amino-4-methoxy-pyridin-2-yl)-3-methyl-thiourea, the title compound was obtained as white solid. MS (ISN) M–H$^+$=471.9

18a) 1-(6-Amino-4-methoxy-pyridin-2-yl)-3-methyl-thiourea

In analogy to example 1b, by replacing 1,1-carbonyldi(1,2,4-triazole) with di-imidazol-1-yl-methanethione, the title compound was obtained as white crystals. MS (ISP) M+H$^+$=213.4

Example 19

N-({4-Bromo-6-[(2,2-difluoroethyl)amino]pyridin-2-yl}carbamoyl)-5-(2-methoxyethyl)-4-methylthiophene-2-sulfonamide Prepared in analogy to example 15 starting from 4-methyl-5-(2-methoxy-ethyl)-thiophene-2-sulfonyl chloride (80 mg) and 4-bromo-N-(2,2-difluoro-ethyl)-pyridine-2,6-diamine (58 mg) to yield N-({4-bromo-6-[(2,2-difluoroethyl)amino] pyridin-2-yl}carbamoyl)-5-(2-methoxyethyl)-4-methylthiophene-2-sulfonamide (39 mg, 24%) as light yellow solid. [M–H]$^-$=513.1 (Br-Isotopes)

Example 20

5-(2-Methoxyethyl)-N-({4-methoxy-6-[(methylcarbamoyl)amino]pyridin-2-yl}carbamoyl)-4-methylthiophene-2-sulfonamide In analogy to example 8, by replacing 1-(6-amino-4-bromo-pyridin-2-yl)-3-methyl-urea with 1-(6-amino-4-methoxy-pyridin-2-yl)-3-methyl-urea, the title compound was obtained as white solid. MS (ISN) M–H$^+$=456.5

Example 21

N-[(6-Amino-4-bromopyridin-2-yl)carbamoyl]-5-(methoxymethyl)-4-methylthiophene-2-sulfonamide In analogy to example 3, by replacing 1-(6-amino-4-bromo-pyridin-2-yl)-3-methyl-urea with 4-bromo-pyridine-2,6-diamine and 5-methyl-thiophene-3-sulfonic acid amide with 5-methoxymethyl-4-methyl-thiophene-2-sulfonic acid amide, the title compound was obtained as white solid. MS (ISN) M–H$^+$=433.0

21a) 2-Methoxymethyl-3-methyl-thiophene

To a solution of 7.3 g (3-methyl-thiophen-2-yl)-methanol in 65 ml tetrahydrofuran was added 2.73 g sodium hydride 55% in oil and the mixture was stirred at room temperature for 1 h. To ethe resulting mixture was added 4.3 ml iodomethane and the mixture was stirred at room temperature for 18 h. The reaction mixture was partitioned between aqueous potassium hydrogensulfate and ethyl acetate. The phases were separated and the organic phase was washed with water and brine dried over magnesium sulfate dehydrate and purified by distillation (13 mBar 160° C.) to yield 6.5 g of the title compound as light brown oil.

21b) 5-Methyl-thiophene-3-sulfonic acid amide

To a solution of 1.422 g 2-methoxymethyl-3-methyl-thiophene in 50 ml tetrahydrofurane was added drop wise at –78° C. 6.5 ml of a ca 1.6M solution of n-butyllithium in n-hexane and the mixture was stirred at this temperature for 50 min. Gaseous sulfur dioxide passed through the resulting solution for 40 min. and the mixture was diluted with 25 ml diethyl ether and warmed to room temperature. The solid was collected by filtration and taken up in 45 ml dichloromethane. The the resulting suspension was added 1.402 g N-chlorosuccinimide and the mixture was stirred at room temperature for 2 h. The reaction mixture was passed through a plug of speedex and the mother liquor was evaporated. The residue was taken up in 50 ml acetone and mixed with 20 ml 255 aqueous ammonia. The mixture was stirred at room temperature for 30 min. The reaction mixture was partitioned between water and ethyl acetate the phases were separated and the organic phase was purified by chromatography on silica gel with heptane: ethyl acetate to yield 0.910 g of the title compound as light yellow solid. MS (ISN) M–H$^+$=220.3

Example 22

N-{[6-(Carbamoylamino)-4-methoxypyridin-2-yl] carbamoyl}-5-methylthiophene-3-sulfonamide In analogy to example 2, by replacing 1-(6-amino-4-bromo-pyridin-2-yl)-3-methyl-urea with 1-(6-amino-4-methoxy-pyridin-2-yl)-3-methyl-urea, the title compound was obtained as white solid. MS (ISN) M–H$^+$=384.1

Example 23

N-({4-Cyano-6-[(methylcarbamoyl)amino]pyridin-2-yl}carbamoyl)-5-(2-methoxyethyl)-4-methylthiophene-2-sulfonamide In analogy to example 8, by replacing 1-(6-amino-4-bromo-pyridin-2-yl)-3-methyl-urea with 1-(6-amino-4-cyano-pyridin-2-yl)-3-methyl-urea, the title compound was obtained as white solid. MS (ISN) M–H$^+$=451.0

23a) 1-(6-Amino-4-cyano-pyridin-2-yl)-3-methyl-urea

In analogy to example 3a, by replacing 2.6-diamino-4-bromopyridine with 2.6-diamino-4-cyano-pyridine, the title compound was obtained as white solid. MS (ISP) M+H$^+$=192.3

23b) 2,6-Diamino-4-cyano-pyridine

A mixture of 1.00 g 2.6-diamino-4-bromopyridine and 0.992 g copper(I)cyanide in 10 ml dimethylformamide was heated under microwave irradiation to 230° C. for 1000 sec. The resulting mixture was partitioned between 10% aqueous ammonium chloride and ethyl acetate. The phases were separated and the aqueous phase was extracted with ethyl acetate. The organic phases were washed with water and brine, dried over magnesium sulfate dihydrate and evaporated. The solid residue was dissolved in hot ethyl acetate and passed through a filter. To the clear mother liquor was added heptane until crystallization started. The mixture was cooled to room temperature and the crystals were collected by filtration to yield 0.528 g of the title compound as yellowish solid.
MS (ISP) M+H$^+$=134.1

Example 24

N-{[6-(Carbamoylamino)-4-methoxypyridin-2-yl]carbamoyl}-5-(2-methoxyethyl)-4-methylthiophene-2-sulfonamide In analogy to example 4, by replacing (6-amino-4-bromo-pyridin-2-yl)-urea with 1-(6-amino-4-methoxy-pyridin-2-yl)-3-methyl-urea, the title compound was obtained as white solid. MS (ISN) M−H$^+$=442.0

Example 25

N-{[6-Bromo-4-(methylthio)pyridin-2-yl]carbamoyl}-5-(2-methoxyethyl)-4-methylthiophene-2-sulfonamide In analogy to example 4, by replacing (6-Amino-4-bromo-pyridin-2-yl)-urea with 6-bromo-4-methylsulfanyl-pyridin-2-ylamine, the title compound was obtained as white solid. MS (ISN) M−H$^+$=442.0

25a) 6-Bromo-4-methylsulfanyl-pyridin-2-ylamine

A mixture of 0.500 g 2,6-dibromo-4-methylsulfanyl-pyridine and 10 ml 25% aqueous ammonia was heated in an autoclave to 140° C. for 24 h. The solvent was evaporated and the residue was purified by chromatohraphy on silica gel with heptane:ethyl aceate=1:1 to yield 0.300 g of the title compound as white crystals. MS (ISP) M+H$^+$=219.1; 221.1

Example 26

7-Methoxy-N-({4-methoxy-6-[(methylcarbamoyl)amino]pyridin-2-yl}carbamoyl)-1-methyl-1H-indole-3-sulfonamide The title compound was prepared in analogy to the procedure described in Example 1 starting from 7-methoxy-1-methyl-1H-indole-3-sulfonic acid amide to obtain the desired compound as a colourless solid. MS (ISN): m/e 461.3(M−H)$^-$ 26 a) 7-Methoxy-1-methyl-1H-indole-3-sulfonyl chloride To a suspension of sulfur trioxide dimethylformamide complex (1.25 g, 8.12 mmol) in 1,2-dichloroethane (10 mL) was added 7-methoxy-1-methyl-1H-indole (Burgess, Walter J.; Jakas, Dalia; Huffman, William F.; Miller, William H.; Newlander, Kenneth A.; Seefeld, Mark A.; Uzinskas, Irene N., WO2003088897, 1.1 g, 6.9 mmol). The reaction mixture was stirred at rt for 1 h, thionyl chloride (1.055 g, 8.8 mmol) was added, and the mixture was stirred at 55-60° C. for 1 h and chromatographed directly on silica gel using heptane/ethyl acetate or dichloromethane/ethyl acetate as eluents to obtain 7-methoxy-1-methyl-1H-indole-3-sulfonyl chloride (0.81 g) as yellowish solid. MS (EI): m/e 259.1 (H)

26 b) 7-Methoxy-1-methyl-1H-indole-3-sulfonic acid amide

To a solution of 7-methoxy-1-methyl-1H-indole-3-sulfonyl chloride (0.80 g, 3.08 mmol) in THF (20 mL) was added ammonia gas until saturation at ca. 10° C., then the flask was stoppered, and the reaction mixture was stirred at rt for 4 h. The reaction mixture was then quenched with water, and the organic solvent was slowly evaporated under vacuum. The precipitate formed was filtered off, washed with water and dried over P$_2$O$_5$ under high vacuum to obtain the desired compound (0.64 g) as a yellowish solid. MS (ISN): m/e 239.4 (M−H)$^-$ Example 27

N-({4-Methoxy-6-[(methylcarbamoyl)amino]pyridin-2-yl}carbamoyl)-3-methylbenzenesulfonamide In analogy to example 20, by replacing 5-(2-methoxy-ethyl)-4-methyl-thiophene-2-sulfonic acid amide with m-tolylsulfonamide, the title compound was obtained as white solid. MS (ISN) M−H$^+$=392.4

Example 28

N-[(6-Amino-4-bromopyridin-2-yl)carbamoyl]-3-chlorobenzenesulfonamide

Example 28 was prepared in analogy to example 11 starting from 3-chlorophenylsulfonyl chloride (90 mg) and 4-bromo-pyridine-2,6-diamine (80 mg) to yield N-[(6-amino-4-bromopyridin-2-yl)carbamoyl]-3-chlorobenzenesulfonamide (46 mg, 27%) as a white solid.
[M−H]$^-$=405.1 (Cl- and Br-Isotopes)

Example 29

5-(Methoxymethyl)-N-({4-methoxy-6-[(methylcarbamoyl)amino]pyridin-2-yl}carbamoyl)thiophene-3-sulfonamide In analogy to example 20, by replacing 5-(2-methoxy-ethyl)4-methyl-thiophene-2-sulfonic acid amide with 5-methoxymethyl-thiophene-3-sulfonic acid amide, the title compound was obtained as white solid. MS (ISN) M−H$^+$=428.4

29a) 5-Methoxymethyl-thiophene-3-sulfonic acid amide

In analogy to example 2a, by replacing 4-bromo-2-methyl-thiophene with 4-bromo-2-methoxymethyl-thiophene, the title compound was obtained as white solid melting at 74.2-75.7° C.

Example 30

N-[(6-Amino-4-methoxypyridin-2-yl)carbamoyl]-5-(2-methoxyethyl)-4-methylthiophene-2-sulfonamide In analogy to example 4, by replacing (6-amino-4-bromo-pyridin-2-yl)-urea with 4-methoxy-pyridine-2,6-diamine, the title compound was obtained as white solid. MS (ISN) M−H$^+$=399.4

Example 31

N-[(4-Bromo-6-morpholin-4-ylpyridin-2-yl)carbamoyl]-5-(2-methoxyethyl)-4-methylthiophene-2-sulfonamide In analogy to example 15 starting from 4-methyl-5-(2-methoxy-ethyl)-thiophene-2-sulfonyl chloride (82 mg) and 4-bromo-6-morpholin-4-yl-pyridin-2-ylamine (61 mg) to yield N-[(4-bromo-6-morpholin-4-ylpyridin-2-yl)carbamoyl]-5-(2-methoxyethyl)-4-methyl-thiophene-2-sulfonamide (72 mg, 43%) as a yellow crystalline solid.

$[M-H]^-=519.3$ (Br-Isotopes)

31a) 4,6-Dibromo-1-oxy-pyridin-2-ylamine 2,4,6-Tribromo-1-oxy-pyridine (CAS 170875-37-3) (16 g) was suspended in aqueous $NH_4OH$ solution (25%; 162 g) in an autoclave and the mixture was stirred for 3 h at 80° C. at 3 bar pressure. The mixture was cooled in ice for 1 h, the obtained precipitate was filtered off, washed with ice water to yield 7.6 g crude material. The mother liquor was saturated with brine, turned to basic pH with aqueous NaOH (4N, 20 mL) and extracted twice with $CH_2Cl_2$. The combined organic layers were dried over $Na_2SO_4$, filtrated and evaporated to dryness to yield 2 g crude material. The combined 9.6 g crude material were dissolved in hot EtOAc (1 L), the volume was thereafter reduced to approx. 400 mL. The obtained crystals were filtered off and dried in vacuo. The mother liquor was purified with flash chromatography. Combination of the pure materials yielded 4,6-dibromo-1-oxy-pyridin-2-ylamine (7.2 g; 56%) as a crystalline light brown solid.

$[M+H]^+=266.9$ (2 Br-isotopes)

31b) 4-Bromo-6-morpholin-4-yl-1-oxy-pyridin-2-ylamine 4,6-Dibromo-1-oxy-pyridin-2-ylamine (4.57 g) and $K_2CO_3$ (3.54 g) were suspended in toluene (40 mL). Morpholine (4.46 g) was added to the mixture. The mixture was heated for 1 h at reflux. After that the reaction mixture was cooled to 25° C., diluted with water (40 mL) and stirred in an ice bath for 30 min. The obtained precipitate was filtered off, washed twice with water and dried in vacuo to yield 4-bromo-6-morpholin-4-yl-1-oxy-pyridin-2-ylamine (3.65 g; 78%) as light brown solid.

$[M+H]^+=274.0$ (Br-Isotopes)

31c) 4-Bromo-6-morpholin-4-yl-pyridin-2-ylamine

Under an argon atmosphere 4-bromo-6-morpholin-4-yl-1-oxy-pyridin-2-ylamine (274 mg) was dissolved in AcOH (3 mL) and iron powder (112 mg) was added. The mixture was heated for 1 h at 50° C., cooled to 25° C. and evaporated to dryness. The crude product was purified by flash chromatography (20 g $SiO_2$, $CH_2Cl_2$/MeOH->0-5%) to yield 4-bromo-6-morpholin-4-yl-pyridin-2-ylamine (184 mg; 71%) as a white crystalline solid.

$[M+H]^+=258.1$ (Br-isotopes)

Example 32

N-{[6-Amino-4-(methylthio)pyridin-2-yl]carbamoyl}-5-(2-methoxyethyl)-4-methylthiophene-2-sulfonamide In analogy to example 4, by replacing (6-Amino-4-bromopyridin-2-yl)-urea with 4-methylsulfanyl-pyridine-2,6-diamine, the title compound was obtained as white solid.

MS (ISN) $M-H^+=415.0$

Example 33

5-(2-Methoxyethyl)-4-methyl-N-{[4-(trifluoromethyl)pyridin-2-yl]carbamoyl}thiophene-2-sulfonamide In analogy to example 4, by replacing (6-Amino-4-bromopyridin-2-yl)-urea with 4-trifluoromethyl-pyridin-2-ylamine, the title compound was obtained as white solid. MS (ISN) $M-H^+=421.9$

Example 34

N-[(6-Amino-4-bromopyridin-2-yl)carbamoyl]-2,3-dihydro-1-benzofuran-5-sulfonamide Example 34 was prepared in analogy to example 11 starting from 2,3-dihydro-1-benzofuran-5-sulfonyl chloride (93 mg) and 4-bromo-pyridine-2,6-diamine (80 mg) to yield N-[(6-amino-4-bromopyridin-2-yl)carbamoyl]-2,3-dihydro-1-benzofuran-5-sulfonamide (39 mg, 22%) as a white solid.

$[M-H]^-=413.1$ (Br-isotopes)

Example 35

N-({4-Ethoxy-6-[(methylcarbamoyl)amino]pyridin-2-yl}carbamoyl)-5-(2-methoxyethyl)-4-methylthiophene-2-sulfonamide In analogy to example 4, by replacing (6-amino-4-bromopyridin-2-yl)-urea with 1-(6-amino-4-ethoxy-pyridin-2-yl)-3-methyl-urea, the title compound was obtained as white solid. MS (ISN) $M-H^+=470.1$

35a) 1-(6-Amino-4-ethoxy-pyridin-2-yl)-3-methylurea

In analogy to example 3a, by replacing 2.6-diamino-4-bromopyridine with 4-ethoxy-pyridine-2,6-diamine, the title compound was obtained as white solid. MS (ISP) $M+H^+=211.1$

Example 36

N-[(6-Amino-4-bromopyridin-2-yl)carbamoyl]-3-methylbenzenesulfonamide

Example 36 was prepared in analogy to example 11 starting from m-toluenesulfonyl chloride (81 mg) and 4-bromo-pyridine-2,6-diamine (80 mg) to yield N-[(6-amino-4-bromopyridin-2-yl)carbamoyl]-3-methylbenzenesulfonamide (53 mg, 32%) as a white solid.

$[M-H]^-=383.0$ (Br-Isotopes)

Example 37

N-[(6-Amino-4-bromopyridin-2-yl)carbamoyl]-2,3-dihydro-1,4-benzodioxine-6-sulfonamide Example 37 was prepared in analogy to example 11 starting from 2,3-dihydro-1,4-benzodioxine-6-sulfonyl chloride (100 mg) and 4-bromo-pyridine-2,6-diamine (80 mg) to yield N-[(6-amino-4-bromopyridin-2-yl)carbamoyl]-2,3-dihydro-1,4-benzodioxine-6-sulfonamide (32 mg, 17%) as a white solid.

$[M-H]^-=428.9$ (Br-isotopes)

Example 38

5-(2-Methoxyethoxy)-N-({4-methoxy-6-[(methylcarbamoyl)amino]pyridin-2-yl}carbamoyl)-4-methylthiophene-2-sulfonamide In analogy to example 20, by replacing 5-(2-methoxyethyl)-4-methyl-thiophene-2-sulfonic acid amide with 5-(2-methoxy-ethoxy)-4-methyl-thiophene-2-sulfonic acid amide, the title compound was obtained as white solid. MS (ISN) M−H+=472.5

Example 39

N-({4-Bromo-6-[(2,2-difluoroethyl)amino]pyridin-2-yl}carbamoyl)-3-methylbenzenesulfonamide Example 39 was prepared in analogy to example 15 starting from m-toluenesulfonyl chloride (80 mg) and 4-bromo-N-(2,2-difluoro-ethyl)-pyridine-2,6-diamine (77 mg) to yield N-({4-bromo-6-[(2,2-difluoroethyl)amino]pyridin-2-yl}carbamoyl)-3-methylbenzenesulfonamide (54 mg, 29%) as a light brown solid.
[M−H]−=449.0 (Br-isotopes)

Example 40

N-{[6-(Carbamoylamino)-4-ethoxypyridin-2-yl]carbamoyl}-5-(2-methoxyethyl)-4-methylthiophene-2-sulfonamide In analogy to example 4, by replacing (6-amino-4-bromopyridin-2-yl)-urea with (6-amino-4-ethoxy-pyridin-2-yl)-urea, the title compound was obtained as white solid.
MS (ISN) M−H+=456.0

40a) (6-Amino-4-ethoxy-pyridin-2-yl)-urea

In analogy to example 2b, by replacing 2.6-diamino-4-bromopyridine with 4-ethoxy-pyridine-2,6-diamine, the title compound was obtained as white solid. MS (ISP) M+H+=197.1

Example 41

N-({4-Bromo-6-[(2,2-difluoroethyl)amino]pyridin-2-yl}carbamoyl)-3-chlorobenzenesulfonamide Example 41 was prepared in analogy to example 15 starting from m-chlorophenylsulfonyl chloride (80 mg) and 4-bromo-N-(2,2-difluoro-ethyl)-pyridine-2,6-diamine (70 mg) to yield N-({4-bromo-6-[(2,2-difluoroethyl)amino]pyridin-2-yl}carbamoyl)-3-chlorobenzenesulfonamide (57 mg, 32%) as a light yellow solid.
[M−H]−=469.0 (Br, Cl-Isotopes)

Example 42

5-(2-Methoxyethyl)-4-methyl-N-({4-(trifluoromethyl)-6-[4-(trifluoromethyl)phenyl]pyridin-2-yl}carbamoyl)thiophene-2-sulfonamide Example 42 was prepared in analogy to example 15 starting from 4-methyl-5-(2-methoxy-ethyl)-thiophene-2-sulfonyl chloride (80 mg) and 4-trifluoromethyl-6-(4-trifluoromethyl-phenyl)-pyridin-2-ylamine (70 mg), whose synthesis is described below, to yield 5-(2-methoxyethyl)-4-methyl-N-({4-(trifluoromethyl)-6-[4-(trifluoromethyl)phenyl]pyridin-2-yl}carbamoyl)thiophene-2-sulfonamide (45 mg, 25%) as a white solid. [M−H]−=566.2

The starting materials were prepared as follows
A) General Procedure Ia

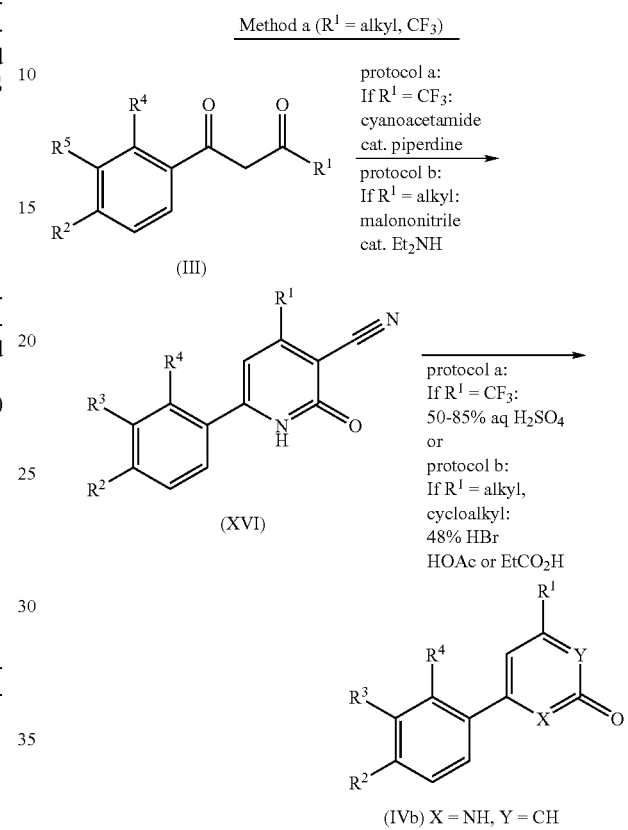

Method a (R$^1$=alkyl, CF$_3$):
Step 1 protocol a (R$^1$ is CF$_3$):

To a mixture of a 1,3-diketo-compound of formula III (wherein R$^1$ is CF$_3$; prepared as described under general procedure I step 1) and cyanoacetamide in a protic solvent (e.g. ethanol) is added at room temperature a catalytic amount (ca. 0.1 eq.) of piperidine and the mixture stirred at reflux temperature for 16 to 24 h. The reaction mixture is concentrated in vacuum, then treated with ice-water and acidified with 1M aqueous hydrochloric acid to achieve pH 1, the precipitate is filtered off, washed with water and dried in air at 60 to 70° C. to give the crude compounds of formula XVI, which can be used without further purification (according to Org. Prep. Proced. Int 1993, 25(1), 116-117).

2-Chloro-4-trifluoromethyl-6-(4-trifluoromethyl-phenyl)-pyridine 1) 2-Oxo-4-trifluoromethyl-6-(4-trifluoromethyl-phenyl)-1,2-dihydro-pyridine-3-carbonitrile:

The compound was prepared from commercially available ethyl trifluoroacetate, commercially available 4-trifluoromethyl-acetophenone and commercially available cyanoacetamide according to the general procedure I step 1 and Ia step 1. Obtained as a light yellow solid (69%). MS (ISN) 331 [(M−H)]; mp 197° C.

2) 4-Trifluoromethyl-6-(4-trifluoromethyl-phenyl)-1H-pyridin-2-one:

The compound was prepared from 2-oxo-4-trifluoromethyl-6-(4-trifluoromethyl-phenyl)-1,2-dihydro-pyridine-3-carbonitrile (42 g, 126 mmol) and 48% aqueous HBr in propionic acid according to general procedure Ia, step 2 protocol b. Obtained as a white solid (52.98 g, 88%). MS (ISP) 308.3 [(M+H)$^+$]; mp 203-204° C.

2-Bromo-4-trifluoromethyl-6-(4-trifluoromethyl-phenyl)-pyridine

The title compound was prepared from 4-trifluoromethyl-6-(4-trifluoromethyl-phenyl)-1H-pyridin-2-one (example A.17 step 2) (15 g, 49 mmol) and phosphoryl bromide (42 g, 146 mmol) according to the general procedure Ia to d preparation of bromides. Obtained as a brown solid (18 g, quant.). MS (EI) 368.9 [(M)$^+$] and 370.8 [(M+2)$^+$]; mp 35-37° C.

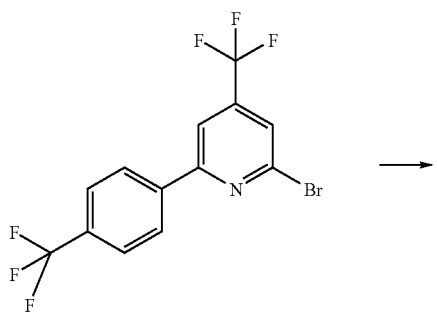

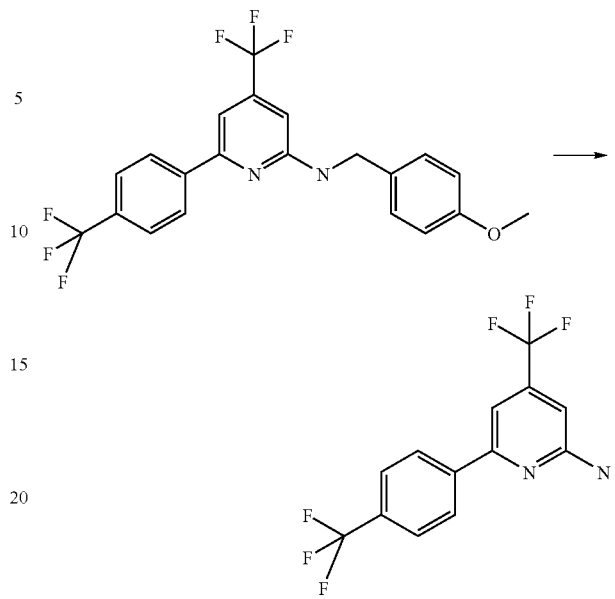

4-Trifluoromethyl-6-(4-trifluoromethyl-phenyl)-pyridin-2-ylamine

To (4-methoxy-benzyl)-[4-trifluoromethyl-6-(4-trifluoromethyl-phenyl)-pyridin-2-yl]-amine (6.4 g, 15 mmol) immersed in an icebath was added icecold conc. H$_2$SO$_4$ (30 mL) [immediate development of a deep red color!] and the mixture was stirred at 5° C. for 5 min, then the cooling bath was removed and stirring was continued at 23° C. for 2 h until all gummy material had dissolved into a clear deep red solution. Poured onto ice, made alkaline with 32% NaOH-sol., saturated with solid NaCl, extracted thrice with THF/TBME, dried over Na$_2$SO$_4$. Removal of the solvent in vacuum left the title compound as a light yellow solid (4.537 g, 99%). MS (ISP) 307.1 [(M+H)$^+$].

Example 43

N-{[6-Amino-4-(methylthio)pyridin-2-yl]carbamoyl}-5-methylthiophene-3-sulfonamide In analogy to example 2, by replacing (6-amino-4-bromopyridin-2-yl)-urea with 4-methylsulfanyl-pyridine-2,6-diamine, the title compound was obtained as white solid. MS (ISN) M−H$^+$=357.1

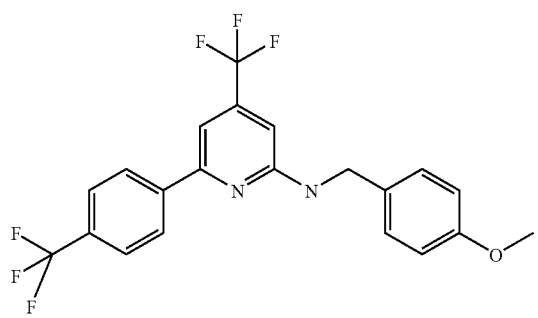

(4-Methoxy-benzyl)-[4-trifluoromethyl-6-(4-trifluoromethyl-phenyl)-pyridin-2-yl]-amine A mixture of 2-bromo-4-trifluoromethyl-6-(4-trifluoromethyl-phenyl)-pyridine (5.55 g, 15 mmol) and 4-methoxybenzylamine (5.9 mL, 45 mmol) in n-butanol (15 mL) was refluxed for 2 days. Evaporated to dryness, diluted with EtOAc, washed with 5% citric acid, sat. NaHCO$_3$-sol. and brine, dried over Na$_2$SO$_4$. Removal of the solvent in vacuum left the title compound as an orange oil (6.409 g, 100%). MS (ISP) 427.3 [(M+H)$^+$].

Example 44

N-[(6-Amino-4-bromopyridin-2-yl)carbamoyl]-5-(methoxymethyl)4-methylfuran-2-sulfonamide In analogy to example 3, by replacing 1-(6-amino-4-bromo-pyridin-2-yl)-3-methyl-urea with 4-bromo-pyridine-2,6-diamine and 5-methyl-thiophene-3-sulfonic acid amide with 5-methoxymethyl-4-methyl-furan-2-sulfonic acid amide, the title compound was obtained as white solid. MS (ISN) M−H$^+$=433.0

44a) 5-Methoxymethyl-4-methyl-furan-2-sulfonic acid amide

In analogy to the sequence in example 21 the title compound was obtained from (3-methyl-furan-2-yl)-methanol as beige solid. MS (ISN) M−H+=204.3

Example 45

N-({6-[(2-Fluoroethyl)amino]-4-(methylthio)pyridin-2-yl}carbamoyl)-5-(2-methoxyethyl)-4-methylthiophene-2-sulfonamide 5-(2-Methoxy-ethyl)-4-methyl-thiophene-2-sulfonic acid amide (0.063 g, 0.373 mmol) was dissolved in 2.2 mL of abs. acetonitrile and treated successively with phenyl chloroformate (0.058 g, 1.0 eq.) and triethylamine (0.129 mL, 2.5 eq.), and the mixture kept at ambient temperature for 1 h. The below prepared N-(2-fluoro-ethyl)-4-methylsulfanyl-pyridine-2,6-diamine (0.094 g, 1.0 eq.), dissolved in a tiny amount of acetonitrile, was then added, and the mixture heated to 60° C. for 18 h. Cooling, pouring onto crashed ice, twofold extraction with AcOEt, washing with water and brine, drying over sodium sulfate, and evaporation of the solvents, followed by flash chromatography (SiO$_2$, hexane/AcOEt=4/6) and crystallization from AcOEt, yielded eventually 0.041 g of the title compound as off-white crystals.
MS (ISP): 463.2 [M+H]+.
The Starting Materials were Prepared as Follows:

45a) 2.6-Dibromo-4-methylsulfanyl-pyridine

To a solution of 2,6-dibromo-4-nitro-pyridine (CAS 175422-04-5, 10.0 g, 35.5 mmol) in 60 mL of DMF was added at −10° C. sodium methanethiolate (2.61 g, 1.05 eq.) and the mixture stirred for 45 Min. at this temperature and for another 2 h at 0° C. Pouring onto crashed ice, twofold extraction with AcOEt, washing with water and brine, drying over magnesium sulfate, and evaporation of the solvents, followed by flash chromatography (SiO$_2$, hexane/AcOEt=97/3), yielded 8.55 g of the title compound as off-white crystals.
MS (ISP): 282.1 [M+H]+.

45b) 4-Methylsulfanyl-pyridine-2,6-diamine

The above prepared 2,6-dibromo-4-methylsulfanyl-pyridine (8.55 g, 30.2 mmol) was treated in the presence of copper powder (0.845 g) in a steel reactor with ammonia at 70 bar and 140° C. for 48 h. Ensuing flash chromatography (SiO$_2$, MeOH/AcOEt=1/9) afforded 5.35 g crude product which was extracted several times with AcOEt/2% MeOH. Evaporation of the combined organic extracts to dryness yielded 3.32 g of the title compound as brownish foam.
MS (ISP): 156.1 [M+H]+.

45c) N-(2-Fluoro-ethyl)-4-methylsulfanyl-pyridine-2,6-diamine

In a glass vessel were mixed together the above prepared 4-methylsulfanyl-pyridine-2,6-diamine (0.100 g, 0.644 mmol), 1-iodo-2-fluoroethane, 0.123 g, 1.10 eq.), and 1.2 eq. of Cs$_2$CO3 (0.252 g) in 1.0 mL of abs. acetonitrile, and the mixture allowed to react for 1 h at 125° C. in a microwave oven. Cooling, pouring onto crashed ice, twofold extraction with AcOEt, washing with water and brine, drying over sodium sulfate, and evaporation of the solvents, followed by flash chromatography (SiO$_2$, hexane/AcOEt=3/7) afforded 0.037 g of the title compound as brown solid.
MS (ISP): 202.1 [M+H]+.

Example 46

5-(2-Methoxyethyl)-4-methyl-N-{[4-methyl-6-(1,2,3,4-tetrahydronaphthalen-2-yl)pyridin-2-yl]carbamoyl}thiophene-2-sulfonamide Example 46 was prepared in analogy to example 15 starting from 4-methyl-5-(2-methoxy-ethyl)-thiophene-2-sulfonyl chloride (80 mg) and 4-Methyl-6-(1,2,3,4-tetrahydro-naphthalen-2-yl)-pyridin-2-ylamine (81 mg) to yield 5-(2-methoxyethyl)-4-methyl-N-{[4-methyl-6-(1,2,3,4-tetrahydronaphthalen-2-yl)pyridin-2-yl]carbamoyl}thiophene-2-sulfonamide (22 mg, 14%) as a yellow solid.
[M−H]−=498.3

46a) 4-Methyl-6-(1,2,3,4-tetrahydro-naphthalen-2-yl)-pyridin-2-ylamine 6-(3,4-Dihydro-naphthalen-2-yl)-4-methyl-pyridin-2-ylamine (CAS 521917-11-3) (1.8 g) is dissolved in methanol (30 mL) under an Ar atmosphere. To the obtained solution Pd/C (10%; 250 mg) was added. After that hydrogen was flushed through the reaction mixture (1 bar) for 2 h at 25° C. After that the catalyst was removed by filtration, the filtrate was evaporated to dryness and the crude product was purified by flash chromatography (200 g SiO$_2$, CH$_2$Cl$_2$/1% MeOH) to yield 4-methyl-6-(1,2,3,4-tetrahydro-naphthalen-2-yl)-pyridin-2-ylamine (970 mg) as an oil.
[M+H]+=239.3

Example 47

N-({4-Bromo-6-[(2,2-difluoroethyl)amino]pyridin-2-yl}carbamoyl)-2,3-dihydro-1-benzofuran-5-sulfonamide Example 47 was prepared in analogy to example 15 starting from 2,3-dihydro-1-benzofuran-5-sulfonyl chloride (80 mg) and 4-bromo-N-(2,2-difluoro-ethyl)-pyridine-2,6-diamine (70 mg) to yield N-({4-bromo-6-[(2,2-difluoroethyl)amino]pyridin-2-yl}carbamoyl)-2,3-dihydro-1-benzofuran-5-sulfonamide (25 mg, 14%) as a light brown solid.
[M−H]−=477.1 (Br-isotopes)

Example 48

N-({6-[(2-Hydroxyethyl)amino]-4-(methylthio)pyridin-2-yl}carbamoyl)-5-(2-methoxyethyl)-4-methylthiophene-2-sulfonamide The below prepared N-({6-[(2-(tert-butyl-dimethyl-silanyloxy)-ethyl)amino]-4-(methylthio)pyridin-2-yl}carbamoyl)-5-(2-methoxyethyl)-4-methylthiophene-2-sulfonamide (0.160 g, 0.278 mmol) was dissolved in 5 mL of MeOH and treated with aq. HCl (1.0 mL 1 N). After 2 h at ambient temperature, the reaction mixture was poured onto icewater, twofold extracted with AcOEt, washed with water and brine, dried over magnesium sulfate, and evaporated to dryness. Crystallization from AcOEt gave 0.081 g of the title compound as off-white crystals.
MS (ISP): 459.1 [M−H]−.

The Starting Materials were Obtaines as Follows:

48a) N-[2-(tert-Butyl-dimethyl-silanyloxy)-ethyl]-4-methylsulfanyl-pyridine-2,6-diamine In a glass vessel were mixed together the above prepared 4-methylsulfanyl-pyridine-2,6-diamine (0.350 g, 2.25 mmol), tert-butyl-(2-iodo-ethoxy)-dimethyl-silane (CAS 101166-65-8, 0.700 g, 1.08 eq.), and 1.2 eq. of $Cs_2CO3$ (0.882 g) in 3.5 mL of abs. acetonitrile, and the mixture allowed to react for 2 h at 125° C. in a microwave oven. Cooling, pouring onto crashed ice, twofold extraction with AcOEt, washing with water and brine, drying over sodium sulfate, and evaporation of the solvents, followed by flash chromatography ($SiO_2$, hexane/AcOEt=4/6) afforded 0.155 g of the title compound as light brown oil.
MS (ISP): 314.1 $[M+H]^+$.

48b) N-({6-[(2-(tert-Butyl-dimethyl-silanyloxy)-ethyl)amino]-4-(methylthio)pyridin-2-yl}carbamoyl)-5-(2-methoxyethyl)-4-methylthiophene-2-sulfonamide 5-(2-Methoxy-ethyl)-4-methyl-thiophene-2-sulfonic acid amide (0.082 g, 0.48 mmol) was dissolved in 2.8 mL of abs. acetonitrile and treated successively with phenyl chloroformate (0.075 g, 1.0 eq.) and triethylamine (0.167 mL, 2.5 eq.), and the mixture kept at ambient temperature for 1 h. The above prepared N-[2-(tert-butyl-dimethyl-silanyloxy)-ethyl]-4-methylsulfanyl-pyridine-2,6-diamine (0.150 g, 1.0 eq.), dissolved in a tiny amount of acetonitrile, was then added, and the mixture heated to 60° C. for 18 h. Cooling, pouring onto crashed ice, twofold extraction with AcOEt, washing with brine, drying over magnesium sulfate, and evaporation of the solvents, followed by flash chromatography ($SiO_2$, hexane/AcOEt=1/1), yielded eventually 0.161 g of the title compound as off-white foam.
MS (ISP): 575.3 $[M+H]^+$.

Example 49

7-(2-Methoxyethoxy)-N-({4-methoxy-6-[(methylcarbamoyl)amino]pyridin-2-yl}carbamoyl)-1-methyl-1H-indole-2-sulfonamide The title compound was prepared in analogy to the procedure described in Example 1 starting from 7-(2-methoxy-ethoxy)-1-methyl-1H-indole-3-sulfonic acid amide to obtain the desired compound as a white solid. MS (ISN): m/e 505.1 $(M-H)^-$

49a) 7-(2-Methoxy-ethoxy)-1-methyl-1H-indole

To a slurry of sodium hydride (60% in mineral oil, 0.575 g, 14 mmol) in DMF (40 mL) was added in portions 7-(2-methoxy-ethoxy)-1H-indole (Cuny, Gregory D.; Yuan, Junying; Jagtap, Prakash; Degterev, Alexei. US 2005119260, 2.5 g, 13 mmol) over 5 minutes at 5-10° C. The reaction mixture was stirred at rt for 1 h until hydrogen evolution ceased, and methyl iodide (3.7 g, 26 mmol) was added dropwise over 5 minutes at 10-20° C. The mixture was stirred at rt for 2 h, quenched with ice/water, and extracted with tert-butylmethyl ether. The organics were washed, dried and concentrated. The residue was crystallized from ether/hexane to yield the desired compound (2.28 g) as a yellowish liquid. MS (ISP): m/e 206.3 $(M+H)^+$

49b) 7-(2-Methoxy-ethoxy)-1-methyl-1H-indole-3-sulfonyl chloride

This compound was prepared in analogy to the procedure described in Example 4a starting from 7-(2-methoxy-ethoxy)-1-methyl-1H-indole to obtain the desired compound as a yellowish solid. MS (EI): m/e 303.1 (M)

49 c) 7-(2-Methoxy-ethoxy)-1-methyl-1H-indole-3-sulfonic acid amide

This compound was prepared in analogy to the procedure described in Example 4b starting from 7-(2-methoxy-ethoxy)-1-methyl-1H-indole-3-sulfonyl chloride to obtain the desired compound as an off-white solid. MS: (ISN) m/e 283.4 $(M-H)^+$

Example 50

5-(2-Methoxyethyl)-4-methyl-N-({6-[(methylcarbamoyl)amino]-4-(methylsulfonyl)pyridin-2-yl}carbamoyl)thiophene-2-sulfonamide In analogy to example 8, by replacing 1-(6-amino4-bromo-pyridin-2-yl)-3-methyl-urea with 1-(6-amino-4-methanesulfonyl-pyridin-2-yl)-3-methyl-urea, the title compound was obtained as white solid. MS (ISN) $M-H^+$=503.8

50a) 1-(6-Amino-4-methanesulfonyl-pyridin-2-yl)-3-methyl-urea

In analogy to example 3a, by replacing 2.6-diamino-4-bromopyridine with 4-methanesulfonyl-pyridine-2,6-diamine, the title compound was obtained as white solid.
MS (ISP) $M+H^+$=245.1

50b) 4-Methanesulfonyl-pyridine-2,6-diamine

In analogy to example 45b by replacing 2,6-dibromo-4-methylsulfanyl-pyridine with 2,6-dibromo-4-methanesulfonyl-pyridine the title compound was obtained as beige crystals. MS (ISP) $M+H^+$=188.1

50c) 2,6-Dibromo-4-methanesulfonyl-pyridine

To a solution of 0.246 g 2,6-dibromo-4-methylsulfanyl-pyridine in 15 ml dichloromethane was added 0.429 g m-chloroperbenzoic acid and the mixture was stirred at room temperature for 5 h. The reaction mixture was partitioned between 10% aqueous potassium carbonate and dichloromethane. The phases were separated and the organic phase was dried over sodium sulfate and purified by chromatography on silica gel with heptane:ethyl acetate=1:1 to yield 0.237 g of the title compound as white crystals melting at 137-138° C.

Example 51

N-({4-Bromo-6-[(2,2-difluoroethyl)amino]pyridin-2-yl}carbamoyl)-4-(2-methoxyethoxy)-3-methylbenzenesulfonamide Example 51 was prepared in analogy to example 15 starting from 4-(2-methoxy-ethoxy)-3-methyl-benzenesulfonyl chloride (CAS 69129-46-0) (80 mg) and 4-bromo-N-(2,2-difluoro-ethyl)-pyridine-2,6-diamine (55.4 mg) to yield N-({4-bromo-6-[(2,2-difluoroethyl)amino]pyridin-2- yl}carbamoyl)-4-(2-methoxyethoxy)-3-methylbenzene-sulfon-amide (20 mg, 18%) as a light brown solid.
[M−H]⁻=523.1 (Br-isotopes)

Example 52

N,N'-[(4-Bromopyridine-2,6-diyl)bis(iminocarbonyl)]bis[3-(difluoromethoxy)benzenesulfonamide]

Example 52 was obtained as a side product from example 63 to yield N,N'-[(4-bromopyridine-2,6-diyl)bis(iminocarbonyl)]bis[3-(difluoromethoxy)benzenesulfonamide] (22 mg, 7,5%) as a white solid.
[M−H]⁻=686.0 (Br-isotopes)

Example 53

N-{[6-Amino-4-(methylthio)pyridin-2-yl]carbamoyl}-7-methoxy-1-methyl-1H-indole-3-sulfonamide The title compound was prepared in analogy to the procedure described in Example 1 starting from 7-methoxy-1-methyl-1H-indole-3-sulfonic acid amide (cf. example 26b) and 2,6-diamino-4-methylthiopyridine (cf.example 45) to obtain the desired compound as a creamy solid. MS (ISN): m/e 420.4 (M−H)⁻

Example 54

N-({4-Bromo-6-[(dimethylcarbamoyl)amino]pyridin-2-yl}carbamoyl)-5-(2-methoxyethyl)-4-methylthiophene-2-sulfonamide In analogy to example 4, by replacing (6-amino-4-bromo-pyridin-2-yl)-urea with 3-(6-amino-4-bromo-pyridin-2-yl)-1,1-dimethyl-urea, the title compound was obtained as white solid. MS (ISN) M−H⁺=520.3; 518.4

54a) 3-(6-Amino-4-bromo-pyridin-2-yl)-1-dimethyl-urea

In analogy to example 3a, by replacing N-methylamine with N,N-dimethylamine, the title compound was obtained as white solid. MS (ISP) M+H⁺=259.1; 257.3

Example 55

N-[(4-Bromopyridin-2-yl)carbamoyl]-3-chlorobenzenesulfonamide

Example 55 was prepared in analogy to example 11 starting from m-chlorophenylsulfonyl chloride (80 mg) and 2-amino-4-brompyridine (48 mg) to yield N-[(4-bromopyridin-2-yl)carbamoyl]-3-chlorobenzenesulfonamide (12 mg, 8%) as a white crystalline solid.
[M−H]⁻=459.1 (Br, Cl-Isotopes)

Example 56

N-{[6-(3,4-Dihydroisoquinolin-2(1H)-yl)-4-methylpyridin-2-yl]carbamoyl}-5-(2-methoxyethyl)-4-methylthiophene-2-sulfonamide Example 56 was prepared in analogy to example 15 starting from 4-methyl-5-(2-methoxy-ethyl)-thiophene-2-sulfonyl chloride (80 mg) and 6-(3,4-dihydro-1H-isoquinolin-2-yl)-4-methyl-pyridin-2-ylamine hydrochloride (CAS 524717-89-3) (63 mg) to yield N-{[6-(3,4-dihydroisoquinolin-2(1H)-yl)-4-methylpyridin-2-yl]carbamoyl}-5-(2-methoxyethyl)-4-methylthiophene-2-sulfonamide (53 mg, 34%) as a yellow solid.
[M−H]⁻=498.3

Example 57

N-[(6-Amino-4-bromopyridin-2-yl)carbamoyl]-4-(2-methoxyethoxy)-3-methylbenzenesulfonamide Example 57 was prepared in analogy to example 51 starting from 4-(2-methoxy-ethoxy)-3-methyl-benzenesulfonyl chloride (141 mg) and 4-bromo-pyridine-2,6-diamine (100 mg) to yield N-[(6-amino-4-bromopyridin-2-yl)carbamoyl]-4-(2-methoxyethoxy)-3-methylbenzene-sulfonamide (20 mg, 8%) as a solid.
[M+H]⁺=459.0 (Br-isotopes)

Example 58

N-[(6-Cyano-4-methoxypyridin-2-yl)carbamoyl]-5-(2-methoxyethyl)-4-methylthiophene-2-sulfonamide In analogy to example 4, by replacing (6-Amino-4-bromo-pyridin-2-yl)-urea with 6-amino-4-methoxy-pyridine-2-carbonitrile, the title compound was obtained as white solid. MS (ISN) M−H⁺=409.0

58a) 6-Amino-4-methoxy-pyridine-2-carbonitrile

To a solution of 0.40 g 6-bromo-4-methoxy-pyridin-2-ylamine in 8.0 ml dimethylformamide was added 0.265 g copper(I) cyanide and the mixture was heated to 220° C. under microwave irradiation for 6 min. The reaction mixture was partitioned between water and ethyl acetate. The phases were separated and washed with water and brine, dried over magnesium sulfate dihydrate and purified by chromatography on silica gel with heptane : ethyl acetate to yield 0.086 g of the title compound as greenish solid MS (ISP) M+H⁺= 183.1

58b) 6-Bromo-4-methoxy-pyridin-2-ylamine

A solution of 2.00 g 2,6-dibromo-4-methoxy-pyridine in 80 g liquid ammonia under was heated in an autoclave to 140° C. for 4 h. The reaction was cooled to room, evaporated and the residue was purified by silica column chromatography to yield 0.457 g of the title compound as white solid. MS (ISP) M+H⁺=203.2 205.5

Example 59

N-({6-[(Dimethylcarbamoyl)amino]-4-methoxypyridin-2-yl}carbamoyl)-5-(2-methoxyethyl)-4-methylthiophene-2-sulfonamide In analogy to example 4, by replacing (6-amino-4-bromo-pyridin-2-yl)-urea with 3-(6-amino-4-methoxy-pyridin-2-yl)-1,1-dimethyl-urea, the title compound was obtained as white solid. MS (ISN) M−H⁺=470.0

59a) 3-(6-Amino-4-methoxy-pyridin-2-yl)-1,1-dimethyl-urea

In analogy to example 54a, by replacing 2.6-diamino-4-bromopyridine with 4-methoxy-pyridine-2,6-diamine, the title compound was obtained as white solid. MS (ISP) M+H$^+$= 210.9

Example 60

N-[(4-Bromopyridin-2-yl)carbamoyl]-3-methylbenzenesulfonamide

Example 60 was prepared in analogy to example 55 starting from m-toluensulfonyl chloride (80 mg) and 2-amino-4-brompyridine (53 mg) to yield N-[(4-bromopyridin-2-yl)carbamoyl]-3-methylbenzenesulfonamide (46 mg, 30%) as a white crystalline solid.

[M−H]$^−$=370.1 (Br-isotopes)

Example 61

Methyl-{4-methoxy-6-[({[5-(2-methoxyethyl)-4-methyl-2-thienyl]sulfonyl}carbamoyl)amino]pyridin-2-yl}carbamate In analogy to example 4, by replacing (6-amino-4-bromo-pyridin-2-yl)-urea with (6-amino-4-methoxy-pyridin-2-yl)-carbamic acid methyl ester, the title compound was obtained as white solid. MS (ISN) M−H$^+$=457.5

61 a) (6-Amino-4-methoxy-pyridin-2-yl)-carbamic acid methyl ester

To a solution of 4-methoxy-pyridine-2,6-diamine in 2 ml acetonitrile was added 1,1-carbonyldi(1,2,4-triazole) and the mixture was stirred at room temperature for 1 h. To the resulting mixture was added 0.23 g methanol and the mixture was stirred at room temperature for 2 h. The reaction mixture was partitioned between water and ethyl acetate. The phases were separated and the organic phase was washed with water and brinedried over magnesium sulfate and evaporated. The residue was recrystallized from ethyl acetate/heptane to yield 0.038 g of the title compound as light brown solid. MS (ISP) M+H$^+$=298.1

Example 62

N-[(6-Amino-4-cyanopyridin-2-yl)carbamoyl]-5-(2-methoxyethyl)-4-methylthiophene-2-sulfonamide In analogy to example 4, by replacing (6-amino-4-bromo-pyridin-2-yl)-urea with 2.6-diamino-4-cyano-pyridine (example 23b), the title compound was obtained as white solid. MS (ISN) M−H$^+$=394.1

Example 63

N-[(6-Amino-4-bromopyridin-2-yl)carbamoyl]-3-(difluoromethoxy)benzenesulfonamide Example 63 was prepared in analogy to example 51 starting from 4-(difluoromethoxy)benzenesulfonyl chloride (103 mg) and 4-bromo-pyridine-2,6-diamine (80 mg) to yield N-[(6-amino-4-bromopyridin-2-yl)carbamoyl]-3-(difluoromethoxy)benzene-sulfonamide (53 mg, 34%) as a white solid.

[M−H]$^−$=437.0 (Br-Isotopes)

Example 64

N-[(6-Amino-4-ethoxypyridin-2-yl)carbamoyl]-5-(2-methoxyethyl)-4-methylthiophene-2-sulfonamide In analogy to example 4, by replacing (6-amino-4-bromo-pyridin-2-yl)-urea with 4-ethoxy-pyridine-2,6-diamine the title compound was obtained as white solid. MS (ISN) M−H$^+$= 413.4

Example 65

N-[(4-Bromopyridin-2-yl)carbamoyl]-5-[4-(cyanomethyl)phenyl]thiophene-2-sulfonamide 5-(4-Cyanomethyl-phenyl)-thiophene-2-sulfonic acid amide (70 mg) and (4-bromo-pyridin-2-yl)-bis-carbamic acid phenyl ester (135 mg) are suspended in DMF (1.5 mL). DBU (46 mg) is added to the mixture which turned subsequently brown. The mixture was stirred at ambient temperature for 45 min. After that, aqueous HCl (1N, 1 mL) and water (1 mL) was added to the mixture which was then stirred for additional 60 min. The crude product was extracted with EtOAc (3×30 mL). The combined organic layers were washed with brine, dried over Na$_2$SO$_4$, filtrated and evaporated to dryness. The crude product was purified by preparative HPLC to yield N-[(4-bromopyridin-2-yl)carbamoyl]-5-[4-(cyanomethyl)phenyl]thiophene-2-sulfonamide (2 mg, 2%) as a yellow amorphous solid.

[M−H]$^{−=479.3}$ (Br-isotopes)

65a) (4-Bromo-pyridin-2-yl)-bis-carbamic acid phenyl ester

Phenyl chloroformate (199 mg) was dropped to a solution of 2-amino-4-bromopyridine (100 mg) in pyridine (2 mL) at 25° C. The obtained mixture was stirred for 3 h at 25° C. The mixture was evaporated to dryness, suspended with water and aqueous NH$_4$Cl solution (10%, 2 mL) until a yellow precipitate was obtained. The solid was filtrated, washed with water and dried to yield (4-bromo-pyridin-2-yl)-bis-carbamic acid phenyl ester (305 mg, 127%) as a crude product which was used without further purification.

65b) 5-(4-Cyanomethyl-phenyl)-thiophene-2-sulfonic acid tert-butylamide

5-Bromo-thiophene-2-sulfonic acid tert.-butylamide (0.6 g) was suspended in toluene (5 mL) under an Ar-atmosphere. To the suspension (4-cyanomethylphenyl)boronic acid (486 mg), Na$_2$CO$_3$ (533 mg), water (2.5 ml) and EtOH (2.5 mL) was added. To this suspension 2'-(dimethylamino)-2-biphenyl-palladium (II) chloride dinorbornylphosphine complex (23 mg) was added and the mixture was stirred for 18 h at 80° C. After that the suspension was cooled to 25° C., evaporated to ⅓ of the original volume and treated with EtOAc (30 mL). The organic layer was washed with aqueous HCl (1N, 10 mL) and brine. The organic layer was dried over Na$_2$SO$_4$, filtrated and evaporated to dryness. The crude material was purified by flash chromatography (eluent CH$_2$Cl$_2$, 2N NH$_3$ in methanol) to yield 5-(4-cyanomethyl-phenyl)-thiophene-2-sulfonic acid tert-butylamide (268 mg, 40%) as a light yellow solid.

[M−H]$^−$=333.1

65c) 5-(4-Cyanomethyl-phenyl)-thiophene-2-sulfonic acid amide 5-(4-Cyanomethyl-phenyl)-thiophene-2-sulfonic acid tert-butylamide (260 mg) was suspended in TFA (10 mL) and stirred 2 h at 50° C. The mixture was evaporated to dryness and triturated with toluene (2 mL). The obtained precipitate was filtered off, washed with toluene and dried in vacuo to yield 5-(4-Cyanomethyl-phenyl)-thiophene-2-sulfonic acid amide (157 mg, 73%) as a white solid.

Example 66

N-({4-Bromo-6-[(2,4-dimethoxybenzyl)amino]pyridin-2-yl}carbamoyl)-5-(2-methoxyethyl)-4-methylthiophene-2-sulfonamide Example 66 was prepared in analogy to example 15 starting from 4-methyl-5-(2-methoxy-ethyl)-thiophene-2-sulfonyl chloride (80 mg) and 4-bromo-N-(2,4-dimethoxybenzyl)-pyridine-2,6-diamine (78 mg) to yield N-({4-bromo-6-[(2,4-dimethoxybenzyl)amino]pyridin-2-yl}carbamoyl)-5-(2-methoxyethyl)-4-methylthiophene-2-sulfonamide (4 mg; 2%) as yellow solid.
[M−H]$^-$=597.0 (Br-Isotopes)

66a) 4-Bromo-N,N'-bis-(2,4-dimethoxy-benzyl)-1-oxy-pyridine-2,6-diamine 2,4,6-Tribromo-pyridine 1-oxide (CAS 170875-37-3) (15.88 g) was suspended in toluene (240 ml), K$_2$CO$_3$ (16.56 g) and 2,4-dimethoxybenzylamine (36 ml) was added to the suspension. The mixture was stirred for 22 h at 110° C., cooled to 25° C., ethyl acetate (500 ml) was added and extracted with 3M sodium hydroxide solution (250 ml) and 3× with water (250 ml each). The organic layer was dried over sodium sulfate, filtrated and evaporated. The residue was crystallized from DCM and MTBE. 4-Bromo-N,N'-bis-(2,4-dimethoxy-benzyl)-1-oxy-pyridine-2,6-diamine (17.5 g, 72% yield) was obtained as slight brownish crystals.
[M+H]$^+$=504 (Br-Isotope).

66b) 4-Bromo-N-(2,4-dimethoxy-benzyl)-pyridine-2,6-diamine

4-Bromo-N,N'-bis-(2,4-dimethoxy-benzyl)-1-oxy-pyridine-2,6-diamine (3.3 g) was suspended in acetic acid/water (1:1, 24 ml) and iron-powder (436 mg) was added. The mixture was stirred at 75° C. for 16 h, cooled to 25°, ethyl acetate (100 ml) and 3 M sodium hydroxide (100 ml) was added. The mixture was filtrated through a plug of silica gel. The organic phase separated, dried over sodium sulfate, filtrated and evaporated to dryness. The residue was purified by MPLC. 4-Bromo-N-(2,4-dimethoxy-benzyl)-pyridine-2,6-diamine (370 mg, 16% yield)was obtained as white solid.
[M+H]$^+$=338 (Br-Isotope)

Example 67

N,N'-[(4-Bromopyridine-2,6-diyl)bis(iminocarbonyl)]bis(3-chlorobenzenesulfonamide)

Example 67 was obtained as a side product from example 28 to yield N,N'-[(4-bromopyridine-2,6-diyl)bis(iminocarbonyl)]bis(3-chlorobenzenesulfonamide) (34 mg, 12.8%) as a white solid.
[M−H]$^-$=622.0 (Br-Isotopes)

Example 68

N-({6-[(Dimethylcarbamoyl)amino]-4-ethoxypyridin-2-yl}carbamoyl)-5-(2-methoxyethyl)-4-methylthiophene-2-sulfonamide In analogy to example 4, by replacing (6-amino-4-bromo-pyridin-2-yl)-urea with 3-(6-amino-4-ethoxy-pyridin-2-yl)-1,1-dimethyl-urea, the title compound was obtained as white solid. MS (ISN) M−H$^+$=484.0

68a) 3-(6-Amino-4-ethoxy-pyridin-2-yl)-1,1-dimethyl-urea

In analogy to example 54a, by replacing 2.6-diamino-4-bromopyridine with 4-ethoxy-pyridine-2,6-diamine, the title compound was obtained as white solid. MS (ISP) M+H$^+$=225.1

Example 69

N-[(4-Bromopyridin-2-yl)carbamoyl]-4-chlorobenzenesulfonamide

4-Chlorbenzenesulfonyl isocyanate (150 mg) was dissolved in CH$_2$Cl$_2$ (2 mL). 2-Amino-4-brompyridine (132 mg) was added to the mixture. After that the mixture was stirred for 18 h at 25° C. The obtained white precipitate was filtered off and washed with CH$_2$Cl$_2$ and dried in vacuo to yield N-[(4-bromopyridin-2-yl)carbamoyl]-4-chlorobenzenesulfonamide (111 mg; 41%) as a white solid.
[M−H]$^-$=390.1 (Br-isotopes)

Example 70

2-[(3-{[({4-Methoxy-6-[(methylcarbamoyl)amino]pyridin-2-yl}carbamoyl)amino]sulfonyl}-1-methyl-1H-indol-7-yl)oxy]-N,N-dimethylacetamide The title compound was prepared in analogy to the procedure described in Example 1 starting from N,N-dimethyl-2-(1-methyl-3-sulfamoyl-1H-indol-7-yloxy)-acetamide to obtain the desired product as a amorphous brownish solid. MS (ISP): m/532.0 (M−H)$^+$

70a) N,N-Dimethyl-2-(1-methyl-1H-indol-7-yloxy)-acetamide

To a solution of 1-methyl-1-H-indol-7-ol (Chemstep, CAS: 47577-33-4, 2.2 g, 15 mmol) and 2-chloro-N,N-dimethylacetamide (Fluka, CAS: 2675-89-0, 2.0 g, 17 mmol) in acetone (25 mL) were added potassium carbonate (2.5 g, 18 mmol) and potassium iodide, (0.25 g, 1.5 mmol). The reaction mixture was stirred at reflux for 4 h, quenched with ice/water, and extracted with ethyl acetate. The organics were washed, dried and concentrated. The residue was chromatographed on silica gel using heptane/ethyl acetate as eluent to obtain the desired compound (2.9 g) as a creamy solid. MS (ISP): m/e 233.1 (M+H)$^+$

70b) 7-Dimethylcarbamoylmethoxy-1-methyl-1H-indole-3-sulfonyl chloride

This compound was prepared in analogy to the procedure described in Example 5a starting from N,N-Dimethyl-2-(1- methyl-1H-indol-7-yloxy)-acetamide to obtain the desired product as a yellowish solid. MS (ISP): m/e 331.1 (M+H)+

70c) N,N-Dimethyl-2-(1-methyl-3-sulfamoyl-1H-indol-7-yloxy)-acetamide

This compound was prepared in analogy to the procedure described in Example 5b starting from 7-dimethylcarbamoyl-methoxy-1-methyl-1H-indole-3-sulfonyl chloride to obtain the desired product as a yellowish solid. MS (ISP): m/e 310.5 (M−H)+

Example 71

N-{[6-Hydroxy-4-(methylthio)pyridin-2-yl]carbamoyl}-5-(2-methoxyethyl)-4-methylthiphene-2-sulfonamide In analogy to example 4, by replacing (6-amino-4-bromopyridin-2-yl)-urea with 6-amino-4-methylsulfanyl-pyridin-2-ol, the title compound was obtained as white solid. MS (ISN) M−H+=416.0

Example 72

N-[(6-Chloropyridin-2-yl)carbamoyl]-3-methylbenzenesulfonamide

To a suspension of 0.128 g sodium cyanate in 3.0 ml acetonitrile was added 0.11 ml pyridine and 0.19 ml m-toluenesulfonyl chloride and the mixture was sonicated in a ultrasound bath at ca 40° C. for 1.5 h. HPLC showed disappearance of 3-Chloro-benzenesulfonyl chloride. The resulting suspension was added with stirring to a solution of 0.169 g 2-amino-6-chloropyridine in 1.0 ml of acetonitrile and the mixture was stirred at room temperature for 2 h. The reaction mixture was partioned between 0.1N sodium hydroxide and ethyl acetate (pH 10). The phases were separated and the aqueous phase was washed twice with ethyl acetate. The aqueous phase was acidified by addition of 25% hydrochloric acid and extracted with ethyl acetate, the organic phase was evaporated under reduced pressure. The residue was purified by silica column chromatography and crystallisation to yield 0.0995 g of a off-white solid. MS (ISN) M−H+=324.4

Example 73

Methyl-4-({6-[({[5-(2-methoxyethyl)-4-methyl-2-thienyl]sulfonyl}carbamoyl)amino]-4-(methylthio)pyridin-2-yl}amino)butanoate was prepared in analogy to example 45, but using in step 3 methyl 4-iodo-butyrate instead of 1-iodo-2-fluoroethane as electrophile, as off-white solid.
MS (ISP): 515.1 [M−H]−.

Example 74

N-({6-[(3-Hydroxypropyl)amino]-4-(methylthio)pyridin-2-yl}carbamoyl)-5-(2-methoxyethyl)-4-methylthiophene-2-sulfonamide was prepared in analogy to example 48, but using in step 3 tert-butyl-(3-iodo-propoxy)-dimethyl-silane (CAS 78878-05-4) instead of tert-butyl-(2-iodo-ethoxy)-dimethyl-silane as electrophile, as off-white solid.
MS (ISP): 472.8 [M−H]−.

Example 75

5-(2-Methoxyethyl)-4-methyl-N-({4-(methylthio)-6-[(3,3,3-trifluoropropyl)amino]pyridin-2-yl}carbamoyl)thiophene-2-sulfonamide was prepared in analogy to example 45, but using in step 3 1,1,1-trifluoro-3-iodo-propane instead of 1-iodo-2-fluoroethane as electrophile, as off-white solid.
MS (ISP): 511.1 [M−H]−.

Example 76

N-({4-(Ethylthio)-6-[(2-hydroxyethyl)amino]pyridin-2-yl}carbamoyl)-5-(2-methoxyethyl)-4-methylthiophene-2-sulfonamide was prepared in analogy to example 48, but using in step 1 4-ethylsulfanyl-pyridine-2,6-diamine instead of 4-methylsulfanyl-pyridine-2,6-diamine as nucleophile, as light brown solid.
MS (ISP): 473.3 [M−H]−.

The requisite intermediate 4-methylsulfanyl-pyridine-2,6-diamine was prepared as described in example 45, step 1 & 2, but using sodium ethanethiolate instead of sodium methanethiolate, as brown solid.
MS (ISP): 170.1 [M+H]+.

Example 77

2-{3-Methyl-5-[({[4-(trifluoromethyl)pyridin-2-yl]carbamoyl}amino)sulfonyl]-2-thienyl}ethyl acetate 77a) Acetic acid 2-(3-methyl-thiophen-2-yl)-ethyl ester A solution of 2-bromo-3-methylthiophene (35.4 g, 200 mmol, ALFA) in diethyl ether (200 mL) was added drop wise to Mg turnings (5.35 g, 220 mmol) over ~30 min at such a rate as to maintain gentle reflux (at the beginning the reaction was initiated with 2 drops of $Br_2$). After refluxing for 1 h, 2.0M ethylene oxide in THF (150 mL, 300 mmol) was added drop wise at 0° C. over 1 h and stirring was continued at rt for 20 h. After cooling to 0° C. acetyl chloride (22.8 mL, 320 mmol) was added drop wise at 0° C. over 15 min an the suspension was stirred at rt for 18 h. The reaction mixture was diluted with diethyl ether (200 mL) and washed with 1M HCl (200 mL) and 10% brine (200 mL). The aqueous layers were extracted with diethyl ether (100 mL) and the combined organic layers were dried ($Na_2SO_4$) and evaporated affording 49 g brownish oil which was purified by distillation affording 32.8 g (89.0%, GC 96.4%) colorless oil, bp ~120° C./10 mbar.

77b) Acetic acid 2-(5-chlorosulfonyl-3-methyl-thiophen-2-yl)-ethyl ester

A solution of the above prepared acetic acid 2-(3-methyl-thiophen-2-yl)-ethyl ester (32.6 g, 177 mmol) in DCM (180 mL) was added to a suspension of $SO_3$-DMF complex (33.5 g, 212.4 mmol) in DCM (330 mL) and the reaction mixture was refluxed for 2 h. Oxalyl chloride (30.0 mL, 354 mmol) was now added over 30 min and the brown solution was refluxed for 3 h. After cooling to rt the reaction mixture washed with 10% brine (2×300 mL), the aqueous layers were extracted with DCM (250 mL) and the combined organic layers were dried (Na$_2$SO$_4$) and evaporated affording 53, 4 g crude product as a brown oil which was used without further purification in the next step. $^1$H NMR (CDCl$_3$, 250 MHz) □ 2.09 (s, 3H), 2.25 (s, 3H), 3.14 (t, 2H), 4.29 (t, 2H), 7.61 (s, 1H).

77c) Acetic acid 2-(3-methyl-5-sulfamoyl-thiophen-2-yl)-ethyl ester

To a solution of the above prepared crude acetic acid 2-(5-chlorosulfonyl-3-methyl-thiophen-2-yl)-ethyl ester (53.3 g, ca. 177 mmol) in DCM (180 mL) were added 25% aqueous NH$_3$ (53 mL, ~700 mmol) and the biphasic reaction mixture was vigorously stirred at rt for 18 h. After the addition of DCM (1200 mL) the reaction mixture was washed with 10% brine (2×400 mL) and the aqueous layers were extracted with DCM (600 mL). The combined organic layers were dried (Na$_2$SO$_4$) and evaporated affording 48.5 g yellow crystalline residue which was crystallized from hot isobutyl acetate (500 mL) affording 34.8 g (74.7%, GC 97.9%) product as a off white powder. ESI-MS (m/z) 286 (M+Na$^+$, 59); 264 (M+H$^+$, 19).

77d) 2-{3-Methyl-5-[({[4-(trifluoromethyl)pyridin-2-yl]carbamoyl}amino)sulfonyl]-2-thienyl}ethyl acetate In analogy to example 4 using acetic acid 2-(3-methyl-5-sulfamoyl-thiophen-2-yl)-ethyl ester and 4-trifluoromethyl-pyridin-2-ylamine, the title compound was obtained as white solid. MS (ISN) M–H$^+$=450.0

Example 78

5-(2-Hydroxyethyl)-4-methyl-N-{[4-(trifluoromethyl)pyridin-2-yl]carbamoyl}thiophene-2-sulfonamide 2-{3-Methyl-5-[({[4-(trifluoromethyl)pyridin-2-yl]carbamoyl}amino)sulfonyl]-2-thienyl}ethyl acetate (310 mg, 0.55 mmol, 1 equiv.) was saponified by addition of 1 N LiOH (1.2 mL, 1 mmol, 2 equiv.) in MeOH (5 mL) for 60 min. The solution was purified by chromatography on a HPLC 75×30 mm RP18 5 μm column, with A=0.1% HCOOH and B=MeCN and with a gradient of 20% to 70% B in 10 min. The corresponding fractions were lyophilized to give the titled compound, 89 mg, mle 408.0 (MH$^-$).

Example 79

N-{[6-Amino-5-fluoro-4-(trifluoromethyl)pyridin-2-yl]carbamoyl}-5-(2-methoxyethyl)-4-methylthiophene-2-sulfonamide In analogy to example 4, by replacing (6-amino-4-bromopyridin-2-yl)-urea with 3-fluoro-4-trifluoromethyl-pyridine-2,6-diamine, the title compound was obtained as white solid. MS (ISN) M–H$^+$=455.0

Example 80

5-(2-Methoxyethyl)-4-methyl-N-({6-[(2-methylprop-2-en-1-yl)amino]-4-(methylthio)pyridin-2-yl}carbamoyl)thiophene-2-sulfonamide was prepared in analogy to example 45, but using in step 3 3-bromo-2-methyl-propene instead of 1-iodo-2-fluoroethane as electrophile, as off-white crystals.
MS (ISN): 469.2 [M–H]$^-$.

Example 81

2-{5-[({[6-Amino-54-fluoro-4-(trifluoromethyl)pyridin-2-yl]carbamoyl}amino)sulfonyl]-3-methyl-2-thienyl}ethyl acetate In analogy to example 77iv), by replacing 4-trifluoromethyl-pyridin-2-ylamine with 3-fluoro-4-trifluoromethyl-pyridine-2,6-diamine, the title compound was obtained as white solid. MS (ISN) M–H$^+$=483.3

Example 82

N-[(6-Amino-4-bromopyridin-2-yl)carbamoyl]-1-benzofuran-3-sulfonamide

The below prepared benzofuran-3-sulfonic acid amide (0.051 g, 0.259 mmol) was dissolved in 1.5 mL of abs. acetonitrile and treated successively with triethylamine (0.090 mL, 2.5 eq.) and phenyl chloroformate (0.0405 g, 1.0 eq.), and the mixture was then kept at ambient temperature for 1 h. 4-Bromo-pyridine-2,6-diamine (0.0486 g, 1.0 eq.), dissolved in a tiny amount of acetonitrile, was added, and the mixture heated to 60° C. for 18 h. Cooling, pouring onto crashed ice, twofold extraction with AcOEt, washing with water, drying over sodium sulfate, and evaporation of the solvents, followed by flash chromatography (SiO$_2$, hexane/AcOEt=3/7) and crystallization from AcOEt/heptane, yielded finally 0.015 g of the title compound as off-white solid.
MS (ISP): 411.1 [M+H]$^+$.
The Starting Materials were Prepared as Follows:

82a) Benzofuran-3-sulfonyl chloride

To SO$_3$-DMF complex (0.368 g, 2.40 mmol), dissolved in 1,2-dichloroethane (4.0 mL), was added benzofuran (0.236 g, 2.00 mmol), and the reaction mixture was then kept at 50° C. for 30 Min. After cooling, thionyl chloride (0.174 mL, 2.4 mmol) was added, and the reaction allowed proceeding at 60-70° C. for another 30 Min. After cooling, the mixture was poured onto crashed ice, twofold extracted with AcOEt, washed with brine, dried over sodium sulfate, and evaporated to dryness. Flash chromatography (SiO$_2$, heptane/AcOEt=95/5) yielded 0.108 g of the title compound as brownish crystals, used directly for the next step.

82b) Benzofuran-3-sulfonic acid amide

To the above prepared benzofuran-3-sulfonyl chloride (0.104 g, 0.480 mmol) was added ammonia (6 eq., 0.5 M in dioxane) and the mixture stirred for one night at 50° C. Evaporation of the solvent, followed by flash chromatography (SiO$_2$, heptane/AcOEt=7/3) and direct crystallization from heptane/AcOEt, generated 0.036 g of the title compound as off-white crystals. Extensive nOE measurements and 13C-NMR NMR corroborated the structure.
MS (ISP): 196.0 [M–H]$^-$.

Example 83

N-[(6-Amino-4-bromopyridin-2-yl)carbamoyl]-5-bromo-1-benzofuran-3-sulfonamide was prepared in analogy to example 82, but starting the sequence with 5-bromo-benzofuran instead of benzofuran, as off-white solid.
MS (ISP): 486.9 [M–H]$^-$.

Example 84

N-{[6-Amino-5-fluoro-4-(trifluoromethyl)pyridin-2-yl]carbamoyl}-5-(2-hydroxyethyl)-4-methylthiophene-2-sulfonamide In analogy to example 78, by replacing 2-{3-methyl-5-[({[4-(trifluoromethyl)pyridin-2-yl]carbamoyl}amino)sulfonyl]-2-thienyl}ethyl acetate with 2-{5-[({[6-amino-5-fluoro-4-(trifluoromethyl)pyridin-2-yl]carbamoyl}amino)sulfonyl]-3-methyl-2-thienyl}ethyl acetate, the title compound was obtained as white solid. MS: M−H$^+$=441.2

Example 85

N-{[6-Amino-4-(trifluoromethyl)pyridin-2-yl]carbamoyl}-5-(2-methoxyethyl)-4-methylthiophene-2-sulfonamide In analogy to example 4, by replacing (6-amino-4-bromopyridin-2-yl)-urea with 4-trifluoromethyl-pyridine-2,6-diamine the title compound was obtained as white solid. MS (ISN) M−H$^+$=437.3

85a) 4-Trifluoromethyl-pyridine-2,6-diamine

A mixture of 4.00 g 2,6-dichloro-4-trifluoropyridine 0.400 g copper powder and 80 g liquide ammonia was heated to 140° C. for 48 h. The ammonia was allowed to evaporate and the residue was purified by chromatography on silica gel with dichloromethane: methanol:ammonia=9:1:0.1 to yield the title compound as light brown solid. MS (ISP): 178.1 [M+H]$^−$.

Example 86

5-(2-Methoxyethyl)-4-methyl-N-{[6-methyl-4-(methylthio)pyridin-2-yl]carbamoyl}thiophene-2-sulfonamide In analogy to example 4, by replacing (6-amino-4-bromopyridin-2-yl)-urea with 6-methyl-4-methylsulfanyl-pyridin-2-ylamine the title compound was obtained as white solid. MS (ISN) M−H$^+$=414.5

86a) 6-Amino-4-methylsulfanyl-pyridine-2-carboxylic acid methyl ester

To a solution of 0.100 g 6-bromo-4-methylsulfanyl-pyridin-2-ylamine in 3.0 ml of methanol was added PdCl2.dppf.CH2Cl2 and 0.09568 ml triethylamine and the reaction mixture was heated under 70 bar carbonmonoxide at 130° C. for 20 h. Then the solvent was evaporated and the crude was purified by silica column chromatography to yield 0.054 g of the title compound as light red solid. MS (ISP): 199.3 [M+H]$^+$.

86b) (6-Amino-4-methylsulfanyl-pyridin-2-yl)-methanol

To a solution of 0.198 g 6-amino-4-methylsulfanyl-pyridine-2-carboxylic acid methyl ester in 4 ml tetrahydrofuran was added 0.044 g lithiumborohydride and the mixture was stirred at room temperature for 3 h. The reaction mixture was partitioned between ethyl acetate and brine. The phases were separated and the organic phase was purified by chromatography on silica gel with ethyl acetate to ethyl acetate:methanol=9:1. to yield 0.14 g of the title compound as beige crystals. MS (ISP): 171.1 [M+H]$^+$.

86c) 6-Bromomethyl-4-methylsulfanyl-pyridin-2-ylamine

To a solution of 0.10 g (6-amino-4-methylsulfanyl-pyridin-2-yl)-methanol in 6 ml dichloromethane was added 0.292 g tetrabromomethane and 0.231 g triphenylphosphin and the mixture was stirred at room temperature for 1 h. The reaction mixture was purified by chromatography on silica gel with heptan:ethyl acetate=1:1 to yield 0.075 g of the title compound as white crystals MS (ISP): 232.9; 234.9 [M+H]$^+$.

86d) 6-Methyl-4-methylsulfanvy-pyridin-2-ylamine

To a Solution of 0.074 g 6-bromomethyl-4-methylsulfanyl-pyridin-2-ylamine in 4 ml tetrahydrofuran was added 0.006 g palladium(II) acetate, a solution of 0.043 potassium fluoride in 0.8 ml water and 0.10 ml polymethylhydroxysilane and the mixture was stirred at room temperature for 30 min. The dark suspension was purified by chromatography on silica gel with ethyl acetate:methanol=9:1 to yield 0.024 g of the title compound as slightly yellow crystals melting at 81-83° C. MS (ISP): 155.1 [M+H]$^+$.

Example 87

N-{[6-Amino-4-(methylthio)pyridin-2-yl]carbamoyl}-5-bromo-1-benzofuran-3-sulfonamide was prepared in analogy to example 83, but using in the last step 4-methylsulfanyl-pyridine-2,6-diamine instead of 4-bromo-pyridine-2,6-diamine as nucleophile, as white solid. MS (ISN): 455.0 [M−H]$^−$.

Example 88

Sodium-6-[({[5-(2-methoxyethyl)-4-methyl-2-thienyl]sulfonyl}carbamoyl)amino]-4-(methylthio)pyridine-2-carboxylate To a solution of 0.045 g 5-(2-methoxy-ethyl)-4-methyl-thiophene-2-sulfonic acid amide in 3 ml acetonitrile was added 0.036 g phenychloroformate and 0.048 g triethylamine and the mixture was stirred at room temperature for 1 h. The resulting suspension was added to a solution of 0.038 g 6-amino-4-methylsulfanyl-pyridine-2-carboxylic acid methyl ester in acetonitrile (ca 0.5 ml) and the mixture was heated to 60° C. for 18 h. The resulting mixture was cooled to room temperature and partitioned between 0.1N sodium hydroxide and ethyl acetate. The phases were separated and the aqueous phase was purified by chromatography on MCl-gel with a gradient of water to 50% acetonitrile. The product fractions were combined, concentrated to ca. 2 ml and lyophilized to yield 0.023 g of the title compound as white powder. MS (ISN): 444.5 [M−H]$^−$.

Example 89

N-({6-[(Methylcarbamoyl)amino]-4-(methylthio)pyridin-2-yl}carbamoyl)-1-benzofuran-3-sulfonamide The above prepared benzofuran-3-sulfonic acid amide (0.050 g, 0.254 mmol) was dissolved in 1.5 mL of abs. acetonitrile and treated successively with triethylamine (0.088 mL, 2.5 eq.) and phenyl chloroformate (0.0397 g, 1.0 eq.), and the mixture was then kept at ambient temperature for 1 h. 1-(6-Amino-4-methylsulfanyl-pyridin-2-yl)-3-methyl-urea (see below, 0.0538 g, 1.0 eq.), dissolved in a tiny amount of acetonitrile, was then added, and the mixture heated to 60° C. overnight. Cooling, pouring onto crashed ice, twofold extraction with AcOEt, washing with water, drying over sodium sulfate, and evaporation of the solvents, followed by flash chromatography (SiO$_2$, MeOH/AcOEt=5/95) and crystallization from AcOEt/heptane, delivered eventually 0.016 g of the title compound as off-white solid.

MS (ISP): 434.1 [M−H]$^−$.

Example 90

N-{[6-chloro-4-(trifluoromethyl)pyridin-2-yl]carbamoyl}-5-(2-methoxyethyl)-4-methylthiophene-2-sulfonamide In analogy to example 4, by replacing (6-amino-4-bromo-pyridin-2-yl)-urea with 6-chloro-4-trifluoromethyl-pyridin-2-ylamine the title compound was obtained as white solid. MS (ISN) M−H$^+$=456.0

90 a) 6-Chloro-4-trifluoromethyl-pyridin-2-ylamine

A mixture of 5.00 g 2,6-dichloro-4-trifluoromethyl-pyridine and 80 g ammonia was heated in an autoclave at 120° C. for 24 h. Ammonia was allowed to evaporate and the residue was purified on silica gel with methylenechloride:methanol:ammonia=9:1:0.1 to yield 4.01 g of the title compound as off white crystals MS (ISP) M+H$^+$=210.9

Example 91

Methyl-6-[({[5-(2-methoxyethyl)-4-methyl-2-thienyl]sulfonyl}carbamoyl)amino]-4-(trifluoromethyl)pyridine-2-carboxylate In analogy to example 4, by replacing (6-amino-4-bromo-pyridin-2-yl)-urea with 6-amino-4-trifluoromethyl-pyridine-2-carboxylic acid methyl ester the title compound was obtained as white solid. MS (ISN) M−H$^+$=480.0

91 a) 6-Amino-4-trifluoromethyl-pyridine-2-carboxylic acid methyl ester

To a solution of 0.100 g 6-chloro-4-trifluoromethyl-pyridin-2-ylamine in 3.0 ml of methanol was added PdCl2.dppf.CH2Cl2 and 0.09568 ml triethylamine and the reaction mixture was heated under 70 bar carbonmonoxide at 130° C. for 20 h. Then the solvent was evaporated and the crude was purified by silica column chromatography to yield 0. g of the title compound as light red solid. MS (ISP): [M+H]$^+$.

Example 92

Methyl-6-[({[5-(2-acetoxyethyl)-4-methyl-2-thienyl]sulfonyl}carbamoyl)amino]-4-(trifluoromethyl)pyridine-2-carboxylate To a solution of 0.263 g acetic acid 2-(3-methyl-5-sulfamoyl-thiophen-2-yl)-ethyl ester in 5 ml acetonitrile was added 0.188 g phenylchloroformate and 0.252 g triethylamine at ° C. and the mixture was stirred at this temperature for 2 h. To the resulting suspension was added 0.220 g 6-amino-4-trifluoromethyl-pyridine-2-carboxylic acid methyl ester and the mixture was heated to 60° C. for 18 h. The reaction mixture was partitioned between 10% citric acid and ethyl acetate. The phases were separated and the organic phase was washed with brine and evaporated. The residue was triturated with t-butylmethylether. The solid was collected by filtration to yield 0.376 g of the title compound as white crystals. MS (ISN) M−H$^+$=508.3

Example 93

2-{5-[({[6-chloro-4-(trifluoromethyl)pyridin-2-yl]carbamoyl}amino)sulfonyl]-3-methyl-2-thienyl}ethyl acetate To a solution of 0.263 g acetic acid 2-(3-methyl-5-sulfamoyl-thiophen-2-yl)-ethyl ester in 5 ml acetonitrile was added 0.188 g phenylchloroformate and 0.252 g triethylamine at ° C. and the mixture was stirred at this temperature for 2 h. To the resulting suspension was added 0.196 g 6-chloro-4-trifluoromethyl-pyridin-2-ylamine and the mixture was heated to 60C for 18 h. The reaction mixture was partitioned between 10% citric acid and ethyl acetate. The phases were separated and the organic phase was washed with brine and evaporated. The residue was triturated with diethylether. The solid was collected by filtration to yield the title compound as white crystals. MS (ISN) M−H$^+$=488.4

Example 94

5-(2-Methoxyethyl)-4-methyl-N-({6-[(methylcarbamoyl)amino]-4-(methylsulfinyl)pyridin-2-yl}carbamoyl)thiophene-2-sulfonamide In analogy to example 4, by replacing (6-amino-4-bromo-pyridin-2-yl)-urea with 1-(6-amino-4-methanesulfinyl-pyridin-2-yl)-3-methyl-urea, the title compound was obtained as white solid. MS (ISN) M−H$^+$=488.4

94a) 1-(6-Amino-4-methanesulfinyl-pyridin-2-yl)-3-methyl-urea

In analogy to example 3a, by replacing 2.6-diamino4-bromopyridine with 4-methanesulfinyl-pyridine-2,6-diamine, the title compound was obtained as white crystals. MS (ISP) M+H$^+$=229.1

94b) 4-Methanesulfinyl-pyridine-2,6-diamine

In analogy to example 14b, by replacing 2,6-dibromo-4-methylsulfanyl-pyridine 2,6-dibromo-4-methanesulfinyl-pyridine the title compound was obtained as white crystals. MS (ISP) M+H$^+$=172.2

94c) 2,6-Dibromo-4-methanesulfinyl-pyridine

To a solution of 0.282 g 2,6-dibromo-4-methylsulfanyl-pyridine (Example 45a) in 5.0 ml dichlormethane was added 0.246 g m-chloroperbenzoic acid at 0° C. and the mixture was then stirred at room temperature for 3 h. The reaction mixture was partitioned between 10% potassium carbonate and ethyl acetate. The phases were separated and the organic phase was washed with brine, dried over sodium sulphate and purified by chromatography on silica gel with ethyl acetate to yield 0.260 g of the title compound as white crystals melting at 98-100° C.

Example 95

N-{[6-(Carbamoylamino)-4-(methylsulfinyl)pyridin-2-yl]carbamoyl}-5-(2-methoxyethyl)-4-methylthiophene-2-sulfonamide In analogy to example 94, by replacing (6-amino-4-bromo-pyridin-2-yl)-urea with 1-(6-amino-4-methanesulfinyl-pyridin-2-yl)-3-methyl-urea, the title compound was obtained as white solid. MS (ISN) M–H$^+$=474.4

95a) (6-Amino-4-methanesulfinyl-pyridin-2-yl)-urea

In analogy to example 2b, by replacing 2.6-diamino-4-bromopyridine with 4-methanesulfinyl-pyridine-2,6-diamine, the title compound was obtained as white solid. MS (ISP) M+H$^+$=199.1

Example 96

5-(2-methoxyethyl)-4-methyl-N-{[6-methyl-4-(trifluoromethyl)pyridin-2-yl]carbamoyl}thiophene-2-sulfonamide In analogy to example 4, by replacing (6-amino4-bromo-pyridin-2-yl)-urea with 6-methyl-4-trifluoromethyl-pyridin-2-ylamine the title compound was obtained as white solid. MS (ISN) M–H$^+$=435.9

96a) 6-Methyl-4-trifluoromethyl-pyridin-2-ylamine

A mixture of 4.7 g 2-chloro-6-methyl-4-trifluoromethyl-pyridine and 80 g ammonia was heated in an autoclave at 120° C. for 24 h. Ammonia was allowed to evaporate and the residue was purified on silica gel with methylene chloride:methanol:ammonia=9:1:0.1 to yield 4.01 g of the title compound as off white crystals MS (ISP) M+H$^+$=177.1 melting at 53.5-54.5° C.

Example 97

Methyl-6-[({[5-(2-hydroxyethyl)-4-methyl-2-thienyl]sulfonyl}carbamoyl)amino]-4-(trifluoromethyl)pyridine-2-carboxamide To a solution of 0.100 g methyl 6-[({[5-(2-acetoxyethyl)-4-methyl-2 thienyl]sulfonyl}carbamoyl)amino]-4-(trifluoromethyl)pyridine-2-carboxylate in 1 ml methanol was added 0.10 ml ammonia 25% in water and the mixture was kept at room temperature for 18 h. The solvent was evaporated and the residue was triturated with ethyl acetate. No complete conversion by MS. The solid was dissolved in 1 ml 25% aqueous ammonia and kept at room temperature for 18. The solvents were evaporated and the residue was triturated with ethyl acetate. The solid was collected by filtration to yield 0.070 g of the ammonium salt of the title compound as white powder.

MS (ISN) M–H$^+$=451.1

Example 98

Methyl-6-({[(5-methyl-3-thienyl)sulfonyl]carbamoyl}amino)-4-(trifluoromethyl)pyridine-2-carboxylate In analogy to example 3, by replacing 1-(6-amino-4-bromo-pyridin-2-yl)-3-methyl-urea with 6-amino-4-trifluoromethyl-pyridine-2-carboxylic acid methyl ester the title compound was obtained as white solid. MS (ISN) M–H$^+$=422.1

Example 99

Ethyl-2-[({[5-(2-methoxyethyl)-4-methyl-2-thienyl]sulfonyl}carbamoyl)amino]-6-[(methylcarbamoyl)amino]isonicotinate In analogy to example 4, by replacing (6-amino-4-bromo-pyridin-2-yl)-urea with 2-amino-6-(3-methyl-ureido)-isonicotinic acid ethyl ester the title compound was obtained as white solid. MS (ISN) M–H$^+$=498.0

99a) 2-Amino-6-(3-methyl-ureido)-isonicotinic acid ethyl ester

In analogy to example 3a, by replacing 2.6-diamino-4-bromopyridine with 2,6-diaminoisonicotinic acid ethyl ester, the title compound was obtained as white crystals. MS (ISP) M+H$^+$=238.3

Example 100

Ethyl-2-amino-6-[({[5-(2-methoxyethyl)-4-methyl-2 thienyl]sulfonyl}carbamoyl)amino]isonicotinate In analogy to example 4, by replacing (6-amino-4-bromo-pyridin-2-yl)-urea with 2,6-diaminoisonicotinic acid ethyl ester, the title compound was obtained as white solid. MS (ISN) M–H$^+$=441.0

Example 101

2-[({[5-(2-Methoxyethyl)-4-methyl-2-thienyl]sulfonyl}carbamoyl)amino]-6-[(methylcarbamoyl)amino]isonicotinamide In analogy to example 4, by replacing (6-amino-4-bromo-pyridin-2-yl)-urea with 2-amino-6-(3-methyl-ureido)-isonicotinamide, the title compound was obtained as white solid. MS (ISN) M–H$^+$=469.4

101a) 2-Amino-6-(3-methyl-ureido)-isonicotinamide

In analogy to example 3a, by replacing 2.6-diamino-4-bromopyridine with 2,6-diaminoisonicotinamide the title compound was obtained as white crystals. MS (ISP) M+H$^+$=210.1

Example 102

2-Amino-6-[({[5-(2-methoxyethyl)-4-methyl-2-thienyl]sulfonyl}carbamoyl)amino]isonicotinamide In analogy to example 4, by replacing (6-amino-4-bromo-pyridin-2-yl)-urea with 2,6-diaminoisonicotinamide, the title compound was obtained as white solid. MS (ISN) M–H$^+$=412.4

Example 103

2-[({[5-(2-Methoxyethyl)-4-methyl-2-thienyl]sulfonyl}carbamoyl)amino]-N-methyl-6-[(methylcarbamoyl)amino]isonicotinamide In analogy to example 4, by replacing (6-amino-4-bromopyridin-2-yl)-urea with 2-amino-N-methyl-6-(3-methyl-ureido)-isonicotinamide, the title compound was obtained as white solid. MS (ISN) M–H$^+$=483.1

103a) 2-Amino-N-methyl-6-(3-methyl-ureido)-isonicotinamide

In analogy to example 3a, by replacing 2.6-diamino-4-bromopyridine with 2,6-diamino-N-methyl-isonicotinamide the title compound was obtained as white crystals. MS (ISP) M+H$^+$=224.3

103b) 2,6-Diamino-N-methyl-isonicotinamide

A mixture of 0.270 g 2,6-diaminoisonicotinic acid ethyl ester and 5 ml of a 2M solution of methylamine in methanol was stirred at 70° C. for 24 h. The solvent were evaporated and the residue was triturated with ethyl acetate to yield 0.214 g of the title compound as light brown solid. MS (ISP) M+H$^+$=167.4

Example 104

2-Amino-6-[({[5-(2-methoxyethyl)-4-methyl-2-thienyl]sulfonyl}carbamoyl)amino]-N-methylisonicotinamide In analogy to example 4, by replacing (6-amino-4-bromopyridin-2-yl)-urea with 2,6-diamino-N-methyl-isonicotinamide, the title compound was obtained as white solid. MS (ISN) M–H$^+$=425.8

Example 105

Methyl-6-[({[5-(2-hydroxyethyl)-4-methyl-2-thienyl]sulfonyl}carbamoyl)amino]-4-(trifluoromethyl)pyridine-2-carboxylate To a suspension of 0.100 g methyl 6-[({[5-(2-acetoxyethyl)-4-methyl-2-thienyl]sulfonyl}carbamoyl)amino]-4-(trifluoromethyl)pyridine-2-carboxylate in 1.5 ml methanol was added 0.02 g sodium hydride 55% in oil. The resulting solution was stirred at room temperature for 18 h. The reaction mixture was partitioned between 10% citric acid and ethyl acetate. The phases were separated and the organic phase was washed with brine and evaporated to yield the title compound as white foam. MS (ISN) M–H$^+$=466.3

Example 106

5-(2-Hydroxyethyl)-N-{[6-(hydroxymethyl)-4-(trifluoromethyl)pyridin-2-yl]carbamoyl}-4-methylthiophene-2-sulfonamide To a solution of 0.100 g methyl 6-[({[5-(2-acetoxyethyl)-4-methyl-2-thienyl]sulfonyl}carbamoyl)amino]-4-(trifluoromethyl)pyridine-2-carboxylate in 1.5 ml tetrahydrofuran was added 0.02 g lithiumborohydride and the mixture was stirred at room temperature for 3 h. The reaction mixture was partitioned between water and ethyl acetate. The phases were separated. The organic phase was washed with water. To he combined water phases was added 1 ml 10% citric acid and the mixture was extracted with ethyl acetate. The organic phase was washed with brine and evaporated to yield the title compound as white foam (containing acetoxy and hydroxyethyl ca 1:1) The mixture was dissolved in ca 2 ml methanol and ca 0.05 ml 28% sodium hydroxide and kept at room temperature for 5 h. The reaction mixture was partitioned between 10% citric acid and ethyl acetate. The phases were separated and the organic phase was washed with brine and evaporated to yield 0.049 g of the title compound as white foam. MS (ISN) M–H$^+$=438.4

Example 107

N'-Hydroxy-2-[({[5-(2-methoxyethyl)-4-methyl-2-thienyl]sulfonyl}carbamoyl)amino]-6-[(methylcarbamoyl)amino]pyridine-4-carboximidamide In analogy to example 4, by replacing (6-amino-4-bromopyridin-2-yl)-urea with 2-amino-N-hydroxy-6-(3-methyl-ureido)-isonicotinamidine, the title compound was obtained as white solid. MS (ISN) M–H$^+$=484.5

107a) 2-Amino-N-hydroxy-6-(3-methyl-ureido)-isonicotinamidine

To a solution of 0.200 g 1-(6-amino-4-cyano-pyridin-2-yl)-3-methyl-urea (example 23a) in 3.2 ml ethanol and 1.6 ml water was added 0.145 g hydroxylamine hydrochloride and 0.333 g sodium carbonate and the mixture was stirred at 85° C. for 2 h. The reaction mixture was purified by solid phase extraction with ethyl acetate to yield 0.154 g of the title compound as light yellow solid. MS (ISP) M+H$^+$=225.1

Example 108

2-Amino-N'-hydroxy-6-[({[5-(2-methoxyethyl)-4-methyl-2-thienyl]sulfonyl}carbamoyl)amino]pyridine-4-carboximidamide In analogy to example 4, by replacing (6-amino-4-bromopyridin-2-yl)-urea with 2,6-diamino-N-hydroxy-isonicotinamidine, the title compound was obtained as white solid. MS (ISN) M–H$^+$=427.0

108a) 2,6-Diamino-N-hydroxy-isonicotinamidine

In analogy to example 107a, by replacing 1-(6-amino-4-cyano-pyridin-2-yl)-3-methyl-urea with 2.6-diamino-4-cyano-pyridine (example 23b) the title compound was obtained as white crystals. MS (ISP) M+H$^+$=168.1

Example 109

5-(2-Methoxyethyl)-4-methyl-N-({6-[(methylcarbamoyl)amino]-4-(5-methyl-1,2,4-oxadiazol-3-yl)pyridin-2-yl}carbamoyl)thiophene-2-sulfonamide In analogy to example 4, by replacing (6-amino-4-bromopyridin-2-yl)-urea with 1-[6-amino-4-(5-methyl-[1,2,4]oxadiazol-3-yl)-pyridin-2-yl]-3-methyl-urea, the title compound was obtained as white solid. MS (ISN) M–H$^+$=508.0

109a) 4-(5-Methyl-[1,2,4]oxadiazol-3-yl)-pyridine-2,6-diamine

A solution of 0.134 g 2,6-diamino-N-hydroxy-isonicotinamidine (Example 108a) in 2.00 ml acetic acid anhydride was heated to reflux for 4 h. The reaction mixture was partitioned between water and ethyl acetate. The phases were separated and the organic phase was dried over magnesium sulfate dihydrate and evaporated. The residue was taken up in 2 ml 2N hydrochloric acid and heated to reflux for 1.5 h. The mixture neutralized by addition of 3 ml 1N sodium hydroxide and partitioned between water and ethyl acetate. The phases were separated and the organic phase was washed with brine and evaporated to yield 0.071 g of the title compound as brown solid.

109b) 1-[6-Amino-4-(5-methyl-[1,2,4]oxadiazol-3-yl)-pyridin-2-yl]-3-methyl-urea In analogy to example 3a, by replacing 2.6-diamino-4-bromopyridine with 4-(5-methyl-[1,2,4]oxadiazol-3-yl)-pyridine-2,6-diamine the title compound was obtained as white crystals. MS (ISP) M+H$^+$=249.4

Example 110

N-{[6-Amino-4-(5-methyl-1,2,4-oxadiazol-3-yl)pyridin-2-yl]carbamoyl}-5-(2-methoxyethyl)-4-methylthiophene-2-sulfonamide In analogy to example 4, by replacing (6-amino-4-bromopyridin-2-yl)-urea with 4-(5-methyl-[1,2,4]oxadiazol-3-yl)-pyridine-2,6-diamine, the title compound was obtained as white solid. MS (ISN) M–H$^+$=451.1

Example 111

2-{3-methyl-5-[({[6-methyl-4-(trifluoromethyl)pyridin-2-yl]carbamoyl}amino)sulfonyl]-2-thienyl}ethyl acetate To a solution of 0.235 g acetic acid 2-(3-methyl-5-sulfamoyl-thiophen-2-yl)-ethyl ester in 5 ml acetonitrile was added 0.188 g phenylchloroformate and 0.252 g triethylamine at 0° C. and the mixture was stirred at this temperature for 2 h. To the resulting suspension was added 0.220 g 6-methyl-4-trifluoromethyl-pyridin-2-ylamine and the mixture was heated to 60C for 18 h. The reaction mixture was partitioned between 10% citric acid and ethyl acetate. The phases were separated and the organic phase was washed with brine and evaporated. The residue was triturated with diethylether. The solid was collected by filtration to yield 0.736 g of the title compound as light yellow crystals. MS (ISN) M–H$^+$= 463.9

Example 112

6-[({[5-(2-Methoxyethyl)-4-methyl-2-thienyl]sulfonyl}carbamoyl)amino]4-(methylthio)pyridine-2-carboxamide In analogy to example 4, by replacing (6-amino-4-bromopyridin-2-yl)-urea with 6-amino-4-methylsulfanyl-pyridine-2-carboxylic acid amide, the title compound was obtained as white solid. MS (ISN) M–H$^+$=443.4

112 a) 6-Amino-4-methylsulfanyl-pyridine-2-carboxylic acid amide

A mixture of 0.099 g 6-amino-4-methylsulfanyl-pyridine-2-carboxylic acid methyl ester in 4 ml 25% aqueous ammonia was stirred at room temperature for 24 h. The solid was collected by filtration washed with water and dried to constant weight to yield 0.070 g of the title compound as white crystals melting at 158-159° C.

Example 113

6-[({[5-(2-Methoxyethyl)-4-methyl-2-thienyl]sulfonyl}carbamoyl)amino]-N-methyl-4-(methylthio)pyridine-2-carboxamide In analogy to example 4, by replacing (6-amino-4-bromopyridin-2-yl)-urea with 6-amino-4-methylsulfanyl-pyridine-2-carboxylic acid methylamide, the title compound was obtained as white solid. MS (ISN) M–H$^+$=457.0

113a) 6-Amino-4-methylsulfanyl-pyridine-2-carboxylic acid methylamide

A solution of 0.099 g 6-amino-4-methylsulfanyl-pyridine-2-carboxylic acid methyl ester in 2 ml methylamine 2M in tetrahydrofuran was kept at room temperature for 24 h. The solvents were evaporated and the residue was recrystallized from water to yield 0.054 g of the title compound as white crystals melting at 89-91° C.

Example 114

5-(2-Hydroxyethyl)-4-methyl-N-{[6-methyl-4-(trifluoromethyl)pyridin-2-yl]carbamoyl}thiophene-2-sulfonamide To a solution of 0.25 g 2-{3-methyl-5-[({[6-methyl-4-(trifluoromethyl)pyridin-2-yl]carbamoyl}amino)sulfonyl]-2-thienyl}ethyl acetate in 5 ml methanol was added 0.01 ml 28% aqueous sodium hydroxide and the mixture was kept at room temperature for 3 h. The reaction mixture was partitioned between 10% citric acid and ethyl acetate. The phases were separated and the organic phase was washed with brine and evaporated. The residue was triturated with t-butylmethyl ether/heptane to yield 0.177 g of the title compound as off white powder MS (ISN) M–H$^+$=422.4.

Example 115

N'-Hydroxy-6-[({[5-(2-methoxyethyl)-4-methyl-2-thienyl]sulfonyl}carbamoyl)amino]-4-(methylthio)pyridine-2-carboximidamide In analogy to example 4, by replacing (6-amino-4-bromopyridin-2-yl)-urea with 6-amino-N-hydroxy-4-methylsulfanyl-pyridine-2-carboxamidine, the title compound was obtained as white solid. MS (ISN) M–H$^+$=458.3

115a) 6-Amino-N-hydroxy-4-methylsulfanyl-pyridine-2-carboxamidine

To a solution of 0.179 g 6-amino-4-methylsulfanyl-pyridine-2-carbonitrile in 2.7 ml ethanol and 1.3 ml water was added 0.151 g hydroxylamine hydrochloride and 0.344 g sodium carbonate and the mixture was stirred at 85° C. for 1 h. The mixture was charged onto a 10 g kartusche (Varian Chem Elut 12198007) and the product was eluted with ethyl acetate and purified by chromatography on silica gel with dichloromethane:methanol:ammonia=8:2:0.2 to yield 0.120 g of the title compound as white solid. MS (ISP) M+H$^+$=199.0

Example 115b)
6-Amino-4-methylsulfanyl-pyridine-2-carbonitrile

To a solution of 0.481 g 6-bromo-4-methylsulfanyl-pyridin-2-ylamine in 7 ml dimethylformamide was added 0.295 g copper(I)cyanide and the mixture was heated under microwave irradiation to 200° C. for 200 sec. The reaction mixture was partitioned between satd' ammoinum chloride and ethyl acetate. The phases were separated and the organic phase was washed with water (2×) and brine dried over sodium sulfate and evaporated. The residue was purified by chromatography on silica gel with heptane:ethyl; acetate=1:1 to yield the title compound as light brown solid. MS (ISP) M+H$^+$=166.1

Example 116

5-(2-Methoxyethyl)-4-methyl-N-{[6-(5-methyl-1,2,4-oxadiazol-3-yl)-4-(methylthio)pyridin-2-yl]carbamoyl}thiophene-2-sulfonamide In analogy to example 4, by replacing (6-amino-4-bromo-pyridin-2-yl)-urea with 4-methoxy-6-(5-methyl-[1,2,4]oxadiazol-3-yl)-pyridin-2-ylamine, the title compound was obtained as white solid. MS (ISN) M–H$^+$=451.1

116a) 4-Methoxy-6-(5-methyl-[1,2,4]oxadiazol-3-yl)-pyridin-2-ylamine

In analogy to the conversion of 2.6-diamino-4-cyano-pyridine to 4-(5-methyl-[1,2,4]oxadiazol-3-yl)-pyridine-2,6-diamine (Example 109a) the title compound was obtained from 6-amino-4-methoxy-pyridine-2-carbonitrile (example 58a) as yellow solid MS (ISP) M+H$^+$=207.3

Example 117

5-(2-methoxyethyl)-4-methyl-N-{[6-(5-methyl-1,2,4-oxadiazol-3-yl)-4-(methylthio)pyridin-2-yl]carbamoyl}thiophene-2-sulfonamide In analogy to example 4, by replacing (6-amino-4-bromo-pyridin-2-yl)-urea with 6-(5-methyl-[1,2,4]oxadiazol-3-yl)-4-methylsulfanyl-pyridin-2-ylamine, the title compound was obtained as white solid. MS (ISN) M–H$^+$=482.0

117a) 6-(5-Methyl-[1,2,4]oxadiazol-3-yl)-4-methyl-sulfanyl-pyridin-2-ylamine A solution of 0.094 g 6-Amino-N-hydroxy-4-methylsulfanyl-pyridine-2-carboxamidine in 1.5 ml acetic acid anhydride was heated to reflux for 6 h. The solvent was evaporated and the solidifying residue was taken up in 1.5 ml 1N hydrochloric acid and heated to reflux for 1 h. The reaction mixture was partitioned between 2 ml 1N aqueous sodium hydroxide and ethyl acetate. The phases were separated and the organic phase was washed with water and brine dried over magnesium sulfate and evaporated. The residue triturated in ethyl acetate (1 ml) and the resulting solid was collected by filtration to yield 0.057 g of the title compound as light yellow solid MS (ISP) M+H$^+$=223.3

Example 118

Methyl-6-[({[5-(2-methoxyethyl)-4-methyl-2-thienyl]sulfonyl}carbamoyl)amino]-4-(methoxy)pyridine-2-carboxylate In analogy to example 4, by replacing (6-amino-4-bromo-pyridin-2-yl)-urea with 6-amino-4-methoxy-pyridine-2-carboxylic acid methyl ester, the title compound was obtained as white solid. MS (ISN) M–H$^+$=442.0

118a) 6-Amino-4-methoxy-pyridine-2-carboxylic acid methyl ester

To a solution of 0.124 g 6-bromo-4-methoxy-pyridin-2-ylamine in 5 ml methanol was added 0.093 g triethylamine and 0.020 g PdCl2dppf.CH2Cl2 and the mixture was stirred under an atmosphere of 70 bar of carbon monoxide at 130° C. for 20 h. The solvent was evaporated and the residue was purified by chromatography on silica gel with heptane: ethyl acetate mixtures to yield the title compound as reddish solid MS (ISP) M+H$^+$=183.1

118b) 6-Bromo-4-methoxy-pyridin-2-ylamine

A solution of 2.00 g 2,6-dibromo-4-methoxy-pyridine in 80 g liquid ammonia under was heated in an autoclave to 140° C. for 4 h. The reaction was cooled to room, evaporated and the residue was purified by silica column chromatography to yield 0.457 g of the title compound as white solid. MS (ISP) M+H$^+$=203.2 205.5

Example 119

6-[({[5-(2-Methoxyethyl)-4-methyl-2-thienyl]sulfonyl}carbamoyl)amino]-4-(methoxy)pyridine-2-carboxamide In analogy to example 4, by replacing (6-amino-4-bromo-pyridin-2-yl)-urea with 6-amino-4-methoxy-pyridine-2-carboxylic acid amide, the title compound was obtained as white solid. MS (ISN) M–H$^+$=427.4

119a) 6-Amino-4-methoxy-pyridine-2-carboxylic acid amide

In analogy to example 103b, by replacing 2,6-diaminoisonicotinic acid ethyl ester with 6-amino-4-methoxy-pyridine-2-carboxylic acid methyl ester and using 25% aqueous ammonia instead of methylamine, the title compound was obtained as white solid. MS (ISP) M+H$^+$=168.4

Example 120

5-Methyl-N-{[6-methyl-4-(trifluoromethyl)pyridin-2-yl]carbamoyl}thiophene-3-sulfonamide In analogy to example 96, by replacing 5-(2-methoxyethyl)-4-methyl-thiophene-2-sulfonic acid amide with 5-methyl-thiophene-3-sulfonic acid amide, the title compound was obtained as white solid. MS (ISN) M–H$^+$=377.9

Example 121

5-Methyl-N-{[6-methyl-4-(trifluoromethyl)pyridin-2-yl]carbamoyl}thiophene-2-sulfonamide In analogy to example 96, by replacing 5-(2-methoxyethyl)-4-methyl-thiophene-2-sulfonic acid amide with 5-methyl-thiophene-2-sulfonic acid amide, the title compound was obtained as white solid. MS (ISN) M−H+=377.9

Example 122

4-Methyl-N-{[6-methyl-4-(trifluoromethyl)pyridin-2-yl]carbamoyl}thiophene-2-sulfonamide In analogy to example 96, by replacing 5-(2-methoxyethyl)-4-methyl-thiophene-2-sulfonic acid amide with 4-methyl-thiophene-2-sulfonic acid amide, the title compound was obtained as white solid. MS (ISN) M−H+=377.9

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound, selected from the group consisting of:
5-Chloro-N-({4-methoxy-6-[(methylcarbamoyl)amino]pyridin-2-yl}carbamoyl)-1-benzothiophene-2-sulfonamide;
N-{[4-Bromo-6-(carbamoylamino)pyridin-2-yl]carbamoyl}-5-methylthiophene-3-sulfonamide;
N-({4-bromo-6-[(methylcarbamoyl)amino]pyridin-2-yl}carbamoyl)-5-methylthiophene-3-sulfonamide;
N-{[4-Bromo-6-(carbamoylamino)pyridin-2-yl]carbamoyl}-5-(2-methoxyethyl)-4-methylthiophene-2-sulfonamide;
5-Methoxy-N-({4-methoxy-6-[(methylcarbamoyl)amino]pyridin-2-yl}carbamoyl)-1-benzothiophene-3-sulfonamide;
5-Isobutyl-N-({4-methoxy-6-[(methylcarbamoyl)amino]pyridin-2-yl}carbamoyl)-4-methylthiophene-2-sulfonamide;
N-({4-Methoxy-6-[(methylcarbamoyDamino]pyridin-2-yl}carbamoyl)-5-methyl-1-benzothiophene-2-sulfonamide;
N-({4-Bromo-6[(methylcarbamoyl)amino]pyridin-2-yl}carbamoyl)-5-(2-methoxyethyl)-4-methylthiophene-2-sulfonamide;
N-[[[4-methoxy-6-[[emethylamino)carbonyl]amino]-2-pyridinyl]amino]carbonyl]-5-methyl-3-thiophene-sulfonamide;
N-[(6-Amino-4-bromopyridin-2-yl)carbamoyl]-5-(2-methoxyethyl)-4-methylthiophene-2-sulfonamide;
N-[(6-Amino-4-bromopyridin-2-yl)carbamoyl]-4-chloro-5-(2-methoxyethyl)pthiophene-2-sulfonamide;
6-Methoxy-N-({4-methoxy-6-[(methylcarbamoy)amino]pyridin-2-yl}carbamoyl)-1-benzothiophene-2-sulfonamide;
5-Methoxy-N-({4-methoxy-6-[(methylcarbamoy)amino]pyridin-2-yl}carbamoyl)-1-benzothiophene-2-sulfonamide;
5-(2-Methoxyethyl)-4-methyl-N-({6-[(methylcarbamoyDamino]-4-(methylthio)pyridin-2-yl}carbamoyl)thiophene-2-sulfonamide;
N-({4-Bromo-6-[(2,2-difluoroethyl)amino]pyridin-2-yl}carbamoyl)-4-chloro-5-(2-methoxyethyl)thiophene-2-sulfonamide;
5-Methyl-N-({6-[(methylcarbamoyl)amino]-4-(methylthio)pyridin-2-yl}carbamoyl)thiophene-3-sulfonamide;
N-{[6-(Carbamoylamino)-4-(methylthio)pyridin-2-yl]carbamoyl }-5-(2-methoxyethyl)-4-methylthiophene-2-sulfonamide;
5-(2-Methoxyethyl)-N-[(4-methoxy-6-{[(methylamino)carbonothioyl]amino}pyridin-2-yl)carbamoyl]4-methylthiophene-2-sulfonamide; and
N-({4-Bromo-6-[(2,2-difluoroethyl)amino]pyridin-2-yl}carbamoyl)-5-(2-methoxyethyl)-4-methylthiophene-2-sulfonamide.

2. A compound, selected from the group consisting of:
5-(2-Methoxyethyl)-N-({4-methoxy-6-[(methylcarbamoyl)amino]pyridin-2-yl}carbamoyl)-4-methylthiophene-2-sulfonamide;
N-[(6-Amino-4-bromopyridin-2-yl)carbamoyl]-5-(methoxymethyl)-4-methylthiophene-2-sulfonamide;
N-{[6-(Carbamoylamino)-4-methoxypyridin-2-yl]carbamoyl}-5-methylthiophene-3-sulfonamide;
N-({4-Cyano-6-[(methylcarbamoyl)amino]pyridin-2-yl }carbamoyl)-5-(2-methoxyethyl)-4-methylthiophene-2-sulfonamide;
N-{[6-(Carbamoylamino)-4-methoxypyridin-2-yl]carbamoyl}-5-(2-methoxyethyl)-4-methylthiophene-2-sulfonamide;
N-{[6-Bromo-4-(methylthio)pyridin-2-yl]carbamoyl}-5-(2-methoxyethyl)-4-methylthiophene-2-sulfonamide;
7-Methoxy-N-({4-methoxy-6-[(methylcarbamoyl)amino]pyridin-2-yl}carbamoyl)-1-methyl-1H-indole-3-sulfonamide;
N-({4-Methoxy-6-[(methylcarbamoyl)amino]pyridin-2-yl }carbamoyl)-3-methylbenzenesulfonamide;
N-[(6-Amino-4-bromopyridin-2-yl)carbamoyl]-3-chlorobenzenesulfonamide;
5-(Methoxymethyl)-N-({4-methoxy-6-[(methylcarbamoyl)amino]pyridin-2-yl}carbamoyl)thiophene-3-sulfonamide;
N-[(6-Amino-4-methoxypyridin-2-yl)carbamoyl]-5-(2-methoxyethyl)-4-methylthiophene-2-sulfonamide;

N-[(4-Bromo-6-morpholin-4-ylpyridin-2-yl)carbamoyl]-5-(2-methoxyethyl)-4-methylthiophene-2-sulfonamide;

N-{[6-Amino-4-(methylthio)pyridin-2-yl]carbamoyl}-5-(2-methoxyethyl)-4-methylthiophene-2-sulfonamide;

5-(2-Methoxyethyl)-4-methyl-N-{[4-(trifluoromethyl)pyridin-2-yl]carbamoyl}thiophene-2-sulfonamide;

N-[(6-Amino-4-bromopyridin-2-yl)carbamoyl]-2,3-dihydro-1-benzofuran-5-sulfonamide;

N-({4-Ethoxy-6-[(methylcarbamoyl)amino]pyridin-2-yl}carbamoyl)-5-(2-methoxyethyl)-4-methylthiophene-2-sulfonamide;

N-[(6-Amino-4-bromopyridin-2-yl)carbamoyl]-3-methylbenzenesulfonamide;

N-[(6-Amino-4-bromopyridin-2-yl)carbamoyl]-2,3-dihydro-1,4-benzodioxine-6-sulfonamide; and 5-(2-Methoxyethoxy)-N-({4-methoxy-6-[(methylcarbamoyl)amino]pyridin-2-yl}carbamoyl)-4-methylthiophene-2-sulfonamide.

3. A compound, selected from the group consisting of:

N-({4-Bromo-6-[(2,2-difluoroethyl)amino]pyridin-2-yl}carbamoyl)-3-methylbenzenesulfonamide;

N-{[6-(Carbamoylamino)-4-ethoxypyridin-2-yl]carbamoyl}5-(2-methoxyethyl)-4-methylthiophene-2-sulfonamide;

N-({4-Bromo-6-[(2,2-difluoroethyl)amino]pyridin-2-yl}carbamoyl)-3-chlorobenzenesulfonamide;

5-(2-Methoxyethyl)-4-methyl-N-({4-(trifluoromethyl)-6-[4-(trifluoromethyl)phenyl]pyridin-2-yl}carbamoyl)thiophene-2-sulfonamide;

N-{[6-Amino-4-(methylthio)pyridin-2-yl]carbamoyl}-5-methylthiophene-3-sulfonamide;

N-[(6-Amino-4-bromopyridin-2-yl)carbamoyl]-5-(methoxymethyl)-4-methylfuran-2-sulfonamide;

N-({6-[(2-Fluoroethyl)amino]-4-(methylthio)pyridin-2-yl}carbamoyl)-5-(2-methoxyethyl)-4-methylthiophene-2-sulfonamide;

5-(2-Methoxyethyl)-4-methyl-N-{[4-methyl-6-(1,2,3,4-tetrahydronaphthalen-2-yl)pyridin-2-yl]carbamoyl}thiophene-2-sulfonamide;

N-({4-Bromo-6-[(2,2-difluoroethyl)amino]pyridin-2-yl}carbamoyl)-2,3-dihydro-1-benzofuran-5-sulfonamide;

N-({6-[(2-Hydroxyethyl)amino]-4-(methylthio)pyridin-2-yl}carbamoyl)-5-(2-methoxyethyl)-4-methylthiophene-2-sulfonamide;

7-(2-Methoxyethoxy)-N-({4-methoxy-6-[(methylcarbamoyl)amino]pyridin-2-yl}carbamoyl)-1-methyl-1H-indole-2-sulfonamide;

5-(2-Methoxyethyl)-4-methyl-N-({6-[(methylcarbamoyl)amino]-4-(methylsulfonyl)pyridin-2-yl}carbamoyl)thiophene-2-sulfonamide;

N-({4-Bromo-6-[(2,2-difluoroethyl)amino]pyridin-2-yl}carbamoyl)-4-(2-methoxyethoxy)-3-methylbenzenesulfonamide;

N,N'-[(4-Bromopyridine-2,6-diyl)bis(iminocarbonyl)]bis[3-(difluoromethoxy)benzene-sulfonamide];

N-{[6-Amino-4-(methylthio)pyridin-2-yl]carbamoyl }-7-methoxy-1-methyl-1H-indole-3-sulfonamide;

N-({4-Bromo-6-[(dimethylcarbamoyl)amino]pyridin-2-yl}carbamoyl)-5-(2-methoxyethyl)-4-methylthiophene-2-sulfonamide;

N-[(4-Bromopyridin-2-yl)carbamoyl]-3-chlorobenzenesulfonamide;

N-{[6-(3,4-Dihydroisoquinolin-2(1H)-yl)-4-methylpyridin-2-yl]carbamoyl}-5-(2-methoxyethyl)-4-methylthiophene-2-sulfonamide;

N-[(6-Amino-4-bromopyridin-2-yl)carbamoyl]-4-(2-methoxyethoxy)-3-methylbenzenesulfonamide; and N-[(6-Cyano-4-methoxypyridin-2-yl)carbamoyl]-5-(2-methoxyethyl)4-methylthiophene-2-sulfonamide.

4. A compound, selected from the group consisting of:

N-({6-[(Dimethylcarbamoyl)amino]-4-methoxypyridin-2-yl}carbamoyl)-5-(2-methoxyethyl)-4-methylthiophene-2-sulfonamide;

N-[(4-Bromopyridin-2-yl)carbamoyl]-3-methylbenzenesulfonamide;

Methyl-{4-methoxy-6-[({[5-(2-methoxyethyl)-4-methyl-2-thienyl]sulfonyl}carbamoyy)amino]pyridin-2-yl}carbamate;

N-[(6-Amino-4-cyanopyridin-2-yl)carbamoyl]-5-(2-methoxyethyl)-4-methylthiophene-2-sulfonamide;

N-[(6-Amino-4-bromopyridin-2-yl)carbamoyl]-3-(difluoromethoxy)benzenesulfonamide;

N-[(6-Amino-4-ethoxypyridin-2-yl)carbamoyl]-5-(2-methoxyethyl)-4-methylthiophene-2-sulfonamide;

N-[(4-Bromopyridin-2-yl)carbamoyl]-5-[4-(cyanomethyl)phenyl]thiophene-2-sulfonamide;

N-({4-Bromo-6-[(2,4-dimethoxybenzyl)amino]pyridin-2-yl}carbamoyl)-5-(2-methoxyethyl)-4-methylthiophene-2-sulfonamide;

N,N'-[(4-Bromopyridine-2,6-diyl)bis(iminocarbonyl)]bis(3-chlorobenzenesulfonamide);

N-({6-[(Dimethylcarbamoyl)amino]-4-ethoxypyridin-2-yl}carbamoyl)-5-(2-methoxyethyl)-4-methylthiophene-2-sulfonamide;

N-[(4-Bromopyridin-2-yl)carbamoyl]-4-chlorobenzenesulfonamide;

2-[(3-{[({4-Methoxy-6-[(methylcarbamoyl)amino]pyridin-2-yl}carbamoyl)amino]sulfonyl}-1-methyl-1H-indol-7-yl)oxy]-N,N-dimethylacetamide;

N-{[6-Hydroxy-4-(methylthio)pyridin-2-yl]carbamoyl}-5-(2-methoxyethyl)-4-methylthiophene-2-sulfonamide;

N-[(6-Chloropyridin-2-yl)carbamoyl]-3-methylbenzenesulfonamide;

Methyl-4-({6-[({[5-(2-methoxyethyl)-4-methyl-2-thienyl]sulfonyl}carbamoyl)amino]-4-(methylthio)pyridin-2-yl }amino)butanoate;

N-({6[(3-Hydroxypropyl)amino]-4-(methylthio)pyridin-2-yl }carbamoyl-5-(2-methoxyethyl)-4-methylthiophene-2-sulfonamide;

5-(2-Methoxyethyl)-4-methyl-N-({4-(methylthio)-6-[(3,3,3-trifluoropropyl)amino]pyridin-2-yl}carbamoyl)thiophene-2-sulfonamide;

N-({4-(Ethylthio)-6-[(2-hydroxyethyl)amino]pyridin-2-yl}carbamoyl)-5-(2-methoxyethyl)-4-methylthiophene-2-sulfonamide;

2-{3-Methyl-5-[({[4-(trifluoromethyl)pyridin-2-yl]carbamoyl}amino)sulfonyl]-2-thienyl}ethyl acetate; and 5-(2-Hydroxyethyl)-4-methyl-N-{[4-(trifluoromethyl)pyridin-2-yl]carbamoyl}thiophene-2-sulfonamide.

5. A compound, selected from the group consisting of:

N-{[6-Amino-5-fluoro-4-(trifluoromethyl)pyridin-2-yl]carbamoyl}-5-(2-methoxyethyl)-4-methylthiophene-2-sulfonamide;

5-(2-Methoxyethyl)-4-methyl-N-({6-[(2-methylprop-2-en-1-yl)amino]-4-(methylthio)pyridin-2-yl}carbamoyl)thiophene-2-sulfonamide;

2-{5-[({[6-Amino-5-fluoro-4-(trifluoromethyl)pyridin-2-yl]carbamoyl}amino)sulfonyl]-3-methyl-2-thienyl}ethyl acetate;

N-[(6-Amino-4-bromopyridin-2-yl)carbamoyl]-1-benzofuran-3-sulfonamide;
N-[(6-Amino-4-bromopyridin-2-yl)carbamoyl]-5-bromo-1-benzofuran-3-sulfonamide;
N-{[6-Amino-5-fluoro-4-(trifluoromethyl)ppyridin-2-yl]carbamoy}-5-(2-hydroxyethyl)-4-methylthiophene-2-sulfonamide;
N-{[6-Amino-4-(trifluoromethyl)pyridin-2-yl]carbamoyl}-5-(2-methoxyethyl)-4-methylthiophene-2-sulfonamide;
5-(2-Methoxyethyl)-4-methyl-N-{[6-methyl-4-(methylthio)pyridin-2-yl]carbamoyl}thiophene-2-sulfonamide;
N-{[6-Amino-4-(methylthio)pyridin-2-yl]carbamoyl}-5-bromo-1-benzofuran-3-sulfonamide;
Sodium-6-[({[5-(2-methoxyethyl)-4-methyl-2-thienyl]sulfonyl}carbamoyl)amino]-4-(methylthio)pyridine-2-carboxylate;
N-({6-[(Methylcarbamoyl)amino]-4-(methylthio)pyridin-2-yl}carbamoyl)-1-benzofuran-3-sulfonamide;
N-{[6-chloro-4-(trifluoromethyl)pyridin-2-yl]carbamoyl}-5-(2-methoxyethyl)-4-methylthiophene-2-sulfonamide;
Methyl-6-[({[5-(2-methoxyethyl)-4-methyl-2-thienyl]sulfonyl}carbamoyl)amino]-4-(trifluoromethyl)pyridine-2-carboxylate;
Methyl-6-[({[5-(2-acetoxyethyl)-4-methyl-2-thienyl]sulfonyl}carbamoyl)amino]-4-(trifluoromethyl)pyridine-2-carboxylate;
2-{5-[({[6-chloro-4-(trifluoromethyl)pyridin-2-yl]carbamoyl}amino)sulfonyl]-3-methyl-2thienyl}ethyl acetate;
5-(2-Methoxyethyl)-4-methyl-N-({6-[(methylcarbamoyl)amino]-4-(methylsulfinyl)pyridin-2-yl}carbamoyl)thiophene-2-sulfonamide;
N-{[6-(Carbamoylamino)-4-(methylsulfinyl)pyridin-2-yl]carbamoyl}-5-(2-methoxyethyl)-4-methylthiophene-2-sulfonamide;
5-(2-methoxyethyl)-4-methyl-N-{[6-methyl-4-(trifluoromethyl)pyridin-2-yl]carbamoyl}thiophene-2-sulfonamide; and
Methyl-6-[({[5-(2-hydroxyethyl)-4-methyl-2-thienyl]sulfonyl}carbamoyl)amino]-4-(trifluoromethyl)pyridine-2-carboxamide.

6. A compound, selected from the group consisting of:
Methyl-6-({[(5-methyl-3-thienyl)sulfonyl]carbamoyl}amino)-4-(trifluoromethyl)pyridine-2-carboxylate;
Ethyl-2-[({[5-(2-methoxyethyl)-4-methyl-2-thienyl]sulfonyl}carbamoyl)amino]-6-[(methylcarbamoyl)amino]isonicotinate;
Ethyl-2-amino-6-[({[5-(2-methoxyethyl)-4-methyl-2-thienyl]sulfonyl}carbamoyl)amino]isonicotinate;
2-[({[5-(2-Methoxyethyl)-4-methyl-2-thienyl]sulfonyl}carbamoyl)amino]-6-[(methylcarbamoyl)amino]isonicotinamide;
2-Amino-6-[({[5-(2-methoxyethyl)-4-methyl-2-thienyl]sulfonyl}carbamoyl)amino]isonicotinamide;
2-[({[5-(2-Methoxyethyl)-4-methyl-2-thienyl]sulfonyl}carbamoyl)amino]-N-methyl-6-[(methylcarbamoyl)amino]isonicotinamide;
2-Amino-6-[({[5-(2-methoxyethyl)-4-methyl-2-thienyl]sulfonyl}carbamoyl)amino]-N-methylisonicotinamide;
Methyl-6-[({[5-(2-hydroxyethyl)-4-methyl-2-thienyl]sulfonyl}carbamoyl)amino]-4-(trifluoromethyl)pyridine-2-carboxylate;
5-(2-Hydroxyethyl)-N-{[6-(hydroxymethyl)-4-(trifluoromethyl)pyridin-2-yl]carbamoyl}-4-methylthiophene-2-sulfonamide;
N'-Hydroxy-2-[({[5-(2-methoxyethyl)-4-methyl-2-thienyl]sulfonyl}carbamoyl)amino]-6-[(methylcarbamoyl)amino]pyridine-4-carboximidamide;
2-Amino-N'-hydroxy-6-[({[5-(2-methoxyethyl)-4-methyl-2-thienyl]sulfonyl}carbamoyl)amino]pyridine-4-carboximidamide;
5-(2-Methoxyethyl)-4-methyl-N-({6-[(methylcarbamoyl)amino]-4-(5-methyl-1,2,4-oxadiazol-3-yl)pyridin-2-yl}carbamoyl)thiophene-2-sulfonamide;
N-{[6-Amino-4-(5-methyl-1,2,4-oxadiazol-3-yl)pyridin-2-yl]carbamoyl}-5-(2-methoxyethyl)-4-methylthiophene-2-sulfonamide;
2-{3-methyl-5-[({[6-methyl-4-(trifluoromethyl)pyridin-2-yl]carbamoyl}amino)sulfonyl]-2-thienyl }ethyl acetate;
6-[({[5-(2-Methoxyethyl)-4-methyl-2-thienyl]sulfonyl}carbamoyl)amino]-4-(methylthio)pyridine-2-carboxamide;
6-[({[5-(2-Methoxyethyl)-4-methyl-2-thienyl]sulfonyl}carbamoyl)amino]-N-methyl-4(methylthio)pyridine-2-carboxamide;
5-(2-Hydroxyethyl)-4-methyl-N-{[6-methyl-4-(trifluoromethyl)pyridin-2-yl]carbamoyl}thiophene-2-sulfonamide;
N'-Hydroxy-6-[({[5-(2-methoxyethyl)-4-methyl-2-thienyl]sulfonyl}carbamoyl)amino]-4-(methylthio)pyridine-2-carboximidamide;
5-(2-Methoxyethyl)-4-methyl-N-{[6-(5-methyl-1,2,4-oxadiazol-3-yl)-4-(methylthio)pyridin-2-yl]carbamoyl}thiophene-2-sulfonamide;
5-(2-methoxyethyl)-4-methyl-N-{[6-(5-methyl-1,2,4-oxadiazol-3-yl)-4-(methylthio)pyridin-2-yl]carbamoyl}thiophene-2-sulfonamide;
Methyl-6-[({[5-(2-methoxyethyl)-4-methyl-2-thienyl]sulfonyl}carbamoyl)amino]-4-(methoxy)pyridine-2-carboxylate;
6-[({[5-(2-Methoxyethyl)-4-methyl-2-thienyl]sulfonyl}carbamoyl)amino]-4-(methoxy)pyridine -2-carboxamide ;
5-Methyl-N-{[6-methyl-4-(trifluoromethyl)pyridin-2-yl]carbamoyl}thiophene-3-sulfonamide;
5-Methyl-N-{[6-methyl-4-(trifluoromethyl)pyridin-2-yl]carbamoyl}thiophene-2-sulfonamide and
4-Methyl-N-{[6-methyl-4-(trifluoromethyl)pyridin-2-yl]carbamoyl}thiophene-2-sulfonamide.

7. A compound, selected from the group consisting of:
5-Isobutyl-N-({4-methoxy-6-[(methylcarbamoyl)amino]pyridin-2-yl}carbamoyl)-4-methylthiophene-2-sulfonamide;
N-[[[4-methoxy-6-[[(methylamino)carbonyl]amino]-2-pyridinyl]amino]carbonyl]-5-methyl-3-thiophenesulfonamide;
5-Methyl-N-({6-[(methylcarbamoyl)amino]-4-(methylthio)pyridin-2-yl}carbamoyl)thiophene-3-sulfonamide;
N-{[6-(Carbamoylamino)-4-(methylthio)pyridin-2-yl]carbamoyl}-5-(2-methoxyethyl)-4-methylthiophene-2-sulfonamide;
5-(2-Methoxyethyl)-N-[(4-methoxy-6-{[(methylamino)carbonothioyl]amino}pyridin-2-yl)carbamoyl]-4-methylthiophene-2-sulfonamide;
N-{[6-(Carbamoylamino)-4-methoxypyridin-2-yl]carbamoyl}-5-(2-methoxyethyl)-4-methylthiophene-2-sulfonamide;

7-Methoxy-N-({4-methoxy-6-[(methylcarbamoyl)amino]pyridin-2-yl}carbamoyl)-1-methyl-1H-indole-3-sulfonamide;

N-({6-[(2-Fluoroethyl)amino]-4-(methylthio)pyridin-2-yl}carbamoyl)-5-(2-methoxyethyl)-4-methylthiophene-2-sulfonamide;

N-{[6-Amino-5-fluoro-4-(trifluoromethyl)pyridin-2-yl]carbamoyl}-5-(2-methoxyethyl)-4-methylthiophene-2-sulfonamide;

2-{5-[({[6-Amino-5-fluoro-4-(trifluoromethyl)pyridin-2-yl]carbamoyl}amino)sulfonyl]-3-methyl-2-thienyl}ethyl acetate;

N-{[6-Amino-5-fluoro-4-(trifluoromethyl)pyridin-2-yl]carbamoyl}-5-(2-hydroxyethyl)-4-methylthiophene-2-sulfonamide;

5-(2-Methoxyethyl)-4-methyl-N-{[6-methyl-4-(methylthio)pyridin-2-yl]carbamoyl}thiophene-2-sulfonamide;

5-(2-methoxyethyl)-4-methyl-N-{[6-methyl-4-(trifluoromethyl)pyridin-2-yl]carbamoyl}thiophene-2-sulfonamide;

2-{3-methyl-5-[({[6-methyl-4-(trifluoromethyl)pyridin-2-yl]carbamoyl}amino)sulfonyl]-2-thienyl}ethyl acetate;

5-(2-Hydroxyethyl)-4-methyl-N-{[6-methyl-4-(trifluoromethyl)pyridin-2-yl]carbamoyl}thiophene-2-sulfonamide; and 5-Methyl-N-{[6-methyl-4-(trifluoromethyl)pyridin-2-yl]carbamoyl}thiophene-3-sulfonamide.

\* \* \* \* \*